United States Patent
Koilpillai et al.

(10) Patent No.: US 11,602,537 B2
(45) Date of Patent: Mar. 14, 2023

(54) VARENICLINE COMPOUND AND PROCESS OF MANUFACTURE THEREOF

(71) Applicant: Par Pharmaceutical, Inc., Chestnut Ridge, NY (US)

(72) Inventors: Joseph Prabahar Koilpillai, Tamil Nadu (IN); Sayuj Nath, Tamil Nadu (IN); Satish Patil, Tamil Nadu (IN); Somasundaram Muthuramalingam, Tamil Nadu (IN); Selvakumar Viruthagiri, Tamil Nadu (IN); Mohankumar Lakshmanan, Tamil Nadu (IN)

(73) Assignee: Par Pharmaceutical, Inc., Chestnut Ridge, NY (US)

( * ) Notice: Subject to any disclaimer, the term of this patent is extended or adjusted under 35 U.S.C. 154(b) by 0 days.

(21) Appl. No.: 17/721,857

(22) Filed: Apr. 15, 2022

(65) Prior Publication Data

US 2022/0249508 A1  Aug. 11, 2022

Related U.S. Application Data

(60) Provisional application No. 63/319,043, filed on Mar. 11, 2022.

(51) Int. Cl.
| | | |
|---|---|---|
| *A61K 31/55* | (2006.01) | |
| *C07D 471/18* | (2006.01) | |
| *A61K 47/38* | (2006.01) | |
| *A61K 47/12* | (2006.01) | |
| *A61K 47/02* | (2006.01) | |

(52) U.S. Cl.
CPC ............ *A61K 31/55* (2013.01); *A61K 47/02* (2013.01); *A61K 47/12* (2013.01); *A61K 47/38* (2013.01); *C07D 471/18* (2013.01)

(58) Field of Classification Search
CPC .... C07D 471/08; C07D 471/18; A61K 31/55; A61K 47/02; A61K 47/12; A61K 47/38; A61K 9/1623; C07C 59/255; A61P 1/00
See application file for complete search history.

(56) References Cited

U.S. PATENT DOCUMENTS

| | | | |
|---|---|---|---|
| 6,410,550 B1 | 6/2002 | Coe et al. | |
| 6,890,927 B2 | 5/2005 | Bogle et al. | |
| 7,265,119 B2 | 9/2007 | Bogle et al. | |
| 8,314,235 B2 | 11/2012 | Dixit et al. | |
| 2004/0235850 A1* | 11/2004 | Waterman | A61P 43/00 514/249 |
| 2009/0318460 A1 | 12/2009 | Khan | |
| 2012/0093887 A1† | 4/2012 | Sharma | |
| 2013/0030179 A1 | 1/2013 | Attolino et al. | |

FOREIGN PATENT DOCUMENTS

| | | |
|---|---|---|
| CN | 103896943 B | 9/2016 |
| EP | 1659114 A2 | 5/2006 |
| EP | 1044189 B1 | 2/2008 |
| EP | 1866308 B1 | 10/2008 |
| EP | 2260037 | 12/2010 |
| EP | 2262780 A2 | 12/2010 |
| WO | 2007110730 A2 | 10/2007 |
| WO | 2008/060487 A2 | 5/2008 |
| WO | 2010/005643 A1 | 1/2010 |
| WO | 2010143070 A2 | 12/2010 |
| WO | 2011110954 A1 | 9/2011 |
| WO | WO-2021259396 A2 * | 12/2021 |
| WO | 2022271600 A1 | 12/2022 |

OTHER PUBLICATIONS

Wei et. al., WO 2021259396 A2, English translation, publ. Dec. 30, 2021 (Year: 2021).*
Lu et. al., J. Pharmaceutical & Biomed. Anal., publ. 2018, vol. 155, pp. 306-313 (Year: 2018).*
PubChem—"Compound Summary of N-Nitrosoheptamethyleneimine"; dated Feb. 4, 2022 (21 pages).
"FDA Updates and Press Announcements on Nitrosamine in Varenicline (Chantix)"; dated Jul. 30, 2021 (5 pages).
"Control of Nitrosamine Impurities in Human Drugs—Guidance for Industry"; U.S. Department of Health and Human Services Food and Drug Administration Center for Drug Evaluation and Research (CDER); dated Sep. 2020 (24 pages).
"Assessment Report—Procedure under Article 5(3) of Regulation EC (No) 726/2004 - Nitrosamine impurities in human medicinal products;" European Medicines Agency—Committee for Medicinal Products for Human Use (CHMP); dated Jun. 25, 2020 (90 pages).
FDA "Laboratory analysis of varenicline products" dated Feb. 8, 2022 (2 pages).
"Orange Book: Approved Drug Products with Therapeutic Equivalence Evaluations" dated Feb. 8, 2022 (2 pages).
FDA "Liquid Chromatography-High Resolution Mass Spectrometry (LC-ESI-HRMS) Method for the Determination of Varenicline Nitroso-Drug Substance Related Impurity (NDSRI) in Chantix™ Drug Product and Varenicline Drug Substance" dated Aug. 6, 2021 (6 pages).
"Powder Transfer System | Vacuum Conveying" retrieved on May 11, 2022 from https://www.hanningfield.com/powder-transfer-system-vacuum-conveying/.
"FDA Updates and Press Announcements on Nitrosamine in Varenicline (Chantix)"; dated May 5, 2022 (7 pages).
"CHANTIX® (varenicline) Tablets"; Pfizer Labs; revised Apr. 2010 (11 pages).
"VARENICLINE Tablets;" Par Pharmaceutical; revised Jul. 2021 (2 pages).
"Endo Launches First and Only Generic Version of Chantix® (varenicline) Tablets in the United States;" Press Release dated Sep. 22, 2021 (2 pages).
"APO-VARENICLINE—varenicline tablet, film coated;" Apotex Corp; Important Prescribing Information dated Jul. 2, 2021 (110 pages).

(Continued)

*Primary Examiner* — Sarah Pihonak
(74) *Attorney, Agent, or Firm* — Mayer Brown LLP

(57) ABSTRACT

The present disclosure relates to the field of synthesizing substantially pure varenicline and its intermediates. It also relates to the pharmaceutical compositions comprising varenicline and the method of use of these pharmaceutical compositions for smoking cessation.

11 Claims, 18 Drawing Sheets

(56) References Cited

OTHER PUBLICATIONS

United States Food & Drug Administration, Orange Book: Approved Drug Products with Therapeutic Equivalence Evaluations For Varenicline, Oct. 16, 2022.
Endo, Q1 2022 Earnings Report, 2022.
Endo, Second-Quarter Financial Performance, Aug. 9, 2022.
Noah Higgins-Dunn, Pfizer halted Chantix distribution then recalled a dozen batches. Now, a generic's here to help fill the shortage, Fierce Pharma, https://www.fiercepharma.com/pharma/endo-s-smoking-cessation-generic-rushed-over-fda-s-finish-line-effort-to-fill-chantix. Aug. 12, 2021.
Certified English Translation of PCT/CN2021/122645 (published as WO 2021/259396).

\* cited by examiner
† cited by third party

Peak List #1

| Scan | | Angle | Net Intensity | Rel. Intensity |
|---|---|---|---|---|
| 09152021_Varenicline B.No_VW0020520 | Tartrate API | 5.849 | 2722 | 14.9 % |
| 09152021_Varenicline B.No_VW0020520 | Tartrate API | 11.695 | 1483 | 8.1 % |
| 09152021_Varenicline B.No_VW0020520 | Tartrate API | 12.772 | 3939 | 21.6 % |
| 09152021_Varenicline B.No_VW0020520 | Tartrate API | 14.358 | 5427 | 29.7 % |
| 09152021_Varenicline B.No_VW0020520 | Tartrate API | 15.272 | 645 | 3.5 % |
| 09152021_Varenicline B.No_VW0020520 | Tartrate API | 16.371 | 5277 | 28.9 % |
| 09152021_Varenicline B.No_VW0020520 | Tartrate API | 16.932 | 7484 | 41.0 % |
| 09152021_Varenicline B.No_VW0020520 | Tartrate API | 17.079 | 8901 | 48.8 % |
| 09152021_Varenicline B.No_VW0020520 | Tartrate API | 17.742 | 1055 | 5.8 % |
| 09152021_Varenicline B.No_VW0020520 | Tartrate API | 18.718 | 817 | 4.5 % |
| 09152021_Varenicline B.No_VW0020520 | Tartrate API | 19.056 | 2085 | 11.4 % |
| 09152021_Varenicline B.No_VW0020520 | Tartrate API | 20.837 | 972 | 5.3 % |
| 09152021_Varenicline B.No_VW0020520 | Tartrate API | 21.165 | 951 | 5.2 % |
| 09152021_Varenicline B.No_VW0020520 | Tartrate API | 21.732 | 18243 | 100.0 % |
| 09152021_Varenicline B.No_VW0020520 | Tartrate API | 22.493 | 618 | 3.4 % |
| 09152021_Varenicline B.No_VW0020520 | Tartrate API | 23.727 | 4698 | 25.8 % |
| 09152021_Varenicline B.No_VW0020520 | Tartrate API | 24.302 | 1654 | 9.1 % |
| 09152021_Varenicline B.No_VW0020520 | Tartrate API | 25.061 | 2012 | 11.0 % |
| 09152021_Varenicline B.No_VW0020520 | Tartrate API | 25.799 | 1668 | 9.1 % |
| 09152021_Varenicline B.No_VW0020520 | Tartrate API | 26.795 | 945 | 5.2 % |
| 09152021_Varenicline B.No_VW0020520 | Tartrate API | 27.735 | 1180 | 6.5 % |
| 09152021_Varenicline B.No_VW0020520 | Tartrate API | 29.154 | 1270 | 7.0 % |
| 09152021_Varenicline B.No_VW0020520 | Tartrate API | 30.034 | 526 | 2.9 % |
| 09152021_Varenicline B.No_VW0020520 | Tartrate API | 31.798 | 1939 | 10.6 % |
| 09152021_Varenicline B.No_VW0020520 | Tartrate API | 32.442 | 342 | 1.9 % |
| 09152021_Varenicline B.No_VW0020520 | Tartrate API | 33.196 | 558 | 3.1 % |
| 09152021_Varenicline B.No_VW0020520 | Tartrate API | 33.487 | 487 | 2.7 % |
| 09152021_Varenicline B.No_VW0020520 | Tartrate API | 34.537 | 1349 | 7.4 % |
| 09152021_Varenicline B.No_VW0020520 | Tartrate API | 35.538 | 836 | 4.6 % |
| 09152021_Varenicline B.No_VW0020520 | Tartrate API | 36.855 | 673 | 3.7 % |
| 09152021_Varenicline B.No_VW0020520 | Tartrate API | 37.764 | 523 | 2.9 % |
| 09152021_Varenicline B.No_VW0020520 | Tartrate API | 38.811 | 739 | 4.1 % |
| 09152021_Varenicline B.No_VW0020520 | Tartrate API | 39.972 | 747 | 4.1 % |
| 09152021_Varenicline B.No_VW0020520 | Tartrate API | 40.890 | 458 | 2.5 % |
| 09152021_Varenicline B.No_VW0020520 | Tartrate API | 44.127 | 983 | 5.4 % |
| 09152021_Varenicline B.No_VW0020520 | Tartrate API | 45.947 | 451 | 2.5 % |

Figure 6B

VARENICLINE COMPOUND AND PROCESS OF MANUFACTURE THEREOF

RELATED APPLICATION

This application claims priority to U.S. Provisional Application Ser. No. 63/319,043 filed on Mar. 11, 2022, which is incorporated herein by reference in its entirety to the full extent permitted by law.

TECHNICAL FIELD

The present disclosure relates to the synthesis of varenicline substantially free of impurities. It also relates to pharmaceutical compositions comprising substantially pure varenicline, and to methods of treating nicotine dependency, addiction and withdrawal by administering such compound.

BACKGROUND

Varenicline tartrate salt, 7,8,9,10-tetrahydro-6,10-methano-6H-pyrazino[2,3-h][3]-benzazepine tartrate has the following formula:

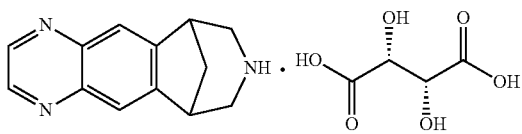 [SMILES: c1cnc2cc3c(cc2n1)C1CNCC3C1 ; O=C(O)[C@H](O)[C@@H](O)C(=O)O]

Varenicline base and various salts thereof are described in U.S. Pat. No. 6,410,550, EP1044189, EP1659114, and EP1866308.

Varenicline L-tartrate and its crystalline forms A, B and C are described in the U.S. Pat. Nos. 6,890,927 and 7,265,119, characterized by XRPD peaks at 6.1, 12.2, 13.0, 14.7, 16.8, 19.4, 21.9, 24.6 (form A); characterized by XRPD peaks at 5.9, 12.8, 14.4, 15.3, 16.9, 17.2, 21.8, 23.8, 25.1 (form B); and characterized by XRPD peaks at 5.9, 11.8, 16.5, 21.2, 23.1, 23.8, 26.5 (form C).

WO2008060487 describes crystalline forms of varenicline base and intermediates thereof. It also describes the polymorphs for varenicline free base (Form A, C, D, and E). EP2260037 describes polymorphs for varenicline free base (Form I, and II), and CN103896943 describes hemi tartrate salt.

Varenicline tartrate was marketed by Pfizer under the trade name of CHANTIX® as a partial agonist selective for certain subtypes of nicotinic receptors and indicated for smoking cessation. However, due to unacceptable level of nitrosamine impurities in CHANTIX®, the product was withdrawn. Accordingly, there is a need for an varenicline active pharmaceutical ingredient ("API") that has an acceptable level of nitrosamine impurities.

SUMMARY

The present disclosure provides an improved process of manufacturing substantially pure varenicline for use as an active pharmaceutical ingredient. In certain embodiments, the process results in varenicline tartrate having less than 100 ppm of N-nitroso-varenicline impurity per 1 mg of varenicline free base, or per 0.5 mg varenicline free base, or less than 50 ppm, or less than 25 ppm, or less than 10 ppm, or less than 5 ppm as measured by the LC-ESI-HRMS Method for the Determination of Varenicline Nitroso-Drug Substance Related Impurity, U.S. FDA, Aug. 6, 2021, https://www.fda.gov/media/151470/download (accessed Feb. 27, 2022) (the "LC-ESI-HRMS Method"); HPLC or LCMS.

The present disclosure further describes a process for preparation of 7,8,9,10-tetrahydro-6,10-methano-6H-pyrazino[2,3-h][3] benzazepine,(2R,3R)-2,3-dihydroxy butanedioate maltodextrin, comprising the steps of:

(a) contacting a reducing agent with 1-(4,5-Dinitro-10-aza-tricyclo[6.3.1.0$^{2,7}$]dodeca-2(7),3,5-trien-10-yl)-2,2,2-trifluoro-ethanone to form 1-(4,5-diamino-10-aza-tricyclo[6.3.1.0$^{2,7}$] dodeca-2(7),3,5-trien-10-yl)-2,2,2-trifluoro-ethanone;

(b) contacting Glyoxal solution in water, a catalyst and a solvent with 1-(4,5-diamino-10-aza-tricyclo[6.3.1.0$^{2,7}$]dodeca-2(7),3,5-trien-10-yl)-2,2,2-trifluoro-ethanone to form 1-(5,8,14-triazatetracyclo[10.3.1.0$^{2,11}$0.0.$^{4,9}$]hexadeca-2(11),3,5,7,9-pentaene)-2,2,2-trifluoro-ethanone;

(c) contacting sodium carbonate solution and methanol with 1-(5,8,14-triazatetracyclo[10.3.1.0$^{2,11}$0.0.$^{4,9}$]hexadeca-2(11),3,5,7,9-pentaene)-2,2,2-trifluoro-ethanone to form crude 7,8,9,10-Tetrahydro-6,10-methano-6H-pyrazino[2,3-h][3]benzazepine;

(d) purifying crude 7,8,9,10-Tetrahydro-6,10-methano-6H-pyrazino[2,3-h][3]benzazepine by acid-base treatment substantially eliminate impurities and to form purified 7,8,9,10-Tetrahydro-6,10-methano-6H-pyrazino[2,3-h][3]benzazepine; and (e) contacting purified 7,8,9,10-Tetrahydro-6,10-methano-6H-pyrazino[2,3-h][3]benzazepine with L-(+) tartaric acid, maltodextrin, methanol and water to form 7,8,9,10-tetrahydro-6,10-methano-6h-pyrazino[2,3-h][3] benzazepine,(2r,3r)-2,3-dihydroxy butanedioate. maltodextrin premix (1:10).

In certain aspects, the process results in the 7,8,9,10-tetrahydro-6,10-methano-6h-pyrazino[2,3-h][3] benzazepine,(2r,3r)-2,3-dihydroxy butanedioate. maltodextrin premix (1:10) being substantially free from nitrosamine impurities, particularly N-nitroso-varenicline.

In one embodiment, crude 7,8,9,10-Tetrahydro-6,10-methano-6H-pyrazino[2,3-h][3]benzazepine is isolated from a reaction mass by a process, comprising the steps of:

(a) cooling and filtering the reaction mass to form a filtrate and a wet cake;

(b) distilling the filtrate to remove methanol;

(c) adding sodium chloride solution to the distilled filtrate;

(d) extracting raw 7,8,9,10-Tetrahydro-6,10-methano-6H-pyrazino[2,3-h][3]benzazepine using methylene chloride and washing with sodium chloride solution;

(e) treating raw 7,8,9,10-Tetrahydro-6,10-methano-6H-pyrazino[2,3-h][3]benzazepine with activated carbon, washing with methylene dichloride and filtering the methylene dichloride through a hyflo bed;

(f) distilling out methylene dichloride followed by co-distilling with tertiary butyl methyl ether to form a semi dried product;

(g) adding tertiary butyl methyl ether to the semi dried product; and (i) isolating crude 7,8,9,10-Tetrahydro-6,10-methano-6H-pyrazino[2,3-h][3]benzazepine.

In another embodiment, the above process results in about 1 mg of the purified 7,8,9,10-tetrahydro-6,10-methano-6h-pyrazino[2,3-h][3] benzazepine,(2r,3r)-2,3-dihydroxy butanedioate. maltodextrin premix (1:10) having less than 25 ppm N-nitroso-varenicline impurity, or about 18.5 ppm or less of N-nitroso-varenicline impurity.

The process of the present disclosure may employ a spray drying step that produces nearly spherical shaped particles, and wherein the 7,8,9,10-tetrahydro-6,10-methano-6h-pyrazino[2,3-h][3] benzazepine,(2r,3r)-2,3-dihydroxy butanedioate is essentially uniformly dispersed in maltodextrin matrix in the particles.

The present disclosure also relates to a method of treating nicotine dependency, addiction and withdrawal in a subject in need thereof, comprising providing a pharmaceutical composition comprising about 0.5 mg to about 2 mg substantially pure varenicline tartrate; and orally administering the composition in one or more daily doses, wherein the subject receives a total of no more than about 37 ng of N-nitroso-varenicline impurity per day. In one embodiment, the composition comprises about 1.7 mg of varenicline tartrate that has less than 25 ppm of N-nitroso-varenicline impurity as measured by the LC-ESI-HRMS Method, HPLC or LCMS. In another embodiment, the composition comprises about 0.85 mg of varenicline tartrate that has less than 25 ppm of N-nitroso-varenicline impurity as measured by the LC-ESI-HRMS Method, HPLC or LCMS.

In another aspect, the composition is orally administered one week before a date set by the subject to attempt to stop smoking. The treatment regimens described herein are effective in the subject to quit smoking between days 8 and 35 of treatment.

In some embodiments, the composition is administered at a dose of about 1 mg varenicline free base twice daily, or wherein the composition is administered in a regimen comprising:

(a) 0.5 mg varenicline free base once daily for days 1-3 of the treatment;

(b) 0.5 mg varenicline free base twice daily for days 4-7 of the treatment; and (c) 1 mg varenicline free base twice daily after day 7 of the treatment.

The present disclosure further relates to a pharmaceutical composition, comprising substantially pure varenicline tartrate and at least one excipient. The composition may comprise about 0.5 mg to about 2 mg varenicline tartrate and is in the form of a tablet or capsule. In one embodiment, the N-nitroso-varenicline impurity is present in an amount of less than 50 ppm per tablet or capsule as measured by the LC-ESI-HRMS Method, HPLC or LCMS.

The pharmaceutical compositions of the present disclosure may contain one or more excipients such as croscarmellose sodium, microcrystalline cellulose, stearic acid, hydroxypropyl cellulose, hypromellose, talc, and titanium dioxide. In some embodiments, the inventive solid dosage forms comprise about 0.5 mg varenicline free base and about 5 ppm or less of N-nitroso-varenicline impurity, or 1 mg varenicline free base and about 5 ppm or less of N-nitroso-varenicline impurity.

Additional embodiments of the present processes, compositions, methods of treatment and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment or aspect. Additional aspects and embodiments are set forth in the following description and claims, particularly when considered in conjunction with the accompanying examples and drawings.

BRIEF DESCRIPTION OF THE DRAWINGS

The foregoing features of embodiments will be more readily understood by reference to the following detailed description, taken with reference to the accompanying drawings, in which:

FIG. 6B is a list of the peaks shown in FIG. 6A.

DETAILED DESCRIPTION

Figure 1:
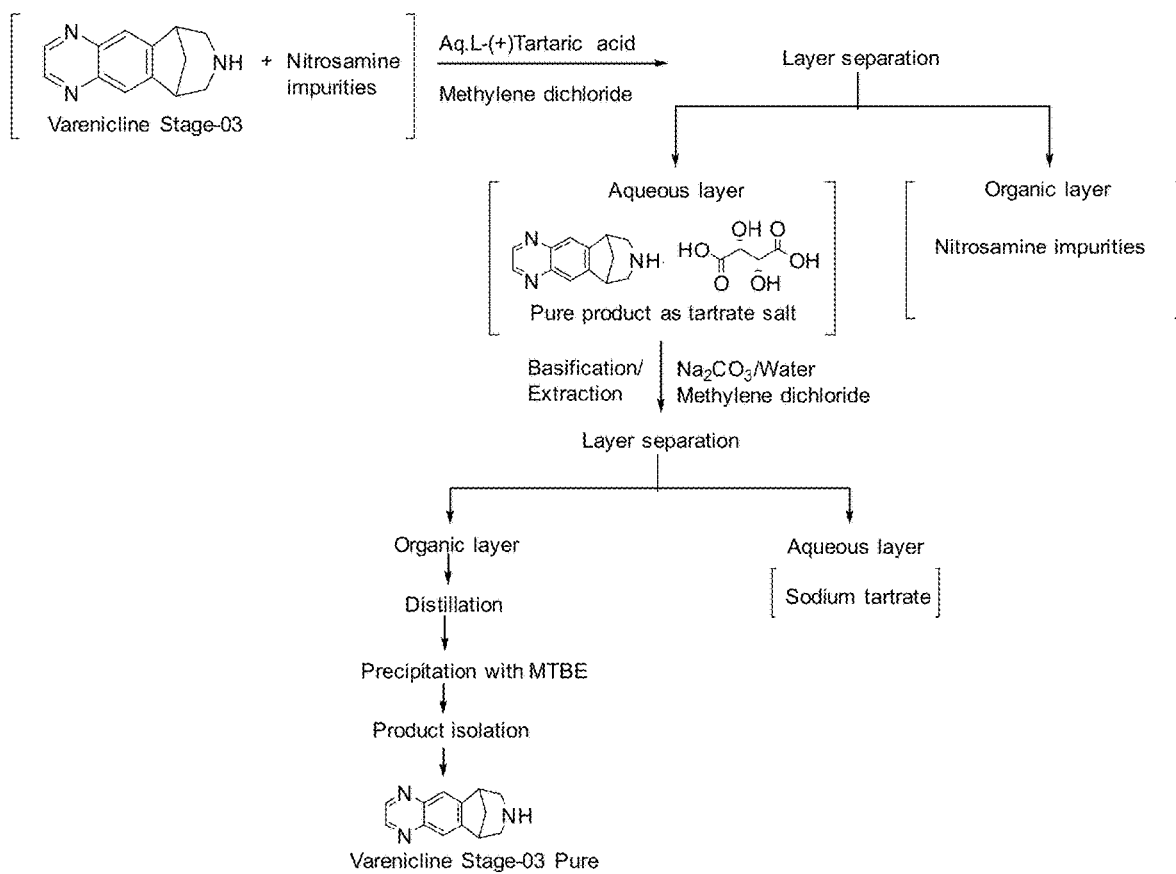
FIG. 1 is a summary of the purification of varenicline free base.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

A. Definitions

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

"Diamide impurity" is Bis (7,8,9,10-tetrahydro-6,10-methano-6H-pyrazino[2,3-h][3]-benzazepine)-amide.

"Diamino Nitrosamine" is 10-nitroso-10-aza-tricyclo[6.3.1.0$^{2,7}$]dodeca-2,4,6-triene-4,5-diamine.

The term "LOD" means limit or level of detection.

The term "LOQ" means limit of quantitation.

"Mononitro Deprotected" is 7-nitro-2,3,4,5-tetrahydro-1H-1,5-methano-3-benzazepine.

"N-Formyl Varenicline" is 6,7,9,10-Tetrahydro-6,10-methano-8H-pyrazino[2,3-h][3]benzazepine-8-carboxaldehyde.

The terms "nitrosamine varenicline impurity," "varenicline nitrosamine impurity" and "N-nitroso-varenicline" are used interchangeably herein.

The terms "nitrosamine impurities" is used for Dinitro Nitrosoamine impurity (4,5-Dinitro-10-nitroso-10-aza-tricyclo[6.3.1.0$^{2,7}$]dodeca-2,4,6-triene); Diamino Nitrosoamine impurity (10-nitroso-10-aza-tricyclo[6.3.1.0$^{2,7}$]dodeca-2,4,6-triene-4,5-diamine); Nitroso Varenicline impurity (7,8,9,10-tetrahydro-8-nitroso-6,10-Methano-6H-pyrazino[2,3-h][3] benzazepine); or a combination thereof.

"N-Methyl Varenicline" is 6,10-methano-6H-pyrazino[2,3-h][3] benzazepine 7,8,9,10-Tetrahydo-8-methyl.

"Optional" or "optionally" means that the subsequently described element, component or circumstance may or may not occur, so that the description includes instances where the element, component, or circumstance occurs and instances where it does not.

The term "premix" as used herein refers to maltodextrin and varenicline tartrate being dissolved in a common solvent (e.g. water) and the resultant solution, spray dried using a spray dryer.

The term "physical mix" or "physical mixture" is a mixture prepared by blending the components (varenicline tartrate and maltodextrin) in a blender. The blending typically takes place by diffusion mechanism.

The term "Powder Transfer System" or "PTS" is a method commonly used for material transfers in chemical processes. Pharmaceutical and chemical plant explosions are industrial disasters with destructive consequences. Charging a reactor with dusty bulk materials is one of the main causes of explosions within the realms of powder handling. Reactors often contain solvents into which the reactants are added. The formation of an explosive atmosphere, which can build up with flammable solvent vapors and a dust/air mixture of the powder, together with a potential source of ignition, have in the past provoked violent explosions, ripping apart whole facilities. Such risks can be effectively mitigated with the use of a PTS (Powder Transfer System®). It is a patented technology by the Dec Group (Dietrich Engineering Consultants). The PTS system is an effective method for transferring dry and moist powders. It transfers powder in dense-phase (plug flow), i.e., at low velocities, thus avoiding too much energy to form electrostatic discharge within the product. Another benefit is that it isolates the receiving vessel during the powder charging process by separating the air from the powder thus keeping the reactor inert. The PTS safely and automatically introduces explosive, toxic or any other kind of powder to pressurized vessels or to reactors that contain hazardous vapors. The system is usually installed directly onto the process equipment to be charged. By using vacuum, the powder gets drawn into the PTS pump body. The flat filtration membrane isolates the powder from entering into the vacuum line. When the chamber is filled, the product is discharged into the vessel by means of pressurized gas, often nitrogen or another inert gas. At the same time, the reverse flow of the gas cleans the membrane each time the product is discharged into the reactor reinstating optimal performance conditions for the next suction cycle. The overpressure in the chamber also prevents vapors that are present in the vessel from entering into the PTS body. The transfer rate is easily controlled by the pneumatic control panel. The Powder Transfer System empties or fills all process equipment including reactors, dryers and centrifuges; transfers all powders regardless of their characteristics (sticky, fine, non-free flowing, hygroscopic, moist, etc.); safely conveys toxic <1 µg/m$^3$ or dust explosive powders <1 mJ; charges directly into closed vessels under vacuum or pressure; prevents dust creation; eliminates oxygen from the powder before entering into the process; and charges in the presence of solvents.

The terms "subject" or "patient" is used interchangeably herein and refers to a human or other mammal.

The term "therapeutically effective amount," as used herein, refers to the amount of varenicline necessary to achieve the desired biological result.

The terms "substantially pure," or "substantially free of impurities" as used herein refers to the varenicline compound, salt or derivative thereof disclosed herein having less than 150 ppm of N-nitroso-varenicline per 1 mg of varenicline free base present as measured by the LC-ESI-HRMS Method for the Determination of Varenicline Nitroso-Drug Substance Related Impurity, U.S. FDA, Aug. 6, 2021, https://www.fda.gov/media/151470/download (accessed Feb. 27, 2022); HPLC; or LCMS.

"Varenicline N-Glucoside" is (8-β-D-Glucopyranosyl-7,8,9,10-tetrahydro-6,10-methano-6H-pyrazino[2,3-h][3]benzazepine).

B. Introduction

The present disclosure relates to the field of synthesizing varenicline and its intermediates. It also relates to varenicline compound that is substantially free of impurities, such as nitrosamines. The disclosure further relates to pharmaceutical compositions comprising varenicline, salt of derivative, and to methods for using such compositions for smoking cessation or other disorders.

C. Process for Making Varenicline

Generally, there are four stages in the synthetic procedure of varenicline tartrate that results in the active pharmaceutical ingredient ("API") that is substantially free of impurities:

Stage I: Preparation of 1-(4,5-diamino-10-aza-tricyclo[6.3.1.0$^{2,7}$]dodeca-2(7),3,5-trien-10-yl)-2,2,2-trifluoro-ethanone ("Diamino")

Stage II: Preparation of 1-(5,8,14-triazatetracyclo[10.3.1.0$^{2,11}$0.0.$^{4,9}$]hexadeca-2(11),3,5,7,9-pentaene)-2,2,2-trifluoro-ethanone ("Quinoxaline")

Stage III: Preparation of purified 7,8,9,10-tetrahydro-6,10-methano-6H-pyrazino[2,3-h][3]benzazepine ("Purified Varenicline Free Base")

Stage IV: Preparation of 7,8,9,10-tetrahydro-6,10-methano-6H-pyrazino[2,3-h][3] benzazepine,(2R,3R)-2,3-dihydroxy butanedioate. Maltodextrin ("Varenicline Tartrate Maltodextrin Premix (1:10)")

Each stage is detailed below.

Stage I: Preparation of 1-(4,5-Diamino-10-Aza Tricyclo[6.3.1.0$^{2,7}$] Dodeca-2(7),3,5-Trien-10-YL)-2,2,2-Trifluoro-Ethanone In one embodiment, 1-(4,5-diamino-10-aza-tricyclo[6.3.1.0$^{2,7}$]dodeca-2(7),3,5-trien-10-yl)-2,2,2-trifluoro-ethanone (Stage I-Diamino) is formed reacting a reducing agent with 1-(4,5-Dinitro-10-aza-tricyclo[6.3.1.0$^{2,7}$]dodeca-2(7),3,5-trien-10-yl)-2,2,2-trifluoro-ethanone (KSM) in a solvent under hydrogen gas pressure. The reaction is conducted under at a temperature from about 20° C. to about 50° C. After a reaction time from about 30 minutes to about 5 hours, the reaction mass is filtered and solvent is distilled off. The product is precipitated by the addition of hexane, isolated by filtration and washed with hexane. The percentage yield [Percentage Yield=(Achieved Yield×100)/Theoretical Yield] is from about 50% to about 100%.

In another embodiment, the reducing agent used in the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is selected from (a) nickel catalysts such as reduced nickel, nickel oxide, Raney nickel and the like; with hydrogen gas or with reagents which can generate hydrogen during the reaction; (b) platinum catalysts such as platinum plate, platinum sponge, platinum black, colloidal platinum, platinum oxide, platinum wire and the like; (c) palladium catalysts such as palladium sponge, palladium black, palladium oxide, palladium on carbon, palladium hydroxide on carbon, colloidal palladium, palladium on barium sulfate, palladium on barium carbonate; (d) metal hydrides such as sodium borohydride, lithium borohydride, lithium aluminum borohydride, substituted form of metal hydrides etc., with or without combination of other regents like trimethyl silyl chloride; (e) sulfides like ammonium sulfide, hydrogen sulfide; (f) metal salts like samarium di-iodide.

In one specific embodiment, the reducing agent used in the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is palladium on carbon with hydrogen gas. In another embodiment, the pressure of the hydrogen gas varies between 1.0 kg/cm$^2$ and 10.0 kg/cm$^2$.

In one embodiment, the temperature during the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is from about 20° C. to about 50° C., from about 25° C. to about 45° C., or from about 30° C. to about 40° C. In one specific embodiment, the temperature during the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C.

In another embodiment, the reaction time for the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is from about 30 minutes to about 5 hours, from about 45 minutes to about 4 hours, from about 1 hour to about 3 hours, or from about 1 hour to about 2 hours. In one specific embodiment, the reaction time for the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is about 30 minutes, about 45 minutes, about 60 minutes, about 75 minutes, about 90 minutes, about 105 minutes, about 120 minutes, about 135 minutes, about 150 minutes, about 165 minutes, about 180 minutes, about 195 minutes, about 210 minutes, about 225 minutes, about 240 minutes, about 255 minutes, about 270 minutes, about 285 minutes, or about 300 minutes. In one embodiment, the solvent in the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is selected from alcohol like methanol, ethanol, isopropyl alcohol and n-propanol; halogenated solvents such as dichloromethane, chloroform and carbon tetrachloride; esters such as ethyl acetate, n-propyl acetate, n-butyl acetate, isobutyl acetate and t-butyl acetate; ether solvents such as tetrahydrofuran and 1,4-dioxane; nitrile solvents such as acetonitrile and propionitrile; dimethylsulfoxide (DMSO); N,N-dimethylformamide (DMF); NN-dimethylacetamide; water; and mixtures thereof.

In one embodiment, the solvent in the synthesis of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is methanol.

In another embodiment, the filtration of the reaction mass of 1-(4,5-diamino-10-aza-tricyclo[6.3.1.0$^{27}$]dodeca-2(7),3,5-trien-10-yl)-2,2,2-trifluoro-ethanone (Stage I-Diamino) is done using gravity filtration, hot filtration, cold filtration, granular media filtration, mechanical filtration, centrifugal filtration or vacuum filtration. In yet another embodiment, the filtration of the reaction mass of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is done using Sparkler filter, leaf filter, ANFD followed by Nutche filtration for final isolation material. In yet another embodiment, the solvent used during the synthesis of 1-(4,5-diamino-10-aza-tricyclo[6.3.1.0$^{27}$]dodeca-2(7),3,5-trien-10-yl)-2,2,2-trifluoro-ethanone (Stage I-Diamino) is removed by distillation, co-distillation, or co-precipitation. In one embodiment, the solvent used is selected from (a) alcohol like methanol, ethanol, isopropyl alcohol, n-propanol; (b) anti-solvents as ether solvents such as diethyl ether, dimethyl ether, diisopropyl ether and, methyl t-butyl ether; (c) hydrocarbon solvents such as toluene, xylene, n-heptane, cyclohexane and n-hexane; (d) water; or (e) mixtures thereof. In one embodiment, the 1-(4,5-diamino-10-aza-tricyclo[6.3.1.0$^{2,7}$]dodeca-2(7),3,5-trien-10-yl)-2,2,2-trifluoro-ethanone (Stage I-Diamino) is precipitated from the reaction mixture using solvents such as ether solvents like diethyl ether, dimethyl ether, diisopropyl ether, methyl t-butyl ether; hydrocarbon solvents such as toluene, xylene, n-heptane, cyclohexane and n-hexane; water; and mixtures thereof. In one specific embodiment, the 1-(4,5-diamino-10-aza-tricyclo[6.3.1.0$^{2,7}$]dodeca-2(7),3,5-trien-10-yl)-2,2,2-trifluoro-ethanone (Stage I-Diamino) is precipitated from the reaction mixture using diisopropyl ether or hexane.

In another embodiment, the percentage yield of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is from about 50% to about 100%, from about 55% to about 99%, from about 60% to about 98%, from about 65% to about 87%, or from about 72.28% to about 96.38%. In one specific embodiment, the percentage yield of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In yet another embodiment, the purity of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is from about 50% to about 100% as measured by column chromatography, paper chromatography, thin-layer chromatography, liquid chromatography (LC), affinity chromatography, ion exchange chromatography, size-exclusion chromatography, reversed-phase chromatography, high performance liquid chromatography (HPLC), liquid chromatography-mass spectrometry (LCMS), titration, nuclear magnetic resonance (NMR) or Liquid Chromatography-High Resolution Mass Spectrometry (LC-ESI-HRMS). In one specific embodiment, purity of 1-(4,5-diamino-10-aza-tricyclo[6.3.1.0$^{2,7}$]dodeca-2(7),3,5-trien-10-yl)-2,2,2-trifluoro-ethanone (Stage I-Diamino) is about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% as measured by column chromatography, paper chromatography, thin-layer chromatography, liquid chromatography, affinity chromatography, ion exchange chromatography, size-exclusion chromatography, reversed-phase chromatography, HPLC, titration, NMR, LCMS or LC-ESI-HRMS.

In one embodiment, 1-(4,5-diamino-10-aza-tricyclo[6.3.1.0$^{2,7}$]dodeca-2(7),3,5-trien-10-yl)-2,2,2-trifluoro-ethanone (Stage I-Diamino) is formed by reacting 10% Palladium on carbon and methanol with 1-(4,5-Dinitro-10-aza-tricyclo[6.3.1.0$^{2,7}$]dodeca-2(7),3,5-trien-10-yl)-2,2,2-trifluoro-ethanone (KSM) under hydrogen gas pressure. The reaction is conducted under at 30-40° C. After 1-2 hours, the reaction mass is filtered and methanol is distilled off. The product is precipitated by the addition of hexane, isolated by filtration and washed with hexane. The percentage yield [Percentage Yield=(Achieved Yield×100)/Theoretical Yield] is about from 72.28 to about 96.38%. A summary of this stage is provided in Table 1.

TABLE 1

Stage-01 in the Process of the Formation of Varenicline Tartrate Maltodextrin Premix (1:10)

| | |
|---|---|
| Scheme | O$_2$N-[structure]-N-C(=O)CF$_3$ → (10% Pd/C, Methanol/H$_2$ gas, Hexane) → H$_2$N-[structure]-N-C(=O)CF$_3$ |
| Reagents | 1. 10% Palladium on carbon<br>2. Methanol<br>3. Hydrogen gas<br>4. Hexane |
| Reaction conditions | Temperature: 30-40° C.<br>Time: 1-2 hours |
| Work-up | Filtration of reaction mass, followed by distillation of methanol. |
| Precipitation & Isolation | Precipitation by the addition of Hexane. Product Isolation by filtration followed by hexane wash. |
| Yield | 0.7-0.82 X |

Stage II: Preparation of 1-(5,8,14-Triazatetracyclo[10.3.1.0$^{2,11}$0.0.$^{4,9}$]Hexadeca-2(11),3,5,7,9-Pentaene)-2,2,2-Trifluoro-Ethanone In another embodiment, Glyoxal solution in water, a catalyst and a solvent are added to 1-(4,5-diamino-10-aza-tricyclo[6.3.1.0$^{2,7}$]dodeca-2(7),3,5-trien-10-yl)-2,2,2-trifluoro-ethanone (Diamino) to form 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline). The reaction is conducted under at a temperature from about 30° C. to about 80° C. After a reaction time from about 30 minutes to about 5 hours, the product is extracted. The product is then precipitated, filtered and washed with a liquid. The product is then purified. The percentage yield is from about 30% to about 80%.

In one specific embodiment, the catalyst used in the synthesis of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is sodium bisulfate, ion exchange resin like Amberlite IRA 67 and similar resins, or mixtures thereof.

In one embodiment, the temperature during the synthesis of 1-(5,8,14-triazatetracyclo[10.3.1.0$^{2,11}$0.0.$^{4,9}$]hexadeca-2

(11),3,5,7,9-pentaene)-2,2,2-trifluoro-ethanone (Stage II-Quinoxaline) is from about 30° C. to about 80° C., from about 35° C. to about 75° C., from about 40° C. to about 70° C., from about 45° C. to about 65° C., or from about 55° C. to about 60° C. In one specific embodiment, the temperature during the synthesis of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is about 30° C., about 35° C., about 40° C., about 45° C., about 50° C., about 51° C., about 51° C., about 53° C., about 54° C., about 55° C., about 56° C., about 57° C., about 58° C., about 59° C., about 60° C., about 61° C., about 62° C., about 63° C., about 64° C., about 65° C., about 70° C., about 75° C., or about 80° C.

In another embodiment, the reaction time for the synthesis of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is from about 30 minutes to about 5 hours, from about 1 hour to about 4 hours, or from about 2 hour to about 3 hours. In one specific embodiment, the reaction time for the synthesis of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is about 30 minutes, about 45 minutes, about 60 minutes, about 75 minutes, about 90 minutes, about 105 minutes, about 120 minutes, about 135 minutes, about 150 minutes, about 165 minutes, about 180 minutes, about 195 minutes, about 210 minutes, about 225 minutes, about 240 minutes, about 255 minutes, about 270 minutes, about 285 minutes, or about 300 minutes.

In yet another embodiment, the pH during the synthesis of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is from about 8.0 to about 14.0.

The cyclization reaction in the synthesis of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is carried out in a solvent selected from water or other aqueous polar solvents such as aqueous mixture of methanol, ethanol, isopropyl alcohol, tetrahydrofuran, dioxane, tetrahydrofuran, dimethylformamide and dimethylsulfoxide at a temperature of about 10° C. to about 100° C.

In another embodiment, the precipitation of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is done using water, ketones like acetone, and other water miscible solvents.

In yet another embodiment, after precipitation, 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is washed with water to remove inorganic materials from the product, and then with non-polar organic solvents such as hydrocarbons to remove water and other impurities.

In one embodiment, 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is purified by recrystallization using an alcohol like methanol, ethanol and isopropyl alcohol; or other organic solvent like ether and hydrocarbon.

In another embodiment, the percentage yield of 1-(5,8,14-triazatetracyclo[10.3.1.0$^{2,11}$.0$^{4,9}$]hexadeca-2(11),3,5,7,9-pentaene)-2,2,2-trifluoro-ethanone (Stage II-Quinoxaline) is from about 30% to about 100%, from about 35% to about 90%, from about 40% to about 80%, or from about 46% to about 70%. In one specific embodiment, the percentage yield of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is about 30%, about 35%, about 40%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 75%, about 80%, about 90%, about 95%, or about 100%.

In yet another embodiment, the purity of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is from about 50% to about 100% as measured by HPLC, LCMS, titration, NMR, column chromatography, paper chromatography, thin-layer chromatography, liquid chromatography, affinity chromatography, ion exchange chromatography, size-exclusion chromatography, reversed-phase chromatography, or LC-ESI-HRMS. In one specific embodiment, purity of 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline) is about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% as measured by HPLC, LCMS, titration, NMR, column chromatography, paper chromatography, thin-layer chromatography, liquid chromatography, affinity chromatography, ion exchange chromatography, size-exclusion chromatography, reversed-phase chromatography, or LC-ESI-HRMS.

In another embodiment, Glyoxal 40% solution in water, sodium bisulfate and methanol are added to 1-(4,5-diamino-10-aza-tricyclo[6.3.1.0$^{2,7}$]dodeca-2(7),3,5-trien-10-yl)-2,2,2-trifluoro-ethanone (Diamino) to form 1-(5,8,14-triazatetracyclo[10.3.1.0$^{2,11}$0.0.$^{4,9}$]hexadeca-2(11),3,5,7,9-pentaene)-2,2,2-trifluoro-ethanone (Stage II-Quinoxaline). The reaction is conducted under at 55-60° C. After 2-3 hours, water is added to the reaction mass. The reaction mass is then filtered and washed with water. The product is recrystallized using methanol. The percentage yield [percentage yield=(Achieved Yield×100)/Theoretical Yield] is from about 46.29% to about 69.44%. A summary of this stage is provided in Table 2.

TABLE 2

Stage-02 in the Process of the Formation of Varenicline Tartrate
Maltodextrin Premix (1:10)

| Scheme | H$_2$N-[structure]-N-CF$_3$ →aq. Glyoxal.2NaHSO$_3$ / Methanol/water→ N-[structure]-N-CF$_3$ |
|---|---|
| Reagents | 1. Glyoxal 40% solution in water<br>2. Sodium bisulfite<br>3. Methanol<br>4. Water |

TABLE 2-continued

Stage-02 in the Process of the Formation of Varenicline Tartrate
Maltodextrin Premix (1:10)

| | |
|---|---|
| Reaction conditions | Temperature: 55-60° C.<br>Time: 2-3 hours |
| Work-up | Addition of water to the reaction mass |
| Precipitation & Isolation | Filtration followed by water wash |
| Purification | Recrystallization using methanol. No second crop isolation |
| Yield | 0.7-0.9 X |

Stage III: Preparation of Purified 7, 8,9,10-Tetrahydro-6,10-Methano-6H-Pyrazino[2,3-H][3]Benzazepine In yet another embodiment, sodium carbonate solution and methanol are added to 1-(5,8,14-triazatetracyclo [10.3.1.0$^{2,11}$0.0.$^{4,9}$]hexadeca-2(11),3,5,7,9-pentaene)-2,2,2-trifluoro-ethanone (Stage II-Quinoxaline) to form crude 7,8,9,10-Tetrahydro-6,10-methano-6H-pyrazino[2,3-h][3]benzazepine (crude Stage III-Varenicline Free Base). The reaction is conducted at 50-90° C. After a reaction time from about 1 hour to 5 hours, the reaction mass is cooled and filtered. The filtrate is then distilled. Sodium chloride solution is added and the product is extracted with an extraction agent and washed with sodium chloride solution. Sodium chloride is used for saturation purposes. Other non-reactive water soluble inorganic salts can be used for saturation of water. The product is then treated with activated carbon, washed with methylene dichloride and the methylene dichloride is filtered through a hyflo bed. The solvent (methylene dichloride) is distilled out. A co-distillation is next performed. The product (Semi Dried Material A or raw) is then precipitated and filtered off.

In one specific embodiment, crude 7,8,9,10-Tetrahydro-6,10-methano-6H-pyrazino[2,3-h][3]benzazepine (crude Stage III-Varenicline Free Base) is purified by acid-base treatment to remove nitrosamine impurities. The Semi Dried Material A (crude Stage III-Varenicline Free Base) is dissolved in methylene chloride and then an acid is added for salt formation. The organic layer is washed and the product is extracted from the aqueous layer. The solvent is distilled and then co-distilled. The Percentage Yield is about from 10% to about 100%.

In one embodiment, the temperature during the synthesis of crude 7,8,9,10-Tetrahydro-6,10-methano-6H-pyrazino[2,3-h][3]benzazepine (crude Stage III-Varenicline Free Base) is from about 50° C. to about 90° C., from about 55° C. to about 80° C., from about 60° C. to about 75° C., or from about 64° C. to about 70° C. In one specific embodiment, the temperature during the synthesis of crude 7,8,9,10-Tetrahydro-6,10-methano-6H-pyrazino[2,3-h][3]benzazepine (crude Stage III-Varenicline Free Base) is about 50° C., about 55° C., about 60° C., about 61° C., about 62° C., about 63° C., about 64° C., about 65° C., about 66° C., about 67° C., about 68° C., about 69° C., about 70° C., about 75° C., about 80° C., about 85° C., or about 90° C.

In another embodiment, the reaction time for the synthesis of crude 7,8,9,10-Tetrahydro-6,10-methano-6H-pyrazino[2,3-h][3]benzazepine (crude Stage III-Varenicline Free Base) is from about 30 minutes to about 5 hours, from about 1 hour to about 4 hours, or from about 2 hour to about 3 hours. In one specific embodiment, the reaction time for the synthesis of crude 7,8,9,10-Tetrahydro-6,10-methano-6H-pyrazino[2,3-h][3]benzazepine (crude Stage III-Varenicline Free Base) is about 30 minutes, about 45 minutes, about 60 minutes, about 75 minutes, about 90 minutes, about 105 minutes, about 120 minutes, about 135 minutes, about 150 minutes, about 165 minutes, about 180 minutes, about 195 minutes, about 210 minutes, about 225 minutes, about 240 minutes, about 255 minutes, about 270 minutes, about 285 minutes, or about 300 minutes.

In yet another embodiment, the pH during the synthesis of crude 7,8,9,10-Tetrahydro-6,10-methano-6H-pyrazino[2,3-h][3]benzazepine (crude Stage III-Varenicline Free Base) is from about 8.0 to 14.0.

In one embodiment, the extraction agent used to extract crude 7,8,9,10-Tetrahydro-6,10-methano-6H-pyrazino[2,3-h][3]benzazepine (crude Stage III-Varenicline Free Base) is a chlorinated solvent such as methylene chloride or chloroform.

In another embodiment, the precipitation of crude 7,8,9,10-Tetrahydro-6,10-methano-6H-pyrazino[2,3-h][3]benzazepine (crude Stage III-Varenicline Free Base) is done using (a) higher alcohol (C3 and above) like isopropyl alcohol, n-propanol; (b) anti-solvents as ether solvents such as diethyl ether, dimethyl ether, diisopropyl ether, methyl t-butyl ether, tetrahydrofuran and 1,4-dioxane; (c) hydrocarbon solvents such as toluene, xylene, n-heptane, cyclohexane, hexanes and n-hexane; (d) esters such as ethyl acetate, n-propyl acetate, n-butyl acetate, isobutyl acetate and t-butyl acetate; or (e) ketone such as acetone, ethyl methyl ketone methyl isobutyl ketone and mixture of ketone with water.

In one embodiment, crude 7,8,9,10-Tetrahydro-6,10-methano-6H-pyrazino[2,3-h][3]benzazepine (crude Stage III-Varenicline Free Base) is purified to remove impurities.

A total of 17 impurities are controlled in the Varenicline Free base (Stage III) synthetic process. These impurities are process related impurities. Among these process related impurities, some of the impurities are identified as potential Genotoxic Impurities and controlled with the limit of NMT 0.0426% w/w. All other varenicline-related compounds are controlled with the limit of not more than (NMT) 0.15% as per ICH Q3A.

In one specific embodiment, the crude 7,8,9,10-Tetrahydro-6,10-methano-6H-pyrazino[2,3-h][3]benzazepine (crude Stage III-Varenicline Free Base) is purified to substantially remove varenicline nitrosamine impurities, process-related impurities, or a combination thereof.

In another specific embodiment, crude 7,8,9,10-Tetrahydro-6,10-methano-6H-pyrazino[2,3-h][3]benzazepine (crude Stage III-Varenicline Free Base) is purified by (a) acid-base treatment using organic and inorganic acids having pKa between 2.0 and 6.0 such as tartaric acid, succinic acid, maleic acid, fumeric acid, etc. (b) recrystallization using various solvents, (c) chromatography purification techniques like column chromatography, preparative HPLC and other equivalent techniques; or (d) reduction/hydrogenation to remove nitrosamine impurities.

In one embodiment, the acid used in acid-base treatment of crude 7,8,9,10-Tetrahydro-6,10-methano-6H-pyrazino[2,3-h][3]benzazepine (crude Stage III-Varenicline Free Base) is any acid or organic acid. In one specific embodiment, the acid used in acid-base treatment of crude 7,8,9,10-Tetrahydro-6,10-methano-6H-pyrazino[2,3-h][3]benzazepine (crude Stage III-Varenicline Free Base) is L(+) Tartaric acid, succinic acid, citric acid, maleic acid, or a combination thereof.

In one specific embodiment, the purification of crude 7,8,9,10-Tetrahydro-6,10-methano-6H-pyrazino[2,3-h][3] benzazepine (crude Stage III-Varenicline Free Base) results in the elimination of nitrosamine impurities. In another embodiment, the purification of crude 7,8,9,10-Tetrahydro-6,10-methano-6H-pyrazino[2,3-h][3]benzazepine (crude Stage III-Varenicline Free Base) results in the elimination of 100%, 99.9%, 99.8%, 99.7%, 99.6%, 99.5%, 99.4%, 99.3%, 99.2%, 99.1%, 99.0%, 98%, 97%, 96%, or 95% of nitrosamine impurities to form purified 7,8,9,10-Tetrahydro-6,10-methano-6H-pyrazino[2,3-h][3]benzazepine (Stage III-Varenicline Free Base).

In another embodiment, the percentage yield of purified 7,8,9,10-Tetrahydro-6,10-methano-6H-pyrazino[2,3-h][3]benzazepine (Stage III-Varenicline Free Base) is from about 10% to about 100%, from about 20% to about 90%, from about 28.98 to about 86.95%, from about 40% to about 80%, or from about 50% to about 70%. In one specific embodiment, the percentage yield of purified 7,8,9,10-Tetrahydro-6,10-methano-6H-pyrazino[2,3-h][3]benzazepine (Stage III-Varenicline Free Base) is about 10%, about 20%, about 29%, about 30%, about 35%, about 40%, about 45%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 75%, about 80%, about 87%, about 90%, about 95%, or about 100%.

In yet another embodiment, purified 17,8,9,10-Tetrahydro-6,10-methano-6H-pyrazino[2,3-h][3]benzazepine (Stage III-Varenicline Free Base) is from about 50% to about 100% pure as measured by HPLC, titration, NMR, LCMS, column chromatography, paper chromatography, thin-layer chromatography, liquid chromatography, affinity chromatography, ion exchange chromatography, size-exclusion chromatography, reversed-phase chromatography, or LC-ESI-HRMS. In one specific embodiment, purified 7,8,9,10-Tetrahydro-6,10-methano-6H-pyrazino[2,3-h][3]benzazepine (Stage III-Varenicline Free Base) is about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% pure as measured by HPLC, titration, NMR, LCMS, column chromatography, paper chromatography, thin-layer chromatography, liquid chromatography, affinity chromatography, ion exchange chromatography, size-exclusion chromatography, reversed-phase chromatography, or LC-ESI-HRMS. In yet another specific embodiment, purified 7,8,9,10-Tetrahydro-6,10-methano-6H-pyrazino[2,3-h][3]benzazepine (Stage III-Varenicline Free Base) is at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9% pure as measured by HPLC, LCMS, column chromatography, paper chromatography, thin-layer chromatography, liquid chromatography, affinity chromatography, ion exchange chromatography, size-exclusion chromatography, reversed-phase chromatography, titration, NMR, or LC-ESI-HRMS.

In one specific embodiment, sodium carbonate solution and methanol are added to 1-(5,8,14-triazatetracyclo [10.3.1.0$^{2,11}$0.0.$^{4,9}$]hexadeca-2(11),3,5,7,9-pentaene)-2,2,2-trifluoro-ethanone (Stage II-Quinoxaline) to form crude 7,8,9,10-Tetrahydro-6,10-methano-6H-pyrazino[2,3-h][3] benzazepine (crude Stage III-Varenicline Free Base). The reaction is conducted at 64-70° C. After 3 hours, the reaction mass is cooled and filtered. The filtrate is then distilled. Sodium chloride solution is added and the product is extracted with methylene chloride and washed with sodium chloride solution. The product is then treated with activated carbon, washed with methylene dichloride and the methylene dichloride is filtered through a hyflo bed. The solvent (methylene dichloride) is distilled out. A co-distillation with tertiary butyl methyl ether is next performed. The product (Semi Dried Material A) is precipitated by the addition of tertiary butyl methyl ether and filtered off.

In another specific embodiment, crude 7,8,9,10-Tetrahydro-6,10-methano-6H-pyrazino[2,3-h][3]benzazepine (crude Stage III-Varenicline Free Base) is purified. The reagents used in the purification process are: sodium chloride, and tertiary Butyl Methyl ether. The crude 7,8,9,10-Tetrahydro-6,10-methano-6H-pyrazino[2,3-h][3]benzazepine is purified by acid-base treatment to remove nitrosamine impurities. The crude 7,8,9,10-Tetrahydro-6,10-methano-6H-pyrazino[2,3-h][3]benzazepine is dissolved in methylene chloride and then L (+) Tartaric acid solution is added for salt formation. The solution is stirred and allowed to settle for layer separation. The aqueous layer is washed with sodium carbonate solution and the product is extracted from the aqueous layer with methylene dichloride. Sodium chloride solution is then added to the organic layer that contains the product and the bottom organic layer is separated. Methylene dichloride is distilled out of the organic layer. This step is followed by co-distillation with tertiary butyl methyl ether. The product (purified 7,8,9,10-Tetrahydro-6,10-methano-6H-pyrazino[2,3-h][3]benzazepine) is precipitated by the addition of tertiary butyl methyl ether and is isolation by filtration followed by tertiary butyl methyl ether washing. The Percentage Yield is about from 28.98 to about 86.95%. A summary of the purification of the Varenicline Fee Base is provided in Table 3 and a summary of the purification of Varenicline Free Base is provided in FIG. 1.

TABLE 3

Stage-03 in the Process of the Formation of Varenicline Tartrate
Maltodextrin Premix (1:10)

Scheme

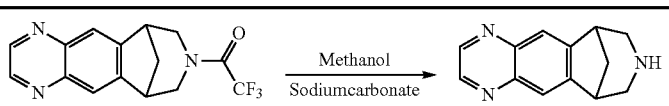

Reagents
1. Sodium carbonate
2. Methanol
3. Methylene dichloride
4. Tertiary Butyl Methyl ether TABLE 3-continued Stage-03 in the Process of the Formation of Varenicline Tartrate Maltodextrin Premix (1:10)

| | |
|---|---|
| | 5. Purified water<br>6. Sodium chloride<br>7. Activated carbon<br>8. Hyflo |
| Reaction conditions | Temperature: 64-70° C.<br>Time: 3 hours |
| Work-up | Cooling & filtration followed by distillation of filtrate. Addition of sodium chloride solution, extraction with methylene chloride followed by sodium chloride solution washing and then activated carbon treatment, solvent distillation followed by co-distillation with Tertiary Butyl Methyl ether |
| Precipitation & Isolation ether. | Precipitation by the addition of Tertiary Butyl Methyl ether.<br>Product isolation by filtration followed by Tertiary Butyl Methyl |

Purification-For removal of Nitrosamine Impurities

| | |
|---|---|
| Scheme | 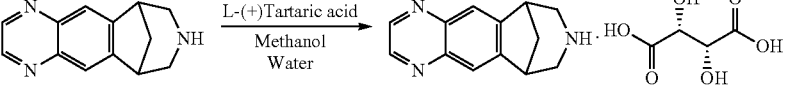 |
| Reagents | 1. Methylene dichloride<br>2. Sodium chloride<br>3. L(+)Tartaric acid<br>4. Purified water<br>5. Sodium carbonate<br>6. Tertiary Butyl Methyl ether |
| Work-up | Purification by acid-base treatment to remove nitrosamine impurities:<br>Process:<br>Semi dried material dissolved in methylene chloride and then add L (+) Tartaric acid solution. Stirring settling and layer separation. Wash the organic layer with sodium carbonate solution. Extract the product from aqueous layer with methylene chloride. Solvent distillation followed by co-distillation with Tertiary Butyl Methyl ether. |
| Precipitation & Isolation | Precipitation by the addition of Tertiary Butyl Methyl ether.<br>Product isolation by filtration followed by Tertiary Butyl Methyl ether. |
| Yield | 0.2-0.60 X |

Stage IV: Preparation of 7,8,9,10-Tetrahydro-6,10-Methano-6H-Pyrazino[2,3-H][3] Benzazepine,(2R, 3R)-2,3-Dihydroxy Butanedioate. Maltodextrin In one embodiment, Varenicline Tartrate Maltodextrin Premix (1:10) is formed by mixing purified 7,8,9,10-Tetrahydro-6,10-methano-6H-pyrazino[2,3-h][3]benzazepine with L-(+) tartaric acid, maltodextrin, methanol and water. The mixture is maintained at a temperature from about 20° C. to about 50° C. After 30 minutes, the product is filtered off, precipitated and isolated. The percentage yield is from about 20% to about 100%.

In one embodiment, 7,8,9,10-tetrahydro-6,10-methano-6h-pyrazino[2,3-h][3] benzazepine,(2r,3r)-2,3-dihydroxy butanedioate and maltodextrin are mixed in a weight/weight ratio of 1:10 (i.e. varenicline tartrate 1× and maltodextrin 10×).

In another embodiment, the mixture in Stage IV is maintained at a temperature from about 20° C. to about 50° C., from about 25° C. to about 45° C., or from about 25° C. to about 35° C. In one specific embodiment, the mixture is maintained at a temperature of about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C.

In yet another embodiment, the product in Stage IV is filtered off using micro-filtration, using a cartridge filter, or using a candle filter.

In one embodiment, the percentage yield of Varenicline Tartrate Maltodextrin Premix (1:10) is from about 20% to about 100%, from about 30% to about 90%, from about 43% to about 96%, from about 40% to about 80%, or from about 50% to about 70%. In one specific embodiment, the percentage yield of Varenicline Tartrate Maltodextrin Premix (1:10) is about 10%, about 20%, about 30%, about 35%, about 40%, about 42%, about 43%, about 45%, about 50%, about 55%, about 60%, about 65%, about 70%, about 75%, about 80%, about 85%, about 90%, about 95%, about 96%, or about 100%.

In another embodiment, Varenicline Tartrate Maltodextrin Premix (1:10) is isolated by spray drying. In yet another embodiment, the duration of the spray drying operation is from about 1 hour to about 30 hours, from about 3 hours to about 27 hours, from about 6 hours to about 24 hours, from about 9 hours to about 21 hours, from about 10 hours to about 18 hours, or from about 11 hours to about 14 hours. In one specific embodiment, the duration of the spray drying operation is about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20, about 25 hours, or about 30 hours.

In yet another embodiment, the temperature during the spray drying operation is from about 20° C. to about 50° C., from about 25° C. to about 45° C., or from about 30° C. to about 40° C. In one specific embodiment, the temperature during the spray drying operation is about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C.

In one embodiment, the inlet temperature of the spray dryer used during the spray drying operation is from about 100° C. to about 180° C., from about 105° C. to about 170° C., from about 110° C. to about 160° C., from about 120° C. to about 150° C., or from about 115° C. to about 150° C. In one specific embodiment, the inlet temperature of the spray dryer used during the spray drying operation is about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., or about 180° C.

In one embodiment, the ID Blower (Induced Draft Fan Blower) flow rate of the spray dryer during the spray drying operation is from about 500 $NM^3/hr$ to about 1000 $NM^3/hr$, from about 600 $NM^3/hr$ to about 900 $NM^3/hr$, or from about 700 $NM^3/hr$ to about 800 $NM^3/hr$. In one specific embodiment, the ID Blower flow rate of the spray dryer during the spray drying operation is about 500 $NM^3/hr$, about 550 $NM^3/hr$, about 600 $NM^3/hr$, about 650 $NM^3/hr$, about 700 $NM^3/hr$, about 750 $NM^3/hr$, about 800 $NM^3/hr$, about 850 $NM^3/hr$, about 900 $NM^3/hr$, about 950 $NM^3/hr$, or about 1000 $NM^3/hr$.

In one embodiment, the FD Blower (Forced Draft Fan Blower) flow rate of the spray dryer during the spray drying operation is from about 100 $NM^3/hr$ to about 700 $NM^3/hr$, from about 200 $NM^3/hr$ to about 600 $NM^3/hr$, or from about 300 $NM^3/hr$ to about 500 $NM^3/hr$. In one specific embodiment, the FD Blower flow rate of the spray dryer during the spray drying operation is about 100 $NM^3/hr$, about 150 $NM^3/hr$, about 200 $NM^3/hr$, about 250 $NM^3/hr$, about 300 $NM^3/hr$, about 350 $NM^3/hr$, about 400 $NM^3/hr$, about 450 $NM^3/hr$, about 500 $NM^3/hr$, about 550 $NM^3/hr$, about 600 $NM^3/hr$, about 650 $NM^3/hr$, or about 700 $NM^3/hr$.

The ID Blower and FD Blower are part of spray dryer and used to circulate/create positive air pressure in the system.

In another embodiment, the atomization pressure of the spray dryer during the spray drying operation is from about 1 $kg/cm^2$ to about 10 $kg/cm^2$, from about 1.5 $kg/cm^2$ to about 8 $kg/cm^2$, from about 2 $kg/cm^2$ to about 6 $kg/cm^2$, or from about 3 $kg/cm^2$ to about 4.2 $kg/cm^2$. In one specific embodiment, the atomization pressure of the spray dryer during the spray drying operation is about 1 $kg/cm^2$, about 1.5 $kg/cm^2$, about 2 $kg/cm^2$, about 2.5 $kg/cm^2$, about 3 $kg/cm^2$, about 3.5 $kg/cm^2$, about 4 $kg/cm^2$, about 4.2 $kg/cm^2$, about 4.5 $kg/cm^2$, about 5 $kg/cm^2$, about 5.5 $kg/cm^2$, about 6 $kg/cm^2$, about 6.5 $kg/cm^2$, about 7 $kg/cm^2$, about 7.5 $kg/cm^2$, about 8 $kg/cm^2$, about 8.5 $kg/cm^2$, about 9 $kg/cm^2$, about 9.5 $kg/cm^2$, or about 10 $kg/cm^2$.

In yet another embodiment, the feed flow rate of the spray dryer during the spray drying operation is from about 10 ml/min to about 120 ml/min, from about 20 ml/min to about 100 ml/min or from about 30 ml/min to about 90 ml/min. In one specific embodiment, the feed flow rate of the spray dryer during the spray drying operation is about 10 ml/min, about 20 ml/min, about 30 ml/min, about 40 ml/min, about 50 ml/min, about 60 ml/min. about 70 ml/min, about 80 ml/min, about 90 ml/min, about 100 ml/min, about 11 ml/min, or about 120 ml/min.

In another embodiment, the spray dried Varenicline Tartrate Maltodextrin Premix (1:10) has a $D_{90}$ particle size of less than or equal to 500 micron, less than or equal to 400 micron, less than or equal to 300 micron, less than or equal to 200 micron, less than or equal to 100 micron, or less than or equal to 50 micron. In yet another embodiment, the spray dried Varenicline Tartrate Maltodextrin Premix (1:10) has a $D_{90}$ particle size from about 5 micron to about 50 micron, from about 50 micron to about 100 micron, from about 100 micron to about 200 micron, from about 300 micron to about 400 micron, or from about 400 micron to about 500 micron.

In one specific embodiment, Varenicline Tartrate Maltodextrin Premix (1:10) is formed by mixing purified 7,8,9,10-Tetrahydro-6,10-methano-6H-pyrazino[2,3-h][3]benzazepine with L-(+) tartaric acid, maltodextrin, methanol and water. The mixture is maintained at 30±3° C. After 30 minutes, the product is filtered off using micro filtration, precipitated and isolated using spray drying. The percentage yield is from about 42.78 to about 96.25%. A summary of this stage of the synthetic procedure is provided in Table 4.

TABLE 4

Stage-04 in the Process of the Formation of Varenicline Tartrate Maltodextrin Premix (1:10)

Scheme

Reagents
1. L-(+) tartaric acid
2. Maltodextrin
3. Methanol
4. Water

TABLE 4-continued

Stage-04 in the Process of the Formation of Varenicline Tartrate Maltodextrin Premix (1:10)

| | |
|---|---|
| Reaction conditions | Temperature: 30 ± 3° C. |
| | Time: 30 min |
| Work-up | Micron filtration |
| Precipitation & Isolation | Spray drying |
| Yield | 12-18 X |

According to the present disclosure, the level of impurities in the Varenicline Tartrate Maltodextrin Premix (1:10) is determined by HPLC, column chromatography, paper chromatography, thin-layer chromatography, liquid chromatography, affinity chromatography, ion exchange chromatography, size-exclusion chromatography, reversed-phase chromatography, titration, NMR, LCMS, or LC-ESI-HRMS.

In another embodiment, the Varenicline Tartrate Maltodextrin Premix (1:10) has about 50 ppm, about 40 ppm, about 30 ppm, about 25 ppm, about 24 ppm, about 23 ppm, about 22 ppm, about 21 ppm, about 20 ppm, about 19 ppm, about 18.5 ppm, about 17 ppm, about 16 ppm, about 15 ppm, about 14 ppm, about 13 ppm, about 12 ppm, about 11 ppm, about 10 ppm, about 9 ppm, about 8 ppm, about 7 ppm, about 6 ppm, about 5 ppm, about 4 ppm, about 3 ppm, about 2 ppm, about 1 ppm of nitrosamine impurity as determined by an analysis technique. In one embodiment, the analysis technique is HPLC, titration, NMR, LCMS, column chromatography, paper chromatography, thin-layer chromatography, liquid chromatography, affinity chromatography, ion exchange chromatography, size-exclusion chromatography, reversed-phase chromatography, or LC-ESI-HRMS.

In yet another embodiment, the Varenicline Tartrate Maltodextrin Premix (1:10) has less than about 50 ppm, less than about 40 ppm, less than about 30 ppm, less than about 25 ppm, less than about 24 ppm, less than about 23 ppm, less than about 22 ppm, less than about 21 ppm, less than about 20 ppm, less than about 19 ppm, less than about 18.5 ppm, less than about 17 ppm, less than about 16 ppm, less than about 15 ppm, less than about 14 ppm, less than about 13 ppm, less than about 12 ppm, less than about 11 ppm, less than about 10 ppm, less than about 9 ppm, less than about 8 ppm, less than about 7 ppm, less than about 6 ppm, less than about 5 ppm, less than about 4 ppm, less than about 3 ppm, less than about 2 ppm, less than about 1 ppm of nitrosamine impurity as determined by an analysis technique. In one embodiment, the analysis technique is HPLC, LCMS, column chromatography, paper chromatography, thin-layer chromatography, liquid chromatography, affinity chromatography, ion exchange chromatography, size-exclusion chromatography, reversed-phase chromatography, titration, NMR, or LC-ESI-HRMS.

In another embodiment, the Varenicline Tartrate Maltodextrin Premix (1:10) has about 50 ppm, about 40 ppm, about 30 ppm, about 25 ppm, about 24 ppm, about 23 ppm, about 22 ppm, about 21 ppm, about 20 ppm, about 19 ppm, about 18.5 ppm, about 17 ppm, about 16 ppm, about 15 ppm, about 14 ppm, about 13 ppm, about 12 ppm, about 11 ppm, about 10 ppm, about 9 ppm, about 8 ppm, about 7 ppm, about 6 ppm, about 5 ppm, about 4 ppm, about 3 ppm, about 2 ppm, about 1 ppm of nitrosamine impurity as measured by HPLC, LCMS, column chromatography, paper chromatography, thin-layer chromatography, liquid chromatography, affinity chromatography, ion exchange chromatography, size-exclusion chromatography, reversed-phase chromatography, titration, NMR, or LC-ESI-HRMS.

In yet another embodiment, the Varenicline Tartrate Maltodextrin Premix (1:10) has less than about 50 ppm, less than about 40 ppm, less than about 30 ppm, less than about 25 ppm, less than about 24 ppm, less than about 23 ppm, less than about 22 ppm, less than about 21 ppm, less than about 20 ppm, less than about 19 ppm, less than about 18.5 ppm, less than about 17 ppm, less than about 16 ppm, less than about 15 ppm, less than about 14 ppm, less than about 13 ppm, less than about 12 ppm, less than about 11 ppm, less than about 10 ppm, less than about 9 ppm, less than about 8 ppm, less than about 7 ppm, less than about 6 ppm, less than about 5 ppm, less than about 4 ppm, less than about 3 ppm, less than about 2 ppm, less than about 1 ppm of nitrosamine impurity as measured by HPLC, LCMS, column chromatography, paper chromatography, thin-layer chromatography, liquid chromatography, affinity chromatography, ion exchange chromatography, size-exclusion chromatography, reversed-phase chromatography, titration, NMR, or LC-ESI-HRMS.

D. Varenicline Compound

The varenicline produced by the inventive process described herein can be in the form of L-tartrate salt, D,L-tartrate salt, D-tartrate salt, meso-tartrate salt. Tartaric acid, citric acid, succinic acid, maleic acid, fumeric acid, etc. can be used for the elimination of nitrosamine. The salts are formed in-situ and salts are dissolved in the aqueous phase and the undissolved nitroamine is extracted in an organic solvent to eliminate the nitrosamine impurities. Further the aqueous layer is acidified to obtain pure varenicline base. Further, such salt form may be anhydrous, a hydrate, or a monohydrate. Such forms are suitable for the administration of a varenicline compound to human subjects having less than 150 ppm, less than about 125 ppm, less than about 100 ppm, less than about 75 ppm, less than about 50 ppm, less than about 25 ppm, less than about 20 ppm, less than about 19 ppm, less than about 15 ppm, less than about 10 ppm, or less than about 5 ppm of N-nitroso-varenicline per 1 mg of varenicline free base.

In other embodiments, the varenicline tartrate has about 1 ppm, about 2 ppm, about 3 ppm, about 4 ppm, about 5 ppm, about 6 ppm, about 7 ppm, about 8 ppm, about 9 ppm, or about 10 ppm of N-nitroso-varenicline per 1 mg of varenicline free base.

The processes described herein can be employed to make various forms of substantially pure varenicline API. The L-tartrate salt exists as three possible forms: two anhydrous forms and one hydrate form. Of the two anhydrous forms, Form A and Form B, Form A is the kinetic polymorph, which will convert under appropriate conditions to the thermodynamically favored Form B. The hydrate L-tartrate salt Form C is a monohydrate and is relatively stable under ambient conditions. It will maintain its one equivalent of water under vacuum at moderate temperatures for at least a day (e.g., for 24 hours in a 45° C. vacuum oven), but eventually over time (i.e., 48 hours or more) will lose water and convert to the anhydrous Form B. Form B is the most stable of the polymorphs at low humidity. Accordingly, Form B would appear to be the most appropriate and most stable polymorph of the L-tartrate salts of 5,8,14-triazatetracyclo [10.3.1.02,11.04,9]-hexadeca-2(11),3,5,7,9-pentaene for pharmaceutical formulation use.

E. Impurities

Three nitrosamine impurities could have formed during the manufacturing process of Varenicline Tartrate Maltodextrin premix (1:10) API. Dinitro nitrosamine impurity may have formed during the nitration reaction for the preparation of the 1-(4,5-Dinitro-10-aza-tricyclo [6.3.1.0$^{2,7}$]dodeca-2 (7),3,5-trien-10-yl)-2,2,2-trifluoro-ethanone (KSM). This impurity is a carryover impurity and converts to Diamino nitrosamine impurity in Stage 1 of Varenicline Tartrate Maltodextrin Premix (1:10) synthetic procedure. This Diamino nitrosamine converts to Varenicline nitrosamine impurity during the subsequent stages. Since both Dinitro nitrosamine and Diamino nitrosamine are carryover impurities and convert to Varenicline nitrosamine during the manufacturing process, these dinitro nitroamine and diamino nitrosamine impurities are controlled in Stage 3 and observed 'Not detected' level in Varenicline free base before purification itself.

A total of 17 impurities are controlled in the Varenicline Free base (Stage III) synthetic process. These impurities are process-related impurities. Among these process-related impurities, some of the impurities are identified as potential Genotoxic Impurities and controlled with the limit of NMT 0.0426% w/w. All other varenicline-related compounds are controlled with the limit of NMT 0.15% as per ICH Q3A.

Moreover, six process Related/Degradation impurities are controlled in varenicline tartrate maltodextrin premix API with the limit of NMT 0.15% w/w.

Further, three nitrosamine impurities are controlled each in the premix API with the limit of NMT 5.26 ppm and total nitrosamines are controlled with the limit of NMT 7.24 ppm.

This process is efficient in eliminating the nitrosamine impurities from the API. The nitrosamine impurities are substantially or completely eliminated by converting the varenicline base into varenicline salt with an organic or inorganic acid having a pKa between 2 and 6. Because the absence of basic nitrogen due to the presence of the nitroso group prevents the nitrosamine impurities to form salt of acids, nitrosamine impurity fails to dissolve in the aqueous solution, and could be extracted in an organic solvent. Thus, nitrosamine impurities could be completely removed in this acid-base treatment process.

In one embodiment, the Varenicline Tartrate Maltodextrin Premix (1:10) has not more than about 0.2% w/w, not more than about 0.15% w/w, not more than about 0.1% w/w, not more than about 0.05% w/w, not more than about 0.0438% w/w, not more than about 0.03% w/w, not more than about 0.02% w/w, or not more than about 0.01% w/w of impurities such as those listed in Tables 5 and 6 below, for example, Varenicline KSM, Varenicline Stage-01, Mononitro Protected compound, Metadinitro protected compound, Mononitro deprotected, Impurity-G, Meta dinitro deprotected, Monoamino protected compound, Metadiamino protected compound, Impurity-C, Impurity-F, Impurity-D, Amino nitro protected, Amino nitro de-protected, Varenicline Stage-02, Methyl Varenicline Protected, or Methyl Varenicline as determined by an analysis technique. In one embodiment, the analysis technique is HPLC, LCMS, column chromatography, paper chromatography, thin-layer chromatography, liquid chromatography, affinity chromatography, ion exchange chromatography, size-exclusion chromatography, reversed-phase chromatography, titration, NMR, or LC-ESI-HRMS.

In another embodiment, the Varenicline Tartrate Maltodextrin Premix (1:10) has not more than about 10 ppm, about 9 ppm, about 8 ppm, about 7 ppm, about 6 ppm, about 5.26, about 5 ppm, about 4 ppm, about 3 ppm, about 2 ppm, about 1 ppm of Dinitro Nitrosoamine impurity, Diamino Nitrosoamine impurity, or Nitroso Varenicline impurity as determined by an analysis technique. In one embodiment, the analysis technique is HPLC, LCMS, column chromatography, paper chromatography, thin-layer chromatography, liquid chromatography, affinity chromatography, ion exchange chromatography, size-exclusion chromatography, reversed-phase chromatography, titration, NMR, or LC-ESI-HRMS.

A list of the possible impurities is provided in Tables 5 and 6 below.

TABLE 5

Possible Varenicline Impurities in Varenicline base (Stage 3) and Varenicline Tartrate Maltodextrin premix API (Stage 4)

| S.No | Chemical Name of the Impurity and Testing Method | Structure of the Impurity | Origin | Control |
|---|---|---|---|---|
| | | Process Related Impurity: | | |
| 1 | Varenicline KSM 1-(4,5-Dinitro-10-aza-tricyclo[6.3.1. 0$^{2,7}$]dodeca-2(7),3,5-trien-10-yl)-2,2,2-trifluoro-ethanone (RS Method-I) | 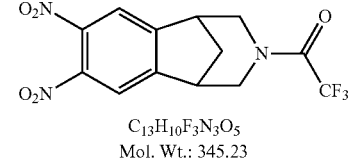 [SMILES: O=C(N1CC2CC(C1)c1cc([N+](=O)[O-])c([N+](=O)[O-])cc12)C(F)(F)F] $C_{13}H_{10}F_3N_3O_5$ Mol. Wt.: 345.23 | Carry over impurity. | This is a potential Genotoxic Impurity (GTI) impurity and is controlled in Stage-03 with a limit 0.0438% w/w. |
| 2 | Varenicline Stage-01 1-(4,5-diamino-10-aza-tricyclo[6.3.1.0 $^{2,7}$] dodeca-2(7),3,5-trien-10-yl)-2,2,2-trifluoro-ethanone (RS Method-I) | 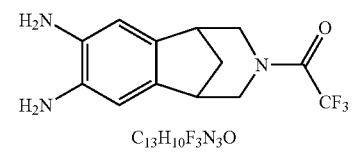 $C_{13}H_{10}F_3N_3O$ Mol. Wt.: 285.26 | Carry over impurity. | This is a potential Genotoxic Impurity (GTI) impurity and is controlled in Stage-03 with a limit 0.0438% w/w. Ref: WO2007/110730 A2 |

TABLE 5-continued

Possible Varenicline Impurities in Varenicline base (Stage 3) and Varenicline Tartrate Maltodextrin premix API (Stage 4)

| S.No | Chemical Name of the Impurity and Testing Method | Structure of the Impurity | Origin | Control |
|---|---|---|---|---|
| 3 | Varenicline Stage-02 1-(5,8,14-Triazatetracyclo [10.3.1.0$^{2,11}$.0$^{4,9}$]hexadeca-2(11), 3,5,7,9-pentaene)-2,2,2-trifluro-ethanone (Quinoxaline) (RS Method-I) | $C_{15}H_{12}F_3N_3O$ Mol. Wt.: 307.27 | Carry over impurity. | This impurity is controlled in Stage-03 with a limit NMT 0.15% w/w. |
| 4 | Mononitro Protected compound: 7-nitro-3-(trifluoroacetyl)-2,3,4,5-tetrahydro-1H-1,5-methano-3-benzazepine (RS Method-II) | $C_{13}H_{11}F_3N_2O_3$ Mol. Wt.: 300.23 | Carry over impurity. | This is a potential Genotoxic Impurity (GTI) impurity and is controlled in Stage-03 with a limit 0.0438% w/w. Ref: WO2007/110730 A2 |
| 5 | Metadinitro protected compound: 6,8-dinitro-2,3,4,5-tetrahydro-1H 1,5-methano-3-benzazepine (RS Method-II) | $C_{13}H_{10}F_3N_3O_5$ Mol. Wt.: 345.23 | Carry over impurity. | This is a potential Genotoxic Impurity (GTI) impurity and is controlled in Stage-03 with a limit 0.0438% w/w. Ref: WO2007/110730 A2 US2013/0030179 A1 |
| 6 | Mononitro deprotected: 7-nitro-2,3,4,5-tetrahydro-1H-1,5-methano-3-benzazepine (RS Method-II) | $C_{11}H_{12}N_2O_2$ Mol. Wt.: 204.23 | Carry over impurity. | This is a potential Genotoxic Impurity (GTI) impurity and is controlled in Stage-03 with a limit 0.0438% w/w. Ref: WO2007/110730 A2 |
| 7 | Impurity-G: 7,8-Dinitro-2,3,4,5-tetrahydro-1H-1,5-methano-3-benzazepine (RS Method-II) | $C_{11}H_{11}N_3O_4$ Mol. Wt.: 249.22 | Carry over impurity. | This is a potential Genotoxic Impurity (GTI) impurity and is controlled in Stage-03 with a limit 0.0438% w/w. Ref: WO2007/110730 A2 US2013/0030179 A1 |
| 8 | Meta dinitro deprotected: 3,5-Dinitro-10-aza-tricyclo[6.3.1.0$^{2,7}$]dodeca-2,4,6-triene (RS Method-II) | $C_{11}H_{11}N_3O_4$ Mol. Wt.: 249.22 | Carry over impurity. | This is a potential Genotoxic Impurity (GTI) impurity and is controlled in Stage-03 with a limit 0.0438% w/w. Ref: WO2007/110730 A2 US2013/0030179 A1 |
| 9 | Monoamino protected compound: 3-(trifluoroacetyl)-2,3,4,5-tetrahydro-1H-1,5-methano-3-benzazepin-7-amine (RS Method-II) | $C_{13}H_{13}F_3N_2O$ Mol. Wt.: 270.25 | Carry over impurity. | This is a potential Genotoxic Impurity (GTI) impurity and is controlled in Stage-03 with a limit 0.0438% w/w. Ref: WO2007/110730 A2 |

TABLE 5-continued

Possible Varenicline Impurities in Varenicline base (Stage 3) and Varenicline Tartrate Maltodextrin premix API (Stage 4)

| S.No | Chemical Name of the Impurity and Testing Method | Structure of the Impurity | Origin | Control |
|---|---|---|---|---|
| 10 | Metadiamino protected compound: 3-(trifluoroacetyl)-2,3,4,5-tetrahydro-1H-1,5-methano-3-benzazepine-6,8-diamine (RS Method-II) | $C_{13}H_{14}F_3N_3O$ Mol. Wt.: 285.26 | Carry over impurity. | This is a potential Genotoxic Impurity (GTI) impurity and is controlled in Stage-03 with a limit 0.0438% w/w. Ref: WO2007/110730 A2 US2013/0030179 A1 |
| 11 | Impurity-C: 2,3,4,5-tetrahydro-1H-1,5-methano-3-benzazepin-7-amine (RS Method-I) | $C_{11}H_{14}N_2$ Mol. Wt.: 174.24 | Carry over impurity. | This is a potential Genotoxic Impurity (GTI) impurity and is controlled in Stage-03 with a limit 0.0438% w/w. Ref: WO2007/110730 A2 |
| 12 | Impurity-F: 7,8-Diamino-2,3,4,5-tetrahydro-1H-1,5-methano-3-benzazepine (RS Method-I) | $C_{11}H_{15}N_3$ Mol. Wt.: 189.26 | Carry over impurity. | This is a potential Genotoxic Impurity (GTI) impurity and is controlled in Stage-03 with a limit 0.0438% w/w. Ref: WO2007/110730 A2 US2013/0030179 A1 |
| 13 | Impurity-D: 2,3,4,5-tetrahydro-1H-1,5-methano-3-benzazepine-6,8-diamine (RS Method-I) | $C_{11}H_{15}N_3$ Mol. Wt.: 189.26 | Carry over impurity. | This is a potential Genotoxic Impurity (GTI) impurity and is controlled in Stage-03 with a limit 0.0438% w/w. Ref: WO2007/110730 A2 US2013/0030179 A1 |
| 14 | Amino nitro protected: 1-(7-Amino-8-nitro-1,2,4,5-tetrahydro-3H,-1,5-methanobenzo [d]azepin-3-yl)-2,2,2-trifluoroethan-1-one. (Controlled in Stage I) | $C_{13}H_{12}F_3N_3O_3$ Mol. Wt.: 315.25 | Carry over impurity. | This is a potential Genotoxic Impurity (GTI) impurity and is controlled in Stage-03 with a limit 0.0438% w/w. Ref: WO2007/110730 A2 |
| 15 | Amino nitro de-protected: 8-nitro-2,3,4,5-tetrahydro-1H-1,5-methanobenzo [d]azepin-7-Amine (Controlled in Stage I) | $C_{11}H_{13}N_3O_2$ Mol. Wt.: 219.24 | Carry over impurity. | This is a potential Genotoxic Impurity (GTI) impurity and is controlled in Stage-01 with a limit 0.0438% w/w. Ref: WO2007/110730 A2 |
| 16 | Methyl Varenicline Protected 2-methyl-7,8,9,10-Tetrahydro-8-(trifluoroacetyl)-6,10-methano-6H-pyrazino[2,3-h][3]benzazepine. (or) 2,2,2-Trifluoro-1-(2-methyl-6,7,9,10-tetrahydro-6,10-methano-8H-pyrazino [2,3-h][3]benzazepin-8-yl)ethanone. | $C_{16}H_{14}F_3N_3O$ Mol. Wt.: 321.30 | Process impurity. | Ref: WO2011/110954 A1 |

TABLE 5-continued

Possible Varenicline Impurities in Varenicline base (Stage 3) and Varenicline Tartrate Maltodextrin premix API (Stage 4)

| S.No | Chemical Name of the Impurity and Testing Method | Structure of the Impurity | Origin | Control |
|---|---|---|---|---|
| 17 | Methyl Varenicline: 2-methyl-7,8,9,10-tetrahydro-6H-6,10-methanoazepino[4,5-g]quinoxaline (RS Method-I) | 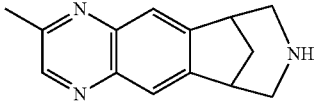<br>$C_{14}H_{15}N_3$<br>Mol. Wt.: 225.29 | Process impurity. | This impurity is controlled in stage-3 with a limit NMT 0.15% w/w.<br>Ref: WO2011/110954 A1 |

Varenicline Tartrate Maltodextrin Premix: Process related/Degradation impurity.

| | | | | |
|---|---|---|---|---|
| 1 | Diamide impurity: Bis (7,8,9,10-tetrahydro-6,10-methano-6H-pyrazino[2,3-h][3]-benzazepine)-amide (RS Method-II) | 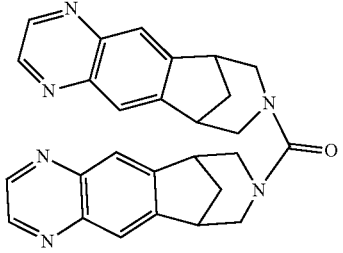<br>$C_{27}H_{24}N_6O$<br>Mol. Wt.: 448.52 | Process impurity. | This impurity is controlled in premix API specification with a limit NMT 0.15% w/w. |
| 2 | Monomethyl Tartrate (Tartaric acid Monomethyl ester) (LCMS-ESI) | 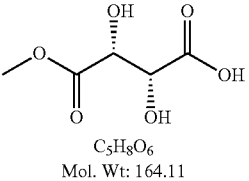<br>$C_5H_8O_6$<br>Mol. Wt: 164.11 | Process related/degradation on impurity. | This impurity is controlled in final premix API specification with a limit NMT 0.15% w/w. |
| 3 | Dimethyl Tartrate (Tartaric acid dimethyl ester) (LCMS-APCI) | 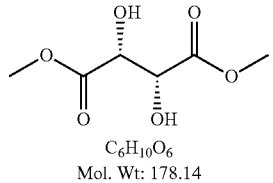<br>$C_6H_{10}O_6$<br>Mol. Wt: 178.14 | Process related/degradation on impurity. | This impurity is controlled in final premix API specification with a limit NMT 0.15% w/w. |
| 4 | N-Methyl Varenicline: 7,8,9,10-tetrahydro-8-methyl-6,10-Methano-6H-pyrazino[2,3-h][3]benzazepine (RS Method-III) | 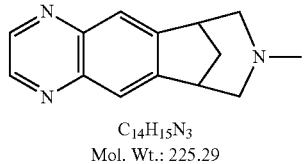 [SMILES: CN1CC2CC(C1)c1cc3nccnc3cc12]<br>$C_{14}H_{15}N_3$<br>Mol. Wt.: 225.29 | Degradation impurity. | Controlled in premix API with a limit of NMT 0.15% w/w. |
| 5 | N-Formyl Varenicline: 6,7,9,10-Tetrahydro-6,10-methano-8H-pyrazino[2,3-h][3]benzazepine-8-carboxaldehyde (RS Method-II) | 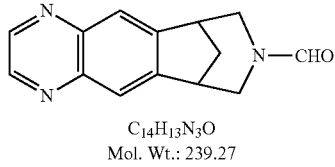 [SMILES: O=CN1CC2CC(C1)c1cc3nccnc3cc12]<br>$C_{14}H_{13}N_3O$<br>Mol. Wt.: 239.27 | Degradation impurity. | Controlled in premix API with a limit of NMT 0.15% w/w. |
| 6 | Varenicline N-Glucoside (RS Method-III) | 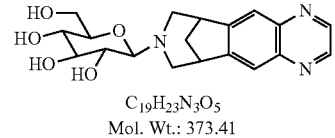 [SMILES: OCC1OC(N2CC3CC(C2)c2cc4nccnc4cc23)C(O)C(O)C1O]<br>$C_{19}H_{23}N_3O_5$<br>Mol. Wt.: 373.41 | Degradation impurity. | Controlled in premix API with a limit of NMT 0.15% w/w. |

TABLE 6

Varenicline Nitrosamine Impurities

| S.No | Chemical Name of the Impurity | Structure of the Impurity | Origin | Common Name of the Impurity |
|---|---|---|---|---|
| 7 | Dinitro Nitrosoamine impurity: 4,5-Dinitro-10-nitroso-10-aza-tricyclo [6.3.1.0$^{2,7}$] dodeca-2,4,6-triene. (LCMS Method-I) | $C_{11}H_{10}N_4O_5$ Mol. Wt.: 278.22 | Carry over impurity from KSM | Controlled final premix API specification with a limit NMT 5.26 ppm. |
| 8 | Diamino Nitrosoamine impurity: 10-nitroso-10-aza-tricyclo[6.3.1.0$^{2,7}$]dodeca-2,4,6-triene-4,5-diamine. (LCMS Method-II) | $C_{11}H_{14}N_4O$ Mol. Wt.: 218.26 | Carry over impurity from stage-1 | Controlled in final premix API specification with a limit NMT 5.26 ppm. |
| 9 | Nitroso Varenicline impurity: 7,8,9,10-tetrahydro-8-nitroso-6,10-Methano-6H-pyrazino[2,3-h][3]benzazepine (LCMS Method-I) | $C_{13}H_{12}N_4O$ Mol. Wt.: 240.26 | Process impurity | Controlled in final premix API specification with a limit NMT 5.26 ppm. |

F. Pharmaceutical Compositions Comprising Varenicline Compound

The substantially pure L-tartrate, the D-tartrate, the D,L-tartrate and the meso-tartrate salts of the present disclosure can be administered via either the oral, transdermal (e.g., patch), intranasal, sublingual, rectal, parenteral or topical routes. Transdermal and oral administration are preferred. These salts may be administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is typically employed.

The tartrate salts can be administered alone or in combination with pharmaceutically acceptable carriers or diluents by any of the several routes previously indicated. More particularly, the active salts can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compound is present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tableting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

In one embodiment, a 0.5 mg varenicline tablet contains about 0.85 mg varenicline tartrate equivalent to about 0.5 mg varenicline free base. In another embodiment, a 1 mg varenicline tablet contains about 1.7 mg equivalent to about 1 mg varenicline free base.

In a specific embodiment, a tablet comprises:
about 0.85 mg substantially pure varenicline tartrate (equivalent to 0.5 mg free base);
about 5-15 mg croscarmellose sodium
about 5-50 mg maltodextrin;
about 100-200 mg microcrystalline cellulose;
about 0.5-2.0 mg stearic acid.

In another specific embodiment, a tablet comprises:
about 1.7 mg substantially pure varenicline tartrate (equivalent to 1 mg free base);
about 5-15 mg croscarmellose sodium
about 5-50 mg maltodextrin;
about 100-200 mg microcrystalline cellulose;
about 0.5-2.0 mg stearic acid.

The tablets can be film-coated with a coating material containing hydroxypropyl cellulose, hypromellose, talc, and titanium dioxide. In another embodiment, the tablets are film-coated with a coating material containing hydroxypropyl cellulose, hypromellose, talc, titanium dioxide, FD&C blue #2/indigo carmine aluminum lake and iron oxide yellow.

In another embodiment, a tablet comprises substantially pure varenicline tartrate, microcrystalline cellulose, anhydrous dibasic calcium phosphate, croscarmellose sodium, colloidal silicon dioxide, magnesium stearate, Opadry® White (for 0.5 mg varenicline free base), Opadry® Blue (for 1 mg varenicline free base), and Opadry® Clear.

G. Methods Of Treatment

The present disclosure further provides a method for treating nicotine dependency, addiction and withdrawal in a subject in need thereof, comprising the administration of a varenicline salt to a human subject having less than 150 ppm, less than about 125 ppm, less than about 100 ppm, less than about 75 ppm, less than about 50 ppm, less than about 25 ppm, less than about 20 ppm, less than about 15 ppm, less than about 10 ppm, or less than about 5 ppm of N-nitroso-varenicline per 1 mg of varenicline free base.

In other embodiments, the varenicline tartrate has about 1 ppm, about 2 ppm, about 3 ppm, about 4 ppm, about 5 ppm, about 6 ppm, about 7 ppm, about 8 ppm, about 9 ppm, or about 10 ppm of N-nitroso-varenicline per 1 mg of varenicline free base.

In another embodiment, there is a method of treatment for nicotine dependency, addiction and withdrawal in a subject in need thereof, comprising the oral administration of a pharmaceutical composition comprising substantially pure varenicline tartrate.

In some embodiments, the varenicline is orally administered one week before the date set by the patient to stop smoking. Alternatively, the patient can begin dosing and then quit smoking between days 8 and 35 of treatment.

In some embodiments, the recommended dose of varenicline free base is 1 mg twice daily following a 1-week titration as detailed in Table 7 below.

TABLE 7

Recommended dose of varenicline

| | |
|---|---|
| Days 1-3: | 0.5 mg free base once daily |
| Days 4-7: | 0.5 mg free base twice daily |
| Day 8-end of treatment: | 1 mg free base twice daily |

Patients are preferably treated with varenicline for 12 weeks. For patients who have successfully stopped smoking at the end of 12 weeks, an additional course of 12 weeks treatment with varenicline is recommended to further increase the likelihood of long-term abstinence.

In some embodiments, the methods disclosed herein reduce smoking by 50% from baseline within the first four weeks, by an additional 50% in the next four weeks, and continue reducing with the goal of reaching complete abstinence by 12 weeks. The present disclosure also relates to a method of treating nicotine dependency, addiction and withdrawal in a subject in need thereof, comprising providing a pharmaceutical composition comprising about 0.5 mg to about 2 mg substantially pure varenicline tartrate; and orally administering the composition in one or more daily doses, wherein the subject receives a total of no more than about 37 ng of N-nitroso-varenicline impurity per day. In one embodiment, the composition comprises about 1.7 mg of varenicline tartrate that has less than 25 ppm of N-nitroso-varenicline impurity as measured by the LC-ESI-HRMS Method; HPLC; or LCMS. In another embodiment, the composition comprises about 0.85 mg of varenicline tartrate that has less than 25 ppm of N-nitroso-varenicline impurity as measured by the LC-ESI-HRMS Method; HPLC; or LCMS.

Alternatively, the composition comprises about 1.7 mg of varenicline tartrate that has less than 19 ppm of N-nitroso-varenicline impurity as measured by the LC-ESI-HRMS Method, HPLC, or LCMS; or the composition comprises about 0.85 mg of varenicline tartrate that has less than 19 ppm of N-nitroso-varenicline impurity as measured by the LC-ESI-HRMS Method, HPLC, or LCMS.

In one embodiment, the compounds, intermediates and pharmaceutical compositions of the present disclosure are used for the treatment of nicotine addiction, inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac, arrhythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, stroke, traumatic brain injury (TBI), obsessive-compulsive disorder, psychosis, Huntington's Chorea, tardive dyskinesia, hyperkinesia, dyslexia, schizophrenia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

In another embodiment, the compounds, intermediates and pharmaceutical compositions of the present disclosure may also be used in combination with an antidepressant such as, for example, a tricyclic antidepressant or a serotonin reuptake inhibiting antidepressant (SRI), in order to treat both the cognitive decline and depression associated with AD, PD, stroke, Huntington's Chorea or traumatic brain injury (TBI): in combination with muscarinic agonists in order to stimulate both central muscarinic and nicotinic receptors for the treatment, for example, of ALS, cognitive dysfunction, age related cognitive decline, AD, PD, stroke, Huntington's Chorea and TBI; in combination with neurotrophic factors such as NGF in order to maximize cholinergic enhancement for the treatment, for example, of ALS, cognitive dysfunction, age related cognitive decline, AD, PD stroke, Huntington's Chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

H. Examples

The following examples are included to demonstrate certain embodiments of the present disclosure. Those of skill in the art should, however, in light of the present disclosure, appreciate that modifications can be made in the specific embodiments that are disclosed and still obtain a like or similar result without departing from the spirit and scope of the invention. Therefore, all matter set forth is to be interpreted as illustrative and not in a limiting sense.

Examples are provided for the preparation of Varenicline Tartrate Maltodextrin premix (1:10) from the KSM, 1-(4,5-Dinitro-10-aza-tricyclo[6.3.1.0$^{2,7}$]dodeca-2(7),3,5-trien-10-yl)-2,2,2-trifluoroethanone. Also Examples are provided for demonstrating the purification of Varenicline base for eliminating nitrosamines and nitrosamine content results in Varenicline base before and after purification.

Example 1

Stage I: Preparation of 1-(4,5-Diamino-10-Aza-Tricyclo[6.3.1.0$^{2,7}$]Dodeca-2(7),3,5-Trien-10-YL)-2,2,2-Trifluoro-Ethanone The following is an illustration of the chemical reaction to produce 1-(4,5-diamino-10-aza-tricyclo[6.3.1.0$^{2,7}$]dodeca-2(7),3,5-trien-10-yl)-2,2,2-trifluoro-ethanone (Diamino) starting from 1-(4,5-Dinitro-10-aza-tricyclo[6.3.1.0$^{2,7}$]dodeca-2(7),3,5-trien-10-yl)-2,2,2-trifluoro-ethanone (KSM). The synthetic procedure is discussed in details below. Throughout this synthetic procedure, X=32.50±2.50 kg of 1-(4,5-Dinitro-10-aza-tricyclo[6.3.1.0$^{2,7}$dodeca-2(7),3,5-trien-10-yl)-2,2,2-trifluoro-ethanone].

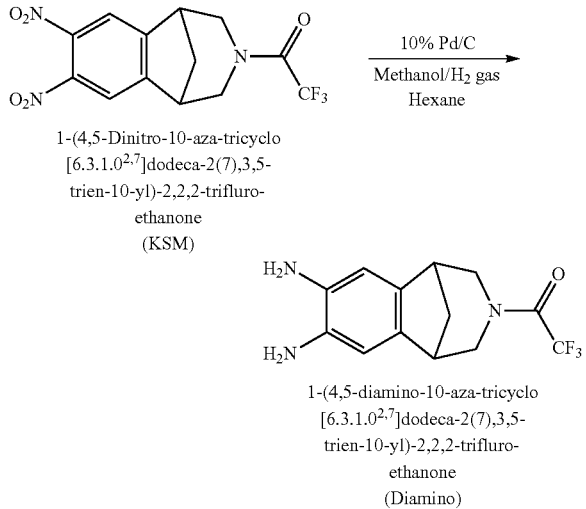

Part A

Reactor A and catalyst preparation vessel are pre-cleaned with methanol and dried under vacuum. Into Reactor A, the following materials are charged in order: 11.50×kg of methanol and 1.00×kg of 1-(4,5-Dinitro-10-aza-tricyclo[6.3.1.0$^{2,7}$]dodeca-2(7),3,5-trien-10-yl)-2,2,2-trifluoro-ethanone (KSM) at a temperature of 30±5° C. The Powder Transfer System (PTS) is flushed with 0.30×kg of methanol and the flushed methanol is transferred into Reactor A. Next, 1.00×kg of methanol is added to Reactor A through spray nozzle.

Into the catalyst preparation vessel, 0.10×kg of 10% palladium carbon and 1.00×kg of methanol are added under nitrogen atmosphere. The catalyst slurry is stirred for 10±5 minutes.

The pressure of the mixing vessel is raised to about 1.0 kg/cm$^2$ and the catalyst slurry is transferred from catalyst preparation vessel into Reactor A under nitrogen atmosphere.

1.00×kg of methanol is charged into the catalyst preparation vessel and the mixture is stirred for 5 minutes. The pressure is raised at 1.0 kg/cm$^2$ and the methanol is transferred into Reactor A under nitrogen atmosphere. 1.00×kg of methanol is charged into Reactor A through spray nozzle.

The reaction mass is stirred at 35±5° C. for 3 hours±5 minutes under hydrogen pressure of 5.0 to 6.0 kg/cm$^2$. Reaction is slightly exothermic. The temperature should not rise to more than 40° C. If temperature goes beyond 45° C., hydrogen is released and the mass is cooled using chilled water/chilled brine in the reactor jacket.

To monitor the reaction, a reaction sample is checked for the content of 1-(4,5-Dinitro-10-aza-tricyclo[6.3.1.0$^{2,7}$]dodeca-2(7),3,5-trien-10-yl)-2,2,2-trifluoro-ethanone(KSM) by HPLC analysis (% area). The test parameters are provided in Table 8.

TABLE 8

| Test parameters of the Reaction in Stage 1 | |
|---|---|
| Test parameters | Limit |
| 1-(4,5-Dinitro-10-aza-tricyclo[6.3.1.0$^{2,7}$]dodeca-2(7),3,5-trien-10-yl)-2,2,2-trifluoro-ethanone(KSM) | Not more than 0.5 |
| Peak 1 at RRT 1.23 | Not more than 0.5 |
| Peak 2 at RRT 1.30 | Not more than 0.5 |

If reaction sample complies the limit, then the next operation is proceeded with. If reaction sample does not comply the limit, the reaction mass is maintained at a temperature of 35±5° C. and a pressure of 5.0 to 6.0 kg/cm$^2$ and a sample is tested at an interval of every 2 hours until complies.

The reaction mass is then filtered from Reactor A through the catalyst filter and the clear filtrate is re-circulated back to Reactor A. The filtrate from catalyst filter is collected through the cartridge filter A into the mother liquor tank. 3.16×kg of methanol is then charged into Reactor A through spray nozzle. The methanol is filtered from Reactor A through the catalyst filter and the filtrate is transferred through cartridge filter A into the mother liquor tank. The filtrate from the mother liquor tank is transferred and collected in Reactor B through transfer line area under nitrogen atmosphere.

0.35×kg of methanol is then charged into the mother liquor tank under nitrogen atmosphere. The methanol from the mother liquor tank is then transferred and collected in Reactor B through transfer line area under nitrogen atmosphere.

80 L of process water is charged into the catalyst preparation vessel and 300 L of process water is charged into the Reactor A through spray nozzle. The water is re-circulated to Reactor A through the catalyst filter. The re-circulated water is drained into the mother liquor tank.

Part B

The reactor (Reactor B/C), Cartridge Filter B, and Centrifuge B are pre-cleaned with methanol and dried under vacuum. The vacuum tray dryer is flushed with hexanes (mixture of isomers) and dried under vacuum. The dryer is dried under vacuum.

If Reactor B is used, the filtrate from the Mother liquor tank is collected into Reactor B through Cartridge Filter B under nitrogen atmosphere. If Reactor C is used, the filtrate is collected from mother liquor tank into clean HDPE container through transfer line near Reactor C under nitrogen atmosphere. Approximately half the quantity of filtrate is charged into Reactor C through Cartridge Filter B from HDPE container under nitrogen atmosphere.

The methanol is distilled out completely under vacuum not less than 650 mmHg and temperature of not more than 45° C. The temperature should not exceed 45° C. and the distillation time should not exceed 15 hours. The vacuum is released under nitrogen atmosphere and the mass is cooled to 30±3° C.

0.34×kg of hexanes is charged into Reactor B under nitrogen atmosphere and a vacuum of NLT 650 mmHg is applied. The hexanes is completely distilled out under vacuum NLT 650 mmHg and temperature of NMT 45° C. The vacuum is released under nitrogen atmosphere and the mass is cooled to 30±3° C.

2.62×kg of Hexanes is charged into Reactors B/C at 30±3° C. under nitrogen atmosphere. The mass is stirred at 30±3° C. for 2 hour±5 minutes and is filtered through the centrifuge B at RPM of 500±50 under nitrogen atmosphere. The centrifuge RPM is raised to 950±50 and the material is stir dried. Reactor B is flushed with 0.655×kg of hexanes under nitrogen atmosphere.

The wet cake in the centrifuge B at RPM of 500±50 is washed with the hexanes obtained from the previous operation under nitrogen atmosphere. The centrifuge RPM is raised to 950±50 and the material is stir dried. The spin dried material is then charged into the dryer and dried at a temperature of 43±2° C. and under a vacuum of NLT 650 mmHg for 8 hours±5 minutes. The vacuum is then released and the dried material is unloaded and weighed.

YIELD: The expected yield is about 0.60× to 0.80×. The percentage yield [Percentage Yield=(Achieved Yield×100)/Theoretical Yield] is about from 72.28 to about 96.38%.

Example 2

Stage II: Preparation of 1-(5,8,14-Triazatetracyclo[10.3.1.0$^{2,11}$0.0.$^{4,9}$]Hexadeca-2(11),3,5,7,9-Pentaene)-2,2,2-Trifluoro-Ethanone The following is an illustration of the chemical reaction to produce 1-(5,8,14-triazatetracyclo[10.3.1.0$^{2,11}$0.0.$^{41}$]hexadeca-2(11),3,5,7,9-pentaene)-2,2,2-trifluoro-ethanone (Quinoxaline) starting from 1-(4,5-diamino-10-aza-tricyclo[6.3.1.0$^{2,7}$]dodeca-2 (7),3,5-trien-10-yl)-2,2,2-trifluoro-ethanone (Diamino). The synthetic procedure is discussed in details below. Throughout this synthetic procedure, X=38.00±1.50 kg of varenicline tartrate maltodextrin premix (1:10) Stage-01 (Diamino or "Varenicline Tartrate Maltodextrin Premix (1:10) Stage-01").

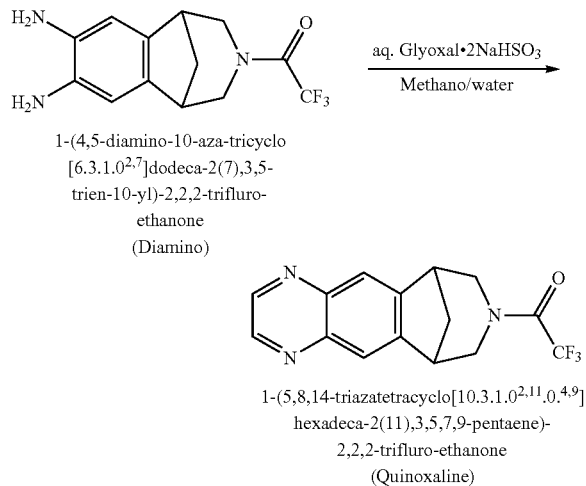

1-(4,5-diamino-10-aza-tricyclo
[6.3.1.0$^{2,7}$]dodeca-2(7),3,5-
trien-10-yl)-2,2,2-trifluro-
ethanone
(Diamino)

1-(5,8,14-triazatetracyclo[10.3.1.0$^{2,11}$.0.$^{4,9}$]
hexadeca-2(11),3,5,7,9-pentaene)-
2,2,2-trifluro-ethanone
(Quinoxaline)

Reactor 2-A and the Vacuum Tray Dryer are flushed with methanol and dried under vacuum. Reactor B/C is flushed with process water and dried under vacuum. The Glass Dosing Tank and the Centrifuge are cleaned with process water. The Cartridge Filter and the Mixing Vessel MV-0101 are flushed with methanol.

PREPARATION OF AQUEOUS GLYOXAL SODIUM BISULFITE SOLUTION: 5.61×L of process water is charged into Reactor B/C. 0.802×kg of sodium bisulfate is added into Reactor B/C under nitrogen atmosphere and 0.56×kg of 40% aqueous glyoxal is charged into Reactor B/C at 30±3° C. under stirring condition. The clarity of the solution is checked visually. If solution is clear, the next operation is proceeded to. If the solution is not clear, the solution is stirred at 30±3° C. and the clarity of the solution is checked every 15 minutes until the solution is clear.

1.58×kg of methanol is charged into Reactor 2-A under nitrogen atmosphere and 1.00×kg of Vareniclne Tartrate Maltodextrin Premix (1:10) Stage-01 (or diamino) is charged into Reactor 2-A at 30±3° C. 2.00×L of process water is added into Reactor 2-A under nitrogen atmosphere at 30±3° C. The mass is then stirred at 30±3° C. for 15±minutes. The mass temperature is raised to 58±2° C. under stirring.

The aqueous glyoxal sodium bisulfite solution is charged in lot wise into the Dosing Tank from Reactor B/C by using residual vacuum and the vacuum is released using nitrogen. Once all of the aqueous glyoxal sodium bisulfite solution in Reactor B/C is added into the Dosing Tank, the reactor is flushed with 0.15×L of process water and the flushed water is charged into the dosing tank.

The aqueous glyoxal sodium bisulfite solution is slowly added from Dosing Tank to Reactor 2-A at 58±2° C. over a period of 45 minutes. The flushed water from Dosing Tank is charged into Reactor 2-A. The mass is stirred at 58±2° C. for 3 hours±5 minutes. The Varenicline Tartrate Maltodextrin Premix (1:10) Stage-01 (or diamino) content is checked by HPLC analysis. The Varenicline Tartrate Maltodextrin Premix (1:10) Stage-01 (or diamino) content should be not more than 1.50 (% area). If the content is more than this limit, the reaction mass is maintained at 58±2° C. for 2 hours and re-tested at an interval of every 2 hours until it complies the limit. Once the HPLC sample complies the limit, the mass is then cooled to 30±3° C. Then, 10.00×L of process water is then charged into Reactor 2-A through charging line at 30±3° C. The mass is stirred at a temperature of 30±3° C. for 1 hour±5 minutes. If required, the mass is cooled to 27±3° C. The mass is stirred at a temperature of 27±3° C. for 1 hour±5 minutes.

CRUDE-I FILTRATION: The mass obtained from Reactor 2-A is filtered through the Centrifuge at RPM of 500±50 under nitrogen atmosphere. The Centrifuge RPM is raised to 950±50 and the material is spin dried. Reactor 2-A is flushed with 2.00×L of process water. The wet cake is washed in the Centrifuge at RPM of 500±50 with the process water obtained from the previous operation under nitrogen atmosphere. The Centrifuge RPM is raised to 950±50 and the material is spin dried. The Centrifuge is stopped and after waiting for 10±2 minutes, the spin dried material is unloaded from the Centrifuge under nitrogen atmosphere.

INTERMITTENT CLEANING: Reactor 2-A is flushed with 10 L of process water and the flushed water is drained in to strong effluent.

WATER SLURRY WASHING: 7.00×L of process water is charged into Reactor 2-A through charging line. The spin dried material is charged into Reactor 2-A through the manhole under nitrogen atmosphere. The mass is stirred for 10±5 minutes at 27±3° C.

INTERMITTENT CLEANING: The Centrifuge is flushed with 10 L of process water and the flushed water is drained in to strong effluent.

CRUDE-II FILTRATION: The mass obtained from Reactor 2-A is filtered through the Centrifuge at RPM of 500±50 under nitrogen atmosphere. The Centrifuge RPM is raised to 950±50 and the material is spin dried. Reactor 2-A is flushed with 2.00×L of process water. The wet cake is washed in the Centrifuge at RPM of 500±50 with the process water obtained from the previous operation under nitrogen atmosphere. The Centrifuge RPM is raised to 950±50 and the material is spin dried at RPM of 950±50. The Centrifuge is stopped. After waiting for 10±2 minutes, the spin dried material is unloaded under nitrogen atmosphere.

INTERMITTENT CLEANING: Reactor 2-A and Reactor B/C are flushed each with 10.00 kg of methanol. 5.00 kg of methanol is charged into the Glass Dosing Tank using vacuum and the methanol is bounced for three to four times by controlling vacuum. The bounced methanol is drained.

PURIFICATION: 3.00×kg of methanol is charged into Reactor 2-A under nitrogen atmosphere. The spin dried material is charged into Reactor 2-A under stirring at 30±3° C. under nitrogen atmosphere. Reactor 2-A is flushed with 0.95×kg methanol under nitrogen atmosphere. The mass temperature is raised to 55±2° C. while stirring. The clarity of the solution is checked visually. If the solution is not clear, then 0.50×kg of methanol is charged into Reactor 2-A through Dosing Tank by using residual vacuum at 55±2° C. under stirring and vacuum is released using nitrogen. This procedure can be repeated until the solution is clear. Once the solution is clear, the mass is transferred from Reactor 2-A to Reactor B/C through Cartridge Filter by using vacuum at 55±2° C. The mass is slowly cooled to 30±5° C. and then chilled to 7.5±2.5° C. The mass is stirred at 7.5±2.5° C. for 3 hours±5 minutes.

INTERMITTENT CLEANING: The Centrifuge is flushed with 5.00 kg of methanol.

PRODUCT ISOLATION: The mass obtained is filtered from Reactor B/C through the Centrifuge at RPM of 500±50 under nitrogen atmosphere. The Centrifuge RFM is raised to 950±50 and the material is spin dried. 0.79×kg of methanol is charged into the mixing vessel MV-0101 through charging line under nitrogen atmosphere. The methanol is chilled to 7.5±2.5° C. The chilled methanol is unloaded from mixing vessel MV-0101 into a HDPE container and Reactor B/C is flushed with chilled methanol under nitrogen atmosphere. The wet cake is washed with chilled methanol obtained from Reactor B/C in the Centrifuge at RPM of 500±50 under nitrogen atmosphere. The Centrifuge RPM is raised to 950±50 and the material is spin dried. The centrifuge is stopped and after waiting for 10±2 minutes, the spin dried material is unloaded under nitrogen atmosphere.

DRYING: The spin dried material is charged in to the dryer VTD-101/102 and is dried at a temperature of 43±2° C. and under a vacuum of NLT 650 mmHg for 10 hours±5 minutes. The Loss on drying (% w/w) at $10^{th}$ hour is checked. A sample should have a specification limit of NMT 1.0%. Once the drying is complete, drying is and the vacuum is released with nitrogen in the dryer. The dried material is unloaded and weighed.

YIELD: The expected yield is about 0.50× to 0.75×. The percentage yield [percentage yield=(Achieved Yield×100)/Theoretical Yield] is about from 46.29 to about 69.44%.

Example 3

Stage III: Preparation of Purified 7, 8,9,10-Tetra-hydro-6,10-Methano-6H-Pyrazino[2,3-H][31]Benzazepine The following is an illustration of the chemical reaction to produce 7,8,9,10-Tetrahydro-6,10-methano-6H-pyrazino[2,3-h][3]benzazepine (Varenicline Free Base) starting from 1-(5,8,14-triazatetracyclo[10.3.1.0$^{2,11}$.0.0.$^{4,9}$]hexadeca-2(11),3,5,7,9-pentaene)-2,2,2-trifluoro-ethanone (Quinoxaline). The synthetic procedure is discussed in details below. Throughout this synthetic procedure, X=27.00±3.00 kg of Varenicline Tartrate Maltodextrin Premix (1:10) Stage-02 (1-(5,8,14-triazatetracyclo[10.3.1.0$^{2,11}$0.0.$^{4,9}$]hexadeca-2(11),3,5,7,9-pentaene)-2,2,2-trifluoro-ethanone or (Quinoxaline)) and Y=quantity of Semi Dried Material A.

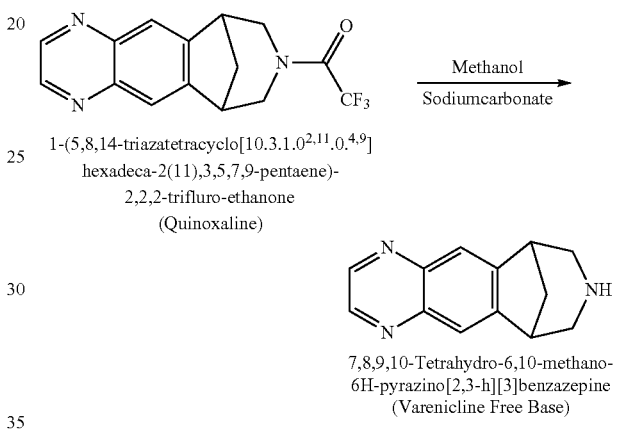

1-(5,8,14-triazatetracyclo[10.3.1.0$^{2,11}$.0.$^{4,9}$]
hexadeca-2(11),3,5,7,9-pentaene)-
2,2,2-trifluro-ethanone
(Quinoxaline)

7,8,9,10-Tetrahydro-6,10-methano-
6H-pyrazino[2,3-h][3]benzazepine
(Varenicline Free Base)

PRE-CLEANING: Reactor B/C and Reactor 2-A are flushed each with 10 L of purified water. The flushed purified water is drained in lean effluent and the reactors are dried under vacuum. Reactor C and Sparkler filter SF-0104 are each flushed with 10.00 kg of methylene dichloride. Reactor C is dried under vacuum. The Nutsche filter SSNF-301/NF-0303 is flushed with 10.00 kg of methanol. The Mixing Vessel MV-0101 is flushed with 5.00 kg of methanol. The filter cloth is fixed and the sparkler filter SF-0104 is assembled. The Cartridge Filter is flushed with 2.00 kg of methylene dichloride. The Vacuum Tray Dryer is flushed with 10.00 kg of tertiary butyl methyl ether and the dryer is dried under vacuum. The Holding Tank is flushed with 5.00 kg of methylene dichloride.

PREPARATION OF AQUEOUS SODIUM CARBONATE SOLUTION: 6.25×L of purified water and 0.69×kg of sodium carbonate are charged into Reactor 2-A and the mass is stirred until clear.

PREPARATION OF SODIUM CHLORIDE SOLUTION: 2.86×L of purified water and 1.00×kg of sodium chloride are charged into Reactor B/C and the sodium chloride solution is stirred for 10±5 minutes.

REACTION: 4.00×kg of methanol is charged into Reactor B/C through charging line under nitrogen atmosphere. 1.00×kg of Varenicline Tartrate Maltodextrin Premix (1:10) Stage-02 (or (1-(5,8,14-triazatetracyclo[10.3.1.0$^{2,11}$0.0.$^{4,9}$]hexadeca-2(11),3,5,7,9-pentaene)-2,2,2-trifluoro-ethanone) is charged into the reactor through Reactor B/C manhole/PTS/Powder charging AOD the manhole at 30±3° C. Reactor B/C is flushed with 0.74×kg of methanol at 30±3° C. under nitrogen atmosphere. The mass is stirred at 30±3° C.

for 15±5 minutes. The aqueous sodium carbonate solution is slowly transferred from Reactor 2-A into Reactor B/C through transfer line at 30±3° C. and the reaction mass is stirred at 30±3° C. for 15±5 minutes. The temperature of reaction mass is raised to 67±3° C.

INTERMITTENT CLEANING: Reactor 2-A is flushed with 10.00 kg of methanol.

The mass is stirred at 67±3° C. for 3 hours±5 minutes. To monitor the reaction, a sample is checked for varenicline tartrate Stage-02 (this is 1-(5,8,14-triazatetracyclo[10.3.1.0$^{2,11}$0.0.$^{4,9}$] hexadeca-2(11),3,5,7,9-pentaene)-2,2,2-trifluoro-ethanone or Quinoxaline) content by HPLC analysis. The content should be NMT 0.10 (% area). If varenicline tartrate Stage-02 by HPLC sample does not comply the limit, the reaction mass is maintained at a temperature of 67±3° C. and a sample is checked at an interval of every 2 hours until complies. The reaction mass is then cooled to 30±3° C.

FILTRATION: The reaction mass is filtered from Reactor B/C through Nutsche filter SSNF-301/NF-0303 under nitrogen atmosphere. Using vacuum, the material is suck dried under nitrogen atmosphere until the rate of removal of the mother liquor reduces to few drops per minute as observed visually. Reactor B/C is flushed with 1.58×kg of methanol. The wet cake is washed with the flushed methanol obtained from the previous operation. Using vacuum, the material is suck dried under nitrogen atmosphere until the rate of removal of the filtrate reduces to few drops per minute as observed visually. The wet cake is uploaded from the Nutsche filter.

INTERMITTENT CLEANING: Reactor B/C is flushed with 10.00 kg of methanol.

DISTILLATION: The filtrate is charged into Reactor B/C through vacuum/charging nozzle under nitrogen atmosphere. A vacuum of NLT 650 mmHg is applied to Reactor B/C. Next, 3.0×-6.0×kg of methanol is distill out under vacuum NLT 650 mmHg and temperature of NMT 50° C. The vacuum is released using nitrogen in Reactor B/C. The mass is cooled to 30±3° C. and 5.00×L of purified water is charged into Reactor B/C at 30±3° C. 1.25×kg of sodium chloride is charged into Reactor B/C at 30±3° C. under nitrogen atmosphere. The mass is stirred at 30±3° C. for 15±5 minutes.

EXTRACTION-I: 6.65×kg of methylene dichloride is charged into Reactor B/C line under nitrogen atmosphere. The mass is stirred at 30±3° C. for 20±5 minutes. Next, stirring is stopped and the mass is allowed to settle for 20±5 minutes. The bottom organic layer (product layer) is separated from Reactor B/C into the Holding Tank and the top aqueous layer is retained in the reactor itself. The extraction is repeated 3 times further (total of 4 extractions).

INTERMITTENT CLEANING: Reactor B/C is flushed with 10 L of purified water and the flushed water is drained into strong effluent.

The organic layer from the Holding Tank is transferred to Reactor 2-A under nitrogen atmosphere. The sodium chloride solution from Reactor B/C is transferred to Reactor 2-A under nitrogen atmosphere. The mass is stirred at 30±3° C. for 20±5 minutes and then allowed to settle for 20±5 minutes. The bottom organic layer is separated from Reactor 2-A into Holding Tank and the aqueous layer is collected into the separate container.

INTERMITTENT CLEANING: Reactor 2-A is flushed with 10.00 kg of methanol and then with 10.00 kg of methylene dichloride.

PREPARATION OF HYFLO BED IN SPARKLER FILTER: 130.00 kg of methylene dichloride is charged in Reactor 2-A through the reactor charging line under nitrogen atmosphere. 5.00 kg of hyflo is charged into Reactor 2-A through the reactor manhole and stirring is started until the hyflo is completely dispersed in the methylene dichloride. The hyflo is filtered through sparkler filter SF-0104 and a hyflo bed is formed. This step is re-circulated until a clear filtrate is obtained and the methylene dichloride is then drained from Reactor 2-A in a clean HDPE container. The methylene dichloride is drained from the sparkler filter before filtration only.

INTERMITTENT CLEANING: Reactor 2-A and Reactor C are flushed each with 10.00 kg of methylene dichloride.

The organic layer is transferred from the Holding Tank to Reactor 2-A through transfer line under nitrogen atmosphere. 0.10×kg of activated carbon is charged into Reactor 2-A through the manhole at 30±3° C. and the mass is stirred at 30±3° C. for 30±5 minutes. The reaction mass is then filtered from Reactor 2-A through the Sparkler Filter SF-0104 and the filtrate is transferred to Reactor C through Cartridge Filter under nitrogen atmosphere (before filtration, the methylene dichloride is drained from Sparkler Filter). Next, 2.66×kg of methylene dichloride is charged into Reactor 2-A through charging line under nitrogen atmosphere. The methylene dichloride obtained from Reactor 2-A is filtered through the Sparkler filter SF-0104 and the filtrate is transferred to Reactor C through Cartridge Filter under nitrogen atmosphere. A vacuum is applied to Reactor C.

DISTILLATION: Methylene dichloride is distilled out under vacuum and temperature of NMT 40° C. 1.48×kg of tertiary butyl methyl ether is charged into Reactor C by using vacuum. Next, tertiary butyl methyl ether is distilled out under vacuum and temperature of NMT 40° C. The vacuum is released using nitrogen. The mass is cooled to 30±3° C. Next, 2.96×kg of tertiary butyl methyl ether is charged into Reactor C through charging line under nitrogen atmosphere at 30±3° C. The mass is stirred at 30±3° C. for 1 hour±5 minutes. The mass is chilled to 7±3° C. and stirred for 2 hours±5 minutes.

INTERMITTENT CLEANING: The Nutsche filter SSNF-301/NF-0303 is flushed with 5.00 kg of tertiary butyl methyl ether.

PRODUCT ISOLATION: The reaction mass is filtered from Reactor C through the Nutsche filter SSNF-301/NF-0303 under nitrogen atmosphere. Using vacuum, the material is suck dried under nitrogen atmosphere. The mother liquor is collected in a clean HDPE container. Reactor C is flushed with tertiary butyl methyl ether under nitrogen atmosphere and the flushed tertiary butyl methyl ether is transferred to mixing vessel MV-0101. The wet cake in the Nutsche filter is washed with the flushed tertiary butyl methyl ether from Reactor C and suck dried under nitrogen atmosphere. The mother liquor is collected in the HDPE container. The suck dried material is unloaded from the Nutsche filter under nitrogen atmosphere. The suck dried material is dried at a temperature of 43±2° C. and under a vacuum of NLT 650 mmHg for 2 hours±5 minutes. A sample of the semi dried material (Semi Dried Material A) is weighed and collected for analysis.

PREPARATION OF AQUEOUS SODIUM CARBONATE SOLUTION: 10.00 Y L of purified water and 1.00 Y kg of sodium carbonate are charged into Reactor 2-A and stirred.

PREPARATION OF L(+)TARTARIC ACID SOLUTION: 5.00 Y L of purified water is charged into a clean HDPE container and 0.78 Y kg of L (+) Tartaric acid is charged into the same HDPE container. The mixture is stirred to get clear solution.

INTERMITTENT CLEANING: Reactor B/C is flushed first with 10.00 kg of methanol and then with 10.00 kg of methylene dichloride.

PURIFICATION: 6.65 Y Kg of methylene dichloride is charged into the reactor B/C through charging line under nitrogen atmosphere. Semi Dried Material A is charged into Reactor B/C under nitrogen atmosphere. The mass is stirred at 30±5° C. for 10±5 minutes. The L(+)Tartaric acid solution is charged into Reactor B/C under nitrogen atmosphere. The reaction mass is stirred at 30±5° C. for 15±5 minutes. Stirring is stopped and the mass is allowed to settle for 20±5 minutes. The bottom organic layer is separated from Reactor B/C into a clean HDPE container and the top aqueous layer is retained in the reactor itself.

6.65 Y Kg of methylene dichloride is charged into Reactor B/C through charging line under nitrogen atmosphere. The mass is stirred at 30±5° C. for 20±5 minutes. Stirring is stopped and the mass is allowed to settle for 20±5 minutes. The bottom organic layer is separated from Reactor B/C into a clean HDPE container and the top aqueous layer is retained in the reactor itself.

The aqueous sodium carbonate solution is transferred into Reactor B/C from the Reactor 2-A through transfer line under nitrogen atmosphere. The mass is stirred at 30±5° C. for 20±5 minutes.

EXTRACTION: 13.30 Y kg of methylene dichloride is charged into Reactor B/C through charging line under nitrogen atmosphere. The mass is stirred at 30±5° C. for 20±5 minutes. Stirring is stopped and the mass is allowed to settle for 20±5 minutes. The bottom organic layer is separated from Reactor B/C into the Holding Tank and the top aqueous layer is retained in the reactor itself. The extraction is repeated three times further. At the end, the aqueous layer is unloaded into the separate container.

INTERMITTENT CLEANING: Reactor C is flushed with 10 L of purified water and the flushed water is drained in strong effluent.

PREPARATION OF SODIUM CHLORIDE SOLUTION: 4.30 Y L of purified water and 1.50 Y kg of sodium chloride are charged into Reactor C and the sodium chloride solution is stirred for 10±5 minutes.

INTERMITTENT CLEANING: Reactor 2-A is flushed first with 10 L of purified water and then with 10.00 kg of methylene dichloride.

The organic layer is transferred from the Holding Tank to Reactor 2-A through transfer line under nitrogen atmosphere. The sodium chloride solution is transferred from Reactor C into Reactor 2-A through transfer line under nitrogen atmosphere. The mass is stirred at 30±5° C. for 20±5 minutes. Stirring is stopped and the mass is allowed to settle for 20±5 minutes. The bottom organic layer is separated from Reactor 2-A into Holding Tank and the aqueous layer is collected into a separate container.

INTERMITTENT CLEANING: Reactor C is flushed with 10.00 kg of methylene dichloride and the Cartridge Filter is flushed with 2.00 kg of methylene dichloride.

The organic layer is transferred from Holding Tank through Cartridge Filter into Reactor C through charging line under nitrogen atmosphere and vacuum is applied to Reactor C.

DISTILLATION: Methylene dichloride is distilled out under vacuum and temperature of NMT 40° C. 1.48 Y kg of tertiary butyl methyl ether is charged into Reactor C by vacuum/charging line under nitrogen atmosphere. Next, tertiary butyl methyl ether is distilled under vacuum and temperature of NMT 40° C. The vacuum is released using nitrogen and the mass is cooled to 30±3° C.

2.96 Y kg of tertiary butyl methyl ether is flushed into Reactor C under nitrogen atmosphere at 30±3° C. The mass is stirred at 30±3° C. for 1 hour±5 minutes and then chilled to 7±3° C. Next, the mass is stirred at 7±3° C. for 2 hours±5 minutes.

INTERMITTENT CLEANING: The Nutsche filter SSNF-301/NF-0303 is flushed with 5.00 kg of tertiary butyl methyl ether.

PRODUCT ISOLATION: The reaction mass is filtered from Reactor C through the Nutsche filter SSNF-301/NF-0303 under nitrogen atmosphere. Using vacuum, the material is suck dried under nitrogen atmosphere. Reactor C is flushed with 0.74 Y kg of tertiary butyl methyl ether under nitrogen atmosphere and the flushed tertiary butyl methyl ether is transferred to mixing vessel MV-0101. The flushed tertiary butyl methyl ether is chilled to 7±3° C. and unloaded in HDPE container. Reactor C is flushed with chilled tertiary butyl methyl ether under nitrogen atmosphere. Vacuum in Nutsche filter SSNF-301/NF-0303 is released using nitrogen. The wet cake in the Nutsche filter is washed with the flushed tertiary butyl methyl ether from Reactor C and suck dried under nitrogen atmosphere.

0.74 Y kg of tertiary butyl methyl ether is charged into the mixing vessel MV-0101 under nitrogen atmosphere. The flushed tertiary butyl methyl ether is chilled to 7±3° C. and unloaded in HDPE container. Reactor C is flushed with chilled tertiary butyl methyl ether under nitrogen atmosphere. Vacuum in Nutsche filter SSNF-301/NF-0303 is released using nitrogen. The wet cake in the Nutsche filter is washed with the flushed tertiary butyl methyl ether from Reactor C and suck dried under nitrogen atmosphere. Vacuum in Nutsche filter SSNF-301/NF-0303 is released using nitrogen and the suck dried material is unloaded under nitrogen atmosphere.

INTERMITTENT CLEANING: The Vacuum Tray Dryer is flushed with 10.00 kg of tertiary butyl methyl ether. The dryer is dried under vacuum.

DRYING: The suck died material is dried at a temperature of 43±2° C. and under a vacuum of NLT 650 mmHg for 14 hours±5 minutes. Sample is checked for Loss on Drying (Specification Limit: NMT 2.0 (% w/w)). If complies, the vacuum in the dryer is released with nitrogen. The dried material is allowed to rest for 10±2 minutes and then is unloaded in an inner translucent and outer black polyethylene bags, weighed, a sample is taken for testing and the bags are closed. Material is stored at a temperature of 2° C. to 8° C.

YIELD: The expected yield is about 0.20× to 0.60×. The percentage yield [Percentage Yield=(Achieved Yield×100)/Theoretical Yield] is from about 28.98 to about 86.95%.

Example 4

Stage IV: Preparation of Varenicline Tartrate Maltodextrin Premix (1:10)

The following is an illustration of the chemical reaction to produce 7,8,9,10-Tetrahydro-6,10-methano-6H-pyrazino[2,3-h][3]benzazepine,(2R,3R)-2,3-dihydroxybutanedioate. Maltodextrin Premix (Varenicline Tartrate Maltodextrin Premix (1:10)) starting from 7,8,9,10-Tetrahydro-6,10-methano-6H-pyrazino[2,3-h][3]benzazepine (Varenicline Free Base). The synthetic procedure is discussed in details below. Throughout this synthetic procedure, X=1.00±0.20 kg of Varenicline Tartrate Maltodextrin Premix (1:10) stage-03 (or 7,8,9,10-Tetrahydro-6,10-methano-6H-pyrazino[2,3-h][3]benzazepine (Varenicline Free Base)) after LOD correction and Y=calculated quantity of L(+) Tartaric acid.

*Dry weight of Stage-3 is calculated using the following formula:

Actual weight $(X) =$ $$\text{Dry weight of Stage-3} - \left(\frac{\text{LOD of Stage-3}}{100} \times \text{Dry weight of Stage-3}\right)$$

**Weight of L(+)Tartaric acid is calculated using the following formula:

$$\text{Actual weight } (Y) = \left(\frac{\text{Stage-3}(X) \times 70.3}{\text{Assay of } L(+) \text{ Tartaric acid}}\right)$$

***Weight of Maltodextrin is calculated using the following formula:

Actual weight $(Z) = 17.12 \times \text{Stage-3}(X) +$ (Water content of Maltodextrin$\times 0.1712 \times$Weight of Stage-3$(X)$)

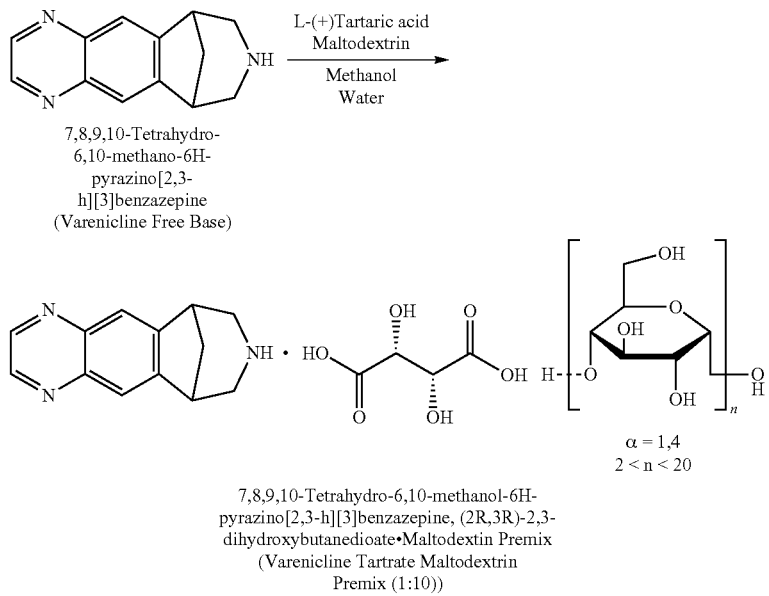

PRE-CLEANING: The mixing vessel MV-05-SD-1201 and the mixing vessel MV-1-5D-1201 are flushed each with 5.00 kg of methanol. The feed preparation vessel FPV-1-SD-1201 is flushed with 5.00 kg of purified water and the flushed water is drained into the lean effluent. The cartridge filter CGF-1205/1206 is flushed with 2.00 kg of methanol (Cartridge: 0.20 micron). Spray Dryer SD-1201 and vacuum tray dryer VTD-1201 are each flushed with 10.00 kg of methanol and dried. Sifter SFT-1201 and its mesh are flushed with 5.00 kg of methanol. The sifter is wiped thoroughly with lint free cloth and dried using nitrogen. 20 # sifter mesh is fixed in the sifter SFT-1201.

15.80×kg of methanol is charged into mixing vessel MV-05-SD-1201. 1.00×kg of Varenicline Tartrate Maltodextrin Premix (1:10) stage-03 (or 7,8,9,10-Tetrahydro-6,10-methano-6H-pyrazino[2,3-h][3]benzazepine (Varenicline Free Base)) is charged into Mixing vessel MV-05-SD-1201. The mass is stirred until clear solution is obtained and the solution is transferred to feed preparation vessel FPV-1-SD-1201.

PREPARATION OF L(+)TARTARIC ACID SOLUTION: 10.00×kg of purified water and 1.00 Y kg of L (+) Tartaric acid are charged into the mixing vessel MV-05-SD-1201. The mass is stirred until clear solution is obtained. The solution is transferred to feed preparation vessel FPV-1-SD-1201.

PREPARATION OF MALTODEXTRIN SOLUTION: 60.07×kg of purified water and 17.12×kg of maltodextrin are charged into a mixing vessel MV-05-SD-1201. The mass is stirred until clear solution is obtained. The solution is transferred to feed preparation vessel FPV-1-SD-1201. The mass is stirred at 30±3° C. for 30±5 minutes in feed preparation vessel FPV-1-SD-1201. The mass is transferred from the feed preparation Vessel FPV-1-SD-1201 to mixing vessel MV-1-SD-1201 through cartridge filter CGF-1205/1206 under nitrogen atmosphere and a clear solution is obtained.

The mixing vessel MV-05-SD-1201 is flushed with 20.00×kg of purified water. The flushed purified water is transferred to feed preparation vessel FPV-1-SD-1201. The flushed water is filtered from the feed preparation Vessel FPV-1-SD-1201 to mixing vessel MV-1-SD-1201 through cartridge filter CGF-1205/1206 under nitrogen atmosphere to obtain clear solution.

SPRAY DRYING: Spray dryer SD-1201 needs to be visually clean and dry. Nitrogen gas pressure is used for atomization. Plain solvent mixture (Mixture A) with 3.60 kg of methanol and 16.40 kg of purified water is prepared in HDPE container. The spray dryer is switched on, the required parameters in spray dryer are set as shown in Table 10, and the spray dryer is run with plain solvent mixture (Mixture A) to achieve steady state. The solution is fed to the spray dryer SD-1201 from the mixing vessel MV-1-SD-1201.

TABLE 10

| Required Parameters in Spray Dryer | |
|---|---|
| Inlet Temperature | 130 ± 15° C. |
| ID Blower flow rate | 750 ± 150 NM³/hr |
| FD Blower flow rate | 400 ± 100 NM³/hr |
| Atomization Pressure | 3.6 ± 0.6 kg/cm² |
| Feed flow rate | 60 ± 30 ml/min |

The spraying chamber of Spray dryer is intermittently cleaned with purified water for every 3 hours±5 minutes and dried using nitrogen. The spray dryer is run with plain solvent mixture to achieve steady state. The feed solution is fed for NMT 3 hours. The material from the spray dryer is unloaded under nitrogen atmosphere. The spray dried material is charged into the dryer VTD-1201. Initial Residual Solvent Analysis is conducted using GC. The results are provided in Table 11 below.

TABLE 11

| RESIDUAL OF SOLVENT BY GC | |
|---|---|
| Test Parameters | Specification Limit [observed results] |
| a. Methanol | NMT 3000 ppm [700-2300 ppm] |
| b. MTBE | NMT 5000 ppm [Not detected] |
| c. Methylene dichloride | NMT 600 ppm [Not detected] |

DRYING: The material is dried at a temperature of 35±5° C. and under a vacuum of NLT 650 mmHg for 12 hours±5 minutes. The Loss on Drying is checked (specification limit: NMT 3.5% w/w). Once the sample complies with this limit, the drying is stopped and the vacuum is released with nitrogen. After 10±2 minutes, the dried material is unloaded under nitrogen atmosphere and weighed.

SIFTING: The bag containing the dried material is tied in the discharge chute under of the sifter SFT-1201 to collect the sifted material under nitrogen atmosphere. The sifter SFT-1201 is turned on and the material is charged into the sifter using a clean scoop under nitrogen atmosphere. The sifter is run until the completion of the sifting and the sieved material is collected into a bag fixed in the discharge chute under nitrogen atmosphere and weighed. The material is moved to cold storage area.

YIELD: The expected yield is about 8.00× to 18.0×. The percentage yield [Percentage Yield=(Achieved Yield×100)/Theoretical Yield] is from about 42.78 to about 96.25%.

Example 5

Characterization of Varenicline Tartrate Maltodextrin Premix (1:10)

Figure 2:
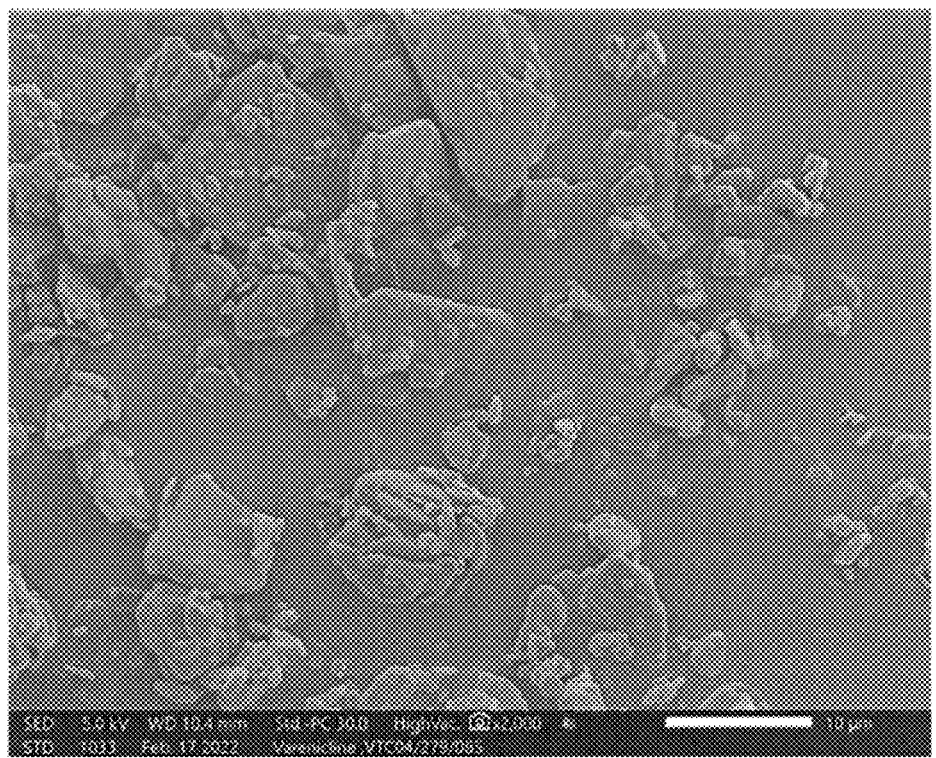
FIG. 2 is a SEM image of crystalline API-PAT (crystalline varenicline tartrate salt).
Figure 3:
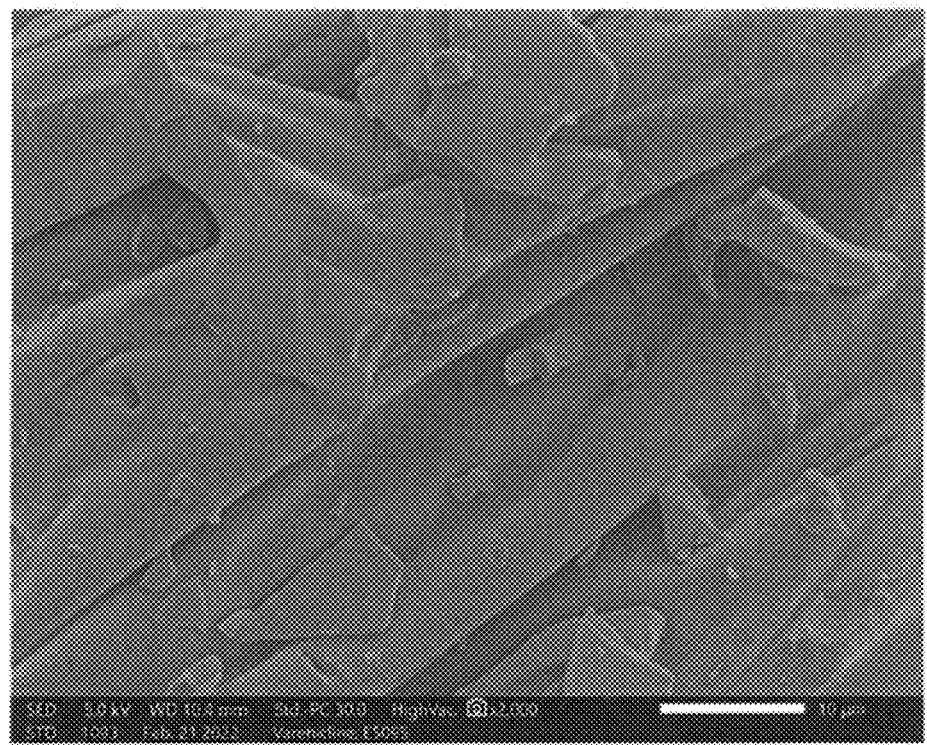
FIG. 3 is a SEM image of maltodextrin (Glucidex 12D).
Figure 4:
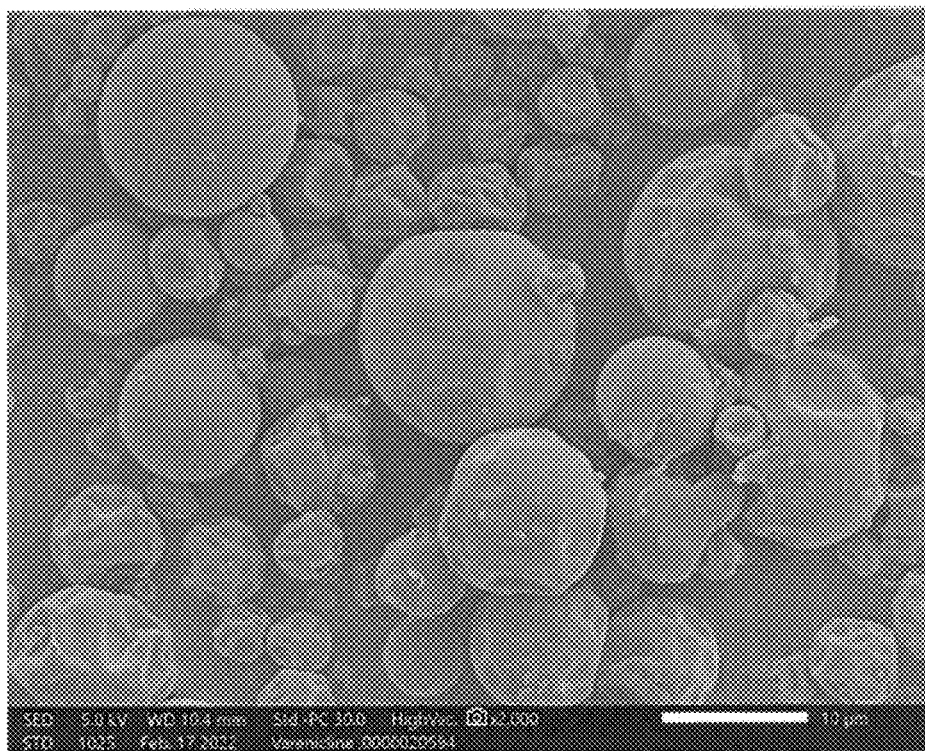
FIG. 4 is a SEM image of API Premix (varenicline tartrate:Maltodextrin—1:10)_PAT.
Figure 5:
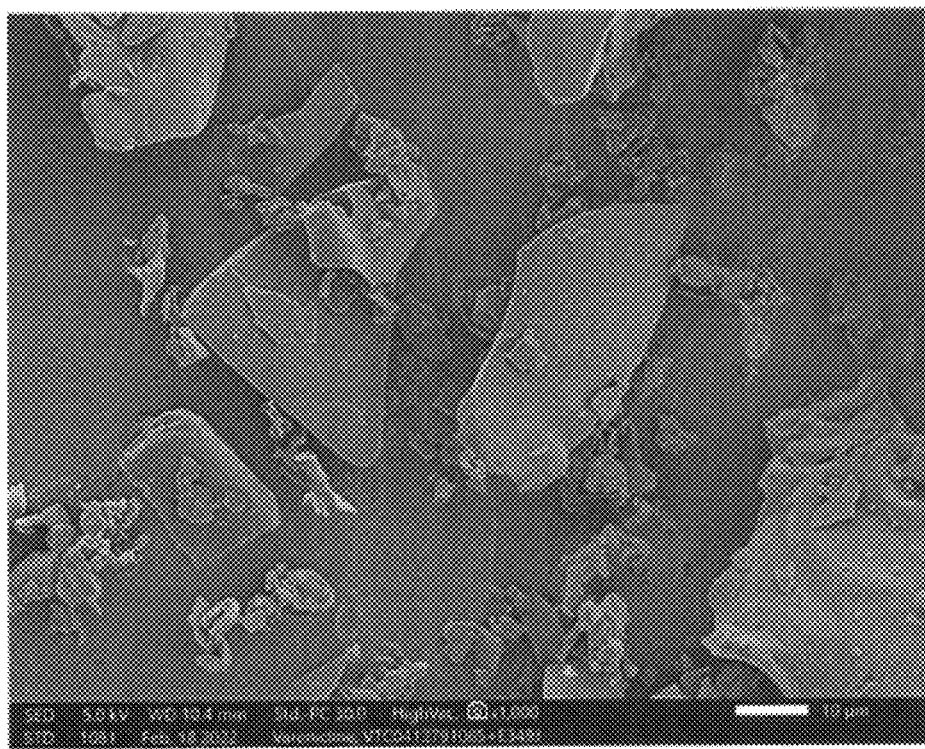
FIG. 5 is a SEM image of API+Maltodextrin (Physical Mix) (1:10).

The Scanning Electron Microscopy (SEM) was used for imaging of crystalline API-PAT (crystalline varenicline tartrate salt) (FIG. 2), maltodextrin (Glucidex 12D) (FIG. 3), API Premix (varenicline tartrate:Maltodextrin—1:10) PAT (FIG. 4) and API+Maltodextrin (Physical Mix) (1:10) (FIG. 5).

The spray drying process renders a near spherical morphology of the premix of the present disclosure, as observed from the SEM images. Such morphology is not observed in the physical mixture between varenicline tartrate and maltodextrin, in the same weight ratio as that used in the premix (i.e. 1:10). This result shows that the spray drying process of the present disclosure produces nearly spherical shaped particles, where varenicline tartrate is uniformly dispersed in maltodextrin matrix.

The near to spherical morphology of the spray dried premix, offers minimal surface area for the premix, as for a given volume, a spherical shape has the lowest surface area. This low surface area of the premix particles is likely to be a key factor, contributing to lower extent of interaction (contact) between the premix particles and the other excipients used in the formulation, thus reducing the chances of generation of any impurities that is likely to be formed because of such interaction (contact).

The reduction of the surface:volume ratio by creating spherical agglomerations of the varenicline/maltodextrin mixture reduces the amount of contact between the active and other excipients, thereby diminishing the likelihood of impurity generation.

Such morphology is not observed in the physical mixture between Varenicline Tartrate & Maltodextrin, in the same weight ratio as that used in the premix (i.e. 1:10). This shows that the spray drying process of the current disclosure produces nearly spherical shaped particles, where Varenicline tartrate is uniformly dispersed in maltodextrin matrix.

The near to spherical morphology of the spray dried premix, offers minimal surface area for the premix, as for a given volume, a spherical shape has the lowest surface area. This low surface area of the premix particles is likely to be a key factor, contributing to lower extent of interaction (contact) between the premix particles and the other excipients used in the formulation, thus reducing the chances of generation of any impurities that is likely to be formed because of such interaction (contact).

Example 6

X-Ray Diffraction Studies

Figure 6A:
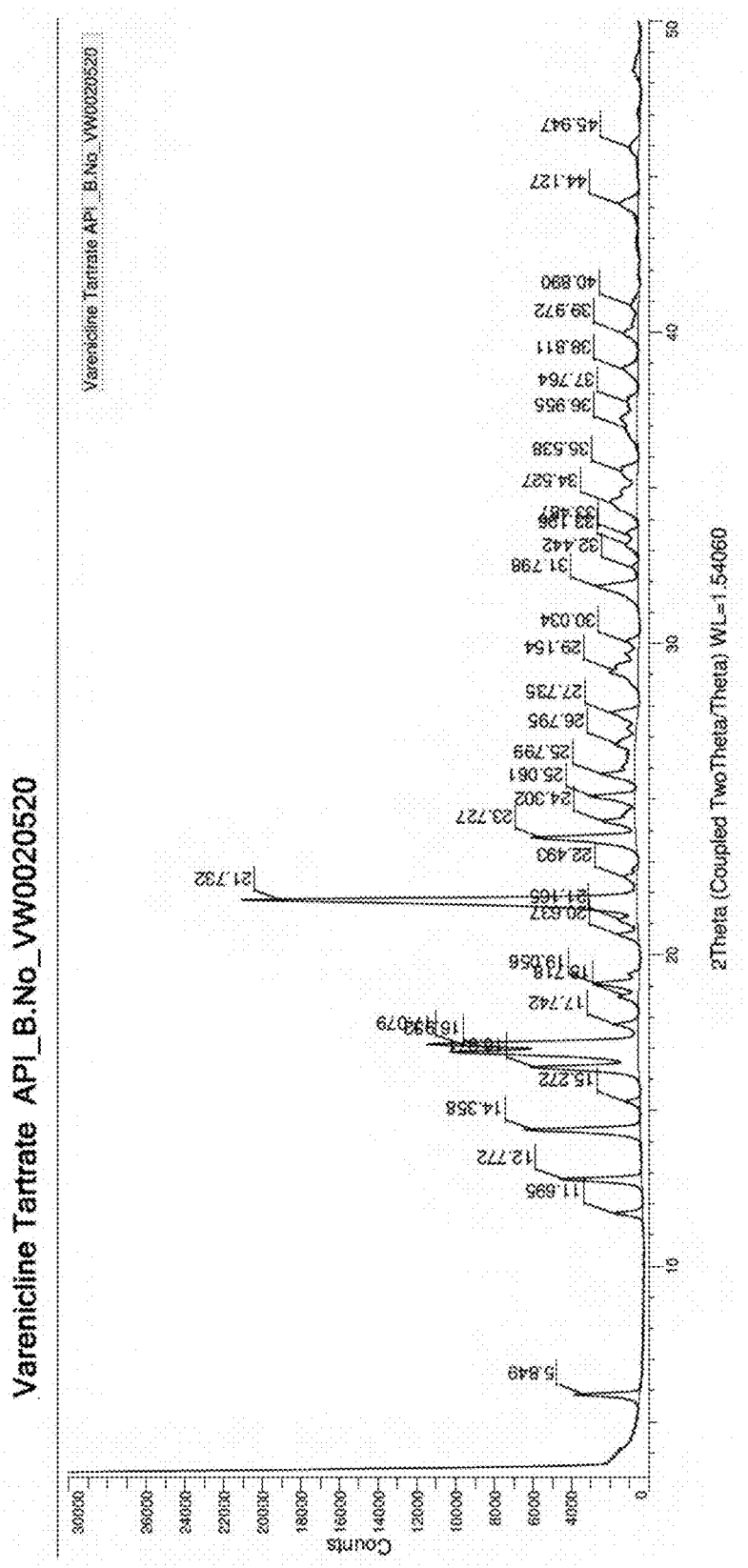
FIG. 6A is an X-ray diffractogram of varenicline tartrate shows presence of signature peaks for crystalline form B.
Figure 7:
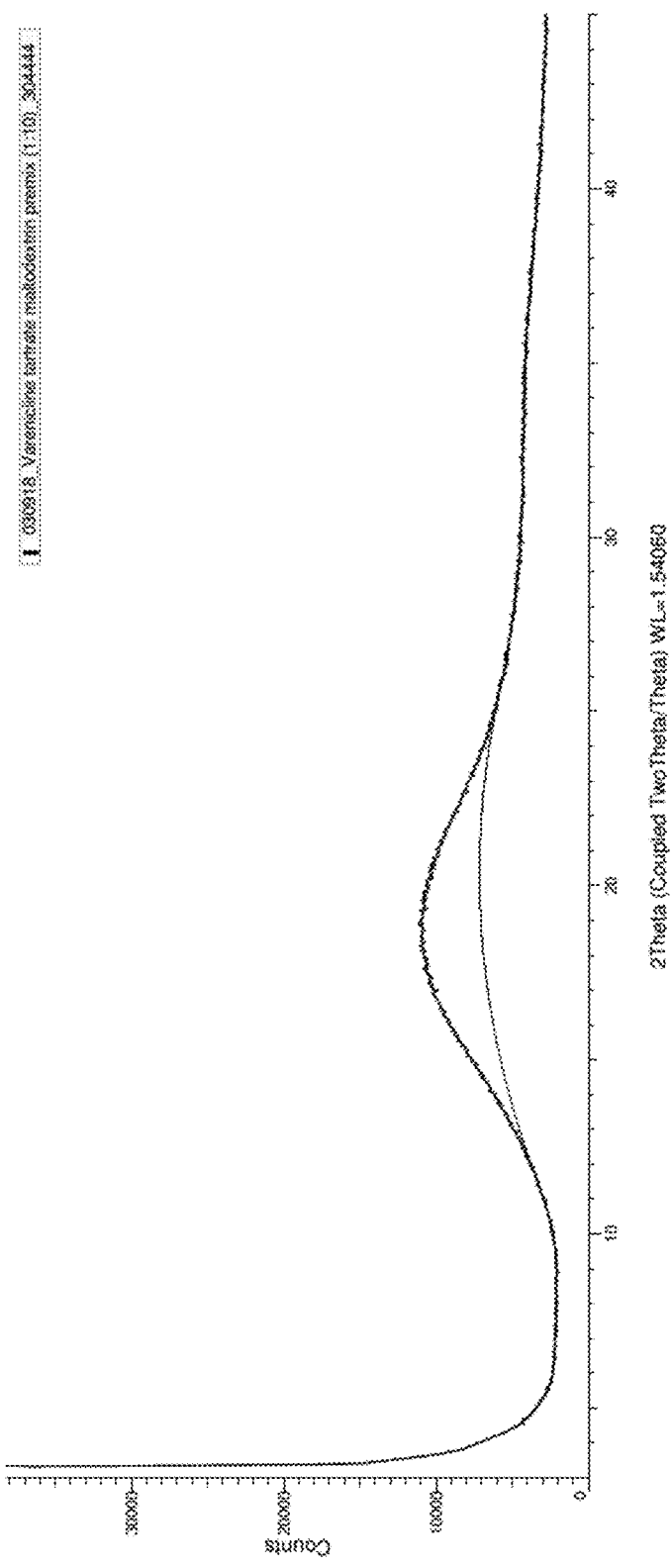
FIG. 7 is an X-ray diffractogram of varenicline tartrate maltodextrin premix (1:10) exists in an amorphous form. No crystalline peaks characteristic of crystalline varenicline tartrate is observed in the diffractogram.

The X-ray diffractorgram of varenicline tartrate shows presence of signature peaks for Crystalline form B (FIG. 6A and FIG. B). On the other hand, the spray drying process results in varenicline-maltodextrin premix which exist in the amorphous form, as observed by the X-ray diffraction studies (FIG. 7).

The dilution of varenicline tartrate in the spray dried premix form is likely to be responsible for lowering the contact of the drug substance with the other excipients in the formulation. This effect may help in controlling the levels of impurities in the drug product of the current disclosure, which are formed by the interaction of the drug substance with the excipients, when they come in close contact.

The spray drying process results in Varenicline-maltodextrin premix which exist in the amorphous form, as observed by the X-ray diffraction studies.

The dilution of Varenicline tartrate in the spray dried premix form is likely to be responsible for lowering the contact of the drug substance with the other excipients in the formulation.

This may help to control the levels of impurities in the drug product manufactured by Applicant, which are formed by the interaction of the drug substance with the excipients, when they come in close contact.

Example 7

Testing for Impurities

LC-ESI-HRMS Method for the Determination of Varenicline Nitroso-Drug Substance Related Impurity, U.S. FDA, Aug. 6, 2021, https://www.fda.gov/media/151470/download (accessed Feb. 27, 2022) can be used to test for impurities.

Other analytical methods for the entire process can be used to test for impurities. The methods are validated as per ICH guideline.

For example, HPLC RS methods are used for quantifying the impurities. The nitrosamines, monomethyl and dimethyl tartaric acid esters are quantified by LCMS methods.

Example 8

Analytical Methods for Analyzing Varenicline Base (Stage 3) and Varenicline Tartrate Maltodextrin Premix API Two Related Substance methods by HPLC were developed for analyzing Varenicline base (Stage 3) for quantifying all impurities having a similar chromophore of Varenicline. The same two HPLC methods were adopted for analyzing the Varenicline Tartrate Maltodextrin Premix API for quantifying the respected impurities. A third additional RS method by HPLC was developed for analyzing two additional impurities viz. N-methyl Varenicline and Varenicline-N-Gluoside which could form due to reaction of degradation products of Maltodextrin with Varenicline. Moreover, two LCMS methods were developed for analyzing monomethyl and dimethyl esters of tartaric acid as impurities in Varenicline Tartrate Maltodextrin premix API. Furthermore, two LCMS methods were developed for quantifying the Nitrosamine impurities in Varenicline Tartrate Maltodextrin Premix API. The detailed methods and LOD and LOQ values are discussed below. Lists of the Related Substances Method-I and Related Substances Method-II are provided in Tables 12 and 13, respectively.

TABLE 12

Related Substances Method-I

| Related substances by HPLC (Method-I) (% w/w) | Chemical Name of the Impurities | Limits (% w/w) |
| --- | --- | --- |
| Impurity D | (2,3,4,5-tetrahydro-1H-1,5-methano-3-benzazepine-6,8-diamine) | Not more than 0.0438 |
| Impurity F | (7,8-Diamino-2,3,4,5-tetrahydro-1H-1,5-methano-3-benzazepine) | Not more than 0.0438 |
| Impurity C | (2,3,4,5-tetrahydro-1H-1,5-methano-3-benzazepin-7-amine) | Not more than 0.0438 |
| Methyl Varenicline | 2-methyl-7,8,9,10-tetrahydro-6H-6,10-methanoazepino[4,5-g]quinoxaline | Not more than 0.15 |
| Varenicline Stage-01 | 1-(4,5-diamino-10-aza-tricyclo [6.3.1.0$^{2-7}$]dodeca-2(7),3,5-trien-10-yl)-2,2,2-trifluoro-ethanone (Diamino protected) | Not more than 0.0438 |
| Varenicline Stage-02 | 1-(5,8,14-Triazatetracyclo [10.3.1.0$^{2,11}$.0$^{4,9}$]hexadeca-2(11),3,5,7,9-pentaene)-2,2,2-trifluro-ethanone (Quinoxaline) | Not more than 0.15 |
| Varenicline KSM | 1-(4,5-dinitro-10-aza-tricyclo[6.3.1.0$^{2,7}$] dodeca-2(7),3,5-trien-10-yl)-2,2,2-trifluoro-ethanone (Dinitro protected) | Not more than 0.0438 |

TABLE 13

Related Substances Method-II

| Related substances by HPLC (Method-II) (% w/w) | Chemical Name of the Impurities | Limits (% w/w) |
| --- | --- | --- |
| Mononitro deprotected | 7-nitro-2,3,4,5-tetrahydro-1H-1,5-methano-3-benzazepine | Not more than 0.0438 |
| Metadinitro deprotected | 3,5-Dinitro-10-aza-tricyclo [6.3.1.0$^{2,7}$]dodeca-2,4,6-triene or 2,3,4,5-tetrahydro-6,8-dinitro-1,5-methano-1H-3-benzazepine or 6,8-dinitro-2,3,4,5-tetrahydro-1H-1,5-methano-3-benzazepine | Not more than 0.0438 |
| Metadiamino protected | 3-(trifluoroacetyl)-2,3,4,5-tetrahydro-1H-1,5-methano-3-benzazepine-6,8-diamine | Not more than 0.0438 |
| Varenicline Impurity-G | (7,8-Dinitro-2,3,4,5-tetrahydro-1H-1,5-methano-3-benzazepine) | Not more than 0.0438 |
| Monoamino protected | 3-(trifluoroacetyl)-2,3,4,5-tetrahydro-1H-1,5-methano-3-benzazepin-7-amine | Not more than 0.0438 |
| Mononitro protected | 7-nitro-3-(trifluoroacetyl)-2,3,4,5-tetrahydro-1H-1,5-methano-3-benzazepine | Not more than 0.0438 |
| Metadinitro protected | 6,8-dinitro-3-(trifluoroacetyl)-2,3,4,5-tetrahydro-1H-1,5-methano-3-benzazepine | Not more than 0.0438 |
| Individual unspecified impurity | | Not more than 0.10 |
| Total impurities | | Not more than 1.0 |

Calculation for the limit fixed (Genotoxic)=PDE (μg/day)/MDD (mg/day)=1.5/3.42=0.438 ppm or 0.0438% w/w.

MDD=3.42 mg of Varenicline Tartrate per day

A list of process impurities controlled in varenicline tartrate maltodextrin premix is provided in Table 14.

TABLE 14

List of Process Impurities Controlled in Varenicline Tartrate Maltodextrin Premix

| S. No | Impurities | Limit (% w/w) | Method |
|---|---|---|---|
| 1 | N-Formyl Varenicline | 0.15 | Adopted RS Method-II |
| 2 | Diamide Impurity | 0.15 | |
| 3 | N-Methyl Varenicline | 0.15 | Related Substances |
| 4 | Varenicline-N Glucoside | 0.15 | Method-III |
| 5 | Tartaric acid Monomethyl ester | 0.15 | LCMS-ESI |
| 6 | Tartaric acid Dimethyl ester | 0.15 | LCMS-APCI |
| | Nitrosoamine | | |
| 7 | Nitroso Varenicline Impurity | 5.26 ppm | LCMS Method-I |
| 8 | Dinitro Nitrosamine Impurity | 5.26 ppm | |
| 9 | Diamino Nitrosamine Impurity | 5.26 ppm | LCMS Method-II |

Note:
Process impurity N-formyl Varenicline and Diamide Impurity has been controlled with 0.15% w/w Varenicline Tartrate Maltodextrin premix (1:10) by using Method-II A. Related Substances Method-I for Analyzing Varenicline Base (Stage 3) (RS Method-I)

Related substance By HPLC (Method-I): Waters HPLC system having Alliance 2695 model pump and 2487 or equivalent (UV) detector with Empower chromatographic software or its equivalent.

Reagents: A list of the reagents used in this method is provided in Table 15.

TABLE 15

List of Regents used in Related Substances Method-I

| S. No. | Name of the solvents | Grade | Make |
|---|---|---|---|
| 1 | Diammonium hydrogen phosphate | AR | Merck or its equivalent |
| 2 | Ortho Phosphoric acid (85 %) | AR | Rankem or its equivalent |
| 3 | Methanol | HPLC | JT Baker or its equivalent |
| 4 | Acetonitrile | HPLC | JT Baker or its equivalent |
| 5 | Water | Milli-Q | — |

Chromatographic Parameters:
Column: X Terra C18 (250×4.6) mm, 5.0μ
Detector wavelength: UV at 210 nm
Flow rate: 1.0 mL/min
Injection volume: 30.0 μL
Run time: 70 minutes
Oven temperature: 30° C.
Sample cooler temperature: 7° C.
Elution: Gradient
Diluent: 0.10% v/v Ortho Phosphoric acid:Methanol (95:05) (v/v)
Buffer preparation: Use 0.02 M of di-ammonium hydrogen phosphate solution, pH adjust to 7.00 (+0.05) using dilute orthophosphoric acid.
Preparation of organic modifier: Premix acetonitrile and Methanol in the ratio of (50:50) (v/v).
Mobile Phase-A: Prepare a premixed and degassed mixture of Buffer:Organic modifier (95:5) (v/v)
Mobile Phase-B: Prepare a premixed and degassed mixture of Buffer:Organic modifier (10:90) (v/v)

Gradient Program
Time (min): 0, 5, 15, 20, 35, 45, 55, 60, 70
Mobile phase B (%): 0, 0, 25, 25, 40, 60, 75, 0, 0
Standard Solution: 0.5 μg/ml of Varenicline Tartrate in Diluent. (0.3 μg/ml of Varenicline)
Sample Preparation: 500 μg/ml (Duplicate Preparation)
System Suitability solution: 0.38 μg/ml of both D and F Impurity
System suitability Acceptance Criteria:
a) USP Resolution between D and F is not less than 1.5
b) % RSD of the area of the Varenicline from Six Replicate injection is Not more than 5.0%.

Table 16 provides the retention time (RT) and relative retention time (RRT) of the impurities.

TABLE 16

RT and RRT of the Impurities

| S. No | Name | About RT (mins) | Approximate RRT | RRF | (% w/w) LOD | LOQ |
|---|---|---|---|---|---|---|
| 1 | Impurity-D | 4.4 | 0.32 | 0.79 | 0.004 | 0.013 |
| 2 | Impurity-F | 5.2 | 0.37 | 1.27 | 0.004 | 0.012 |
| 3 | Impurity-C | 7.1 | 0.51 | 0.68 | 0.004 | 0.013 |
| 4 | Varenicline | 13.8 | 1.00 | — | 0.002 | 0.006 |
| 5 | Methyl Varenicline | 16.0 | 1.16 | 2.13 | 0.002 | 0.005 |
| 6 | Varenicline Stage-01 | 25.3 | 1.83 | 1.38 | 0.003 | 0.008 |
| 7 | Varenicline Stage-02 | 33.0 | 2.38 | 1.52 | 0.004 | 0.013 |
| 8 | Varenicline KSM | 47.6 | 3.45 | 0.67 | 0.002 | 0.007 |

Known Impurity (% w/w) : $(A_t/A_s) \times (C_s/C_t) \times 100/RRF$
Where, $A_s$ = Average Area Response of Standard Solution
$A_t$ = Area Response of Sample Solution.
$C_s$ = Standard Concentration in μg/ml
$C_t$ = Sample Concentration in μg/ml
RRF = Relative response of the Impurity.

B. Related Substances Method-II for Analyzing Varenicline Base (Stage 3) (RS Method-II)

Waters HPLC system having Alliance 2695 model pump and 2487 or equivalent (UV) detector with Empower chromatographic software or its equivalent was employed in the analysis.

Reagents: A list of the reagents used in this method is provided in Table 17.

TABLE 17

List of Regents used in Related Substances Method-II

| S. No. | Name of the solvents | Grade | Make |
|---|---|---|---|
| 1 | Ammonium dihydrogen phosphate | AR | Merck or its equivalent |
| 2 | Ortho Phosphoric acid (85 %) | AR | Rankem or its equivalent |
| 3 | Methanol | HPLC | JT Baker or its equivalent |
| 4 | Acetonitrile | HPLC | JT Baker or its equivalent |
| 5 | Water | Milli-Q | — |

Chromatographic Parameters:
Column: Purospher star RP-18 encapped (250×4.6) mm, 5.0 μ
Detector wavelength: UV at 210 nm
Flow rate: 0.8 mL/min
Injection volume: 25.0 μL
Run time: 52 minutes
Column oven temperature: 45° C.
Sample Cooler temperature: 10° C.
Diluent: 0.1% Ortho phosphoric acid v/v:Methanol (85:15) (v/v)

Elution: Gradient
Diluent: 0.10% v/v Ortho Phosphoric acid:Methanol (95:05) (v/v)
Mobile phase-A: Weigh and transfer about 3.45 g of Ammonium dihydrogen orthophosphate in 1000 mL water and add 2.0 ml of orthophosphoric acid 85%, Filtered through 0.45 μm or fine porosity membrane and degass.
Mobile phase-B: Mix Acetonitrile, methanol and water in the ratio of 550:500:50.
Gradient Program
Time (min): 0, 35, 40, 42, 52
Mobile phase B (%): 10, 70, 70, 10, 10
Standard Solution: 0.5 μg/ml of Varenicline Tartrate in Diluent. (0.3 μg/ml of Varenicline)
Sample Preparation: 500 μg/ml (Duplicate Preparation)
System Suitability solution: 0.38 μg/ml of both Impurity G and monoamino protected.
System suitability Acceptance Criteria:
a) USP Resolution between G and monoamino protected is not less than 1.5
b) % RSD of the area of the Varenicline from Six Replicate injection is not more than 5.0%.
Table 18 provides the RT and RRT of the impurities.

$M_2$=Molecular weight of Varenicline Tartrate (361.35 g/mol)

C. Related Substance Method III For Analyzing Varenicline Tartrate Maltodextrin Premix (1:10) (Stage 4) (RS Method-III)

This method is used as a control of N-methyl varenicline and Varenicline-N-glucoside impurity in varenicline tartrate maltodextrin premix (1:10).

Instrumentation: HPLC equipped with UV detector (Waters—Alliance with Empower software or equivalent)
Chromatographic Parameters:
Column: Waters X-Bridge RP Shield C18 or equivalent (Length: 250 mm, Diameter: 4.6 mm, Particle size: 3.5μ)
Detector wavelength: UV at 210 nm
Flow rate: 0.6 mL/min
Injection volume: 25.0
Run time: 45 minutes
Column oven temperature: 45° C.
Sample Cooler temperature: 10° C.
Needle wash: Methanol: water (50:50)
Elution: Gradient
Gradient Program
Time (min): 0, 20, 23, 33, 35, 45

TABLE 18

RT and RRT of the Impurities

| S. No | Name | About RT (mins) | Approximate RRT | RRF | LOD (% w/w) | LOQ (% w/w) |
|---|---|---|---|---|---|---|
| 1 | Impurity-D# | 3.1 | 0.31 | Method-I Impurities | | |
| 2 | Impurity-C# | 3.4 | 0.34 | *Impurity-C, impurity-F | | |
| 3 | Impurity-F# | 3.7 | 0.37 | and tartaric acid are merged in spiked sample preparation | | |
| 4 | Tartaric acid | 3.5 | 0.37* | Tartaric acid content method | | |
| 5 | N-Methyl Varenicline# | 9.26 | 0.94 | Method-III Impurities | | |
| 6 | VarenicclineN-Glucoside# | 9.29 | | | | |
| 7 | Varenicline | 10.1 | 1.00 | 1.00 | 0.002 | 0.005 |
| 8 | Metadiamino protected | 11.9 | 1.17 | 1.56 | 0.003 | 0.009 |
| 9 | Methyl Varenicline# | 12.5 | 1.24 | Method-I Impurity | | |
| 10 | Mononitro deprotected | 12.9 | 1.27 | 0.70 | 0.002 | 0.005 |
| 11 | Metadinitro deprotected | 14.1 | 1.39 | 0.45 | 0.002 | 0.008 |
| 12 | Varenicline Stage-01# | 15.4 | 1.52 | Method-I Impurity | | |
| 13 | Varenicline impurity-G | 15.9 | 1.56 | 0.63 | 0.004 | 0.014 |
| 14 | Monoamino protected | 17.0 | 1.68 | 0.71 | 0.003 | 0.010 |
| 15 | N-Formyl Varenicline | 17.75 | 1.82 | 1.64 | 0.003 | 0.008 |
| 16 | Varenicline Stage-02# | 28.1 | 2.78 | Method-I Impurities | | |
| 17 | Diamide impurity | 29.42 | 3.01 | 1.44 | 0.002 | 0.007 |
| 18 | Varenicline KSM# | 35.2 | 3.48 | Method-I Impurities | | |
| 19 | Mononitro protected | 35.8 | 3.53 | 0.70 | 0.002 | 0.007 |
| 20 | Metadinitro protected | 37.0 | 3.65 | 0.66 | 0.003 | 0.009 |

Note:
In sample chromatograms, disregard the impurities of RS Method I and RS Method III in RS Method II.
Known Impurity (% w/w) : $(A_t/A_s) \times (C_s/C_t) \times 100/RRF$ Where, $A_s$=Average Area Response of Standard Solution
$A_t$=Area Response of Sample Solution.
$C_s$=Standard Concentration in μg/ml
$C_t$=Sample Concentration in μg/ml
RRF=Relative response of the Impurity.
Unspecified Impurity (% w/w): $(A_t/A_s) \times (C_s/C_t) \times 100 \times M_1/M_2$
Where, $A_s$=Average Area Response of Standard Solution
$A_t$=Area Response of Sample Solution.
$C_s$=Standard Concentration in μg/ml
$C_t$=Sample Concentration in μg/ml
$M_1$=Molecular weight of Varenicline free base (211.26 g/mol)

Mobile phase B (%): 10, 35, 90, 90, 10, 10
Buffer: Weigh and dissolve about 2.64 g of di-ammonium hydrogen phosphate in 1000 mL water, adjust the pH to 7.00 (±0.05) using dilute orthophosphoric acid.
Preparation of organic modifier: Premix acetonitrile and Methanol in the ratio of (50:50) (v/v).
Mobile Phase-A: Prepare a premixed and degassed mixture of Buffer:Organic modifier (95:5)(v/v)
Mobile phase-B: Mix Acetonitrile, methanol and water in the ratio of 550:500:50
Diluent: 0.1% OPA:Methanol (85:15) v/v
Standard Solution: Mixture 0.15 μg/ml of both N-Methyl Varenicline and Varenicline-N-Glucoside Impurity Sample Preparation: 550 mg of premix in 50 ml (1000 μg of Varenicline Tartrate/ml (Duplicate Preparation)

System Suitability solution/RT Identification Solution: Varenicline tartrate (1:10) Premix sample solution of 1000 μg/ml Varenicline tartrate containing 0.15 μg/ml of each of Methyl Varenicline, Varenicline-N-Glucoside and meta-di-amino protected impurity.

System Suitability Acceptance Criteria:
a) USP Resolution between Varenicline N-Glucoside and meta-diamino protected is not less than 1.0
b) % RSD of the area of the Varenicline from Six Replicate injection is Not more than 5.0%.

Figure 8A:
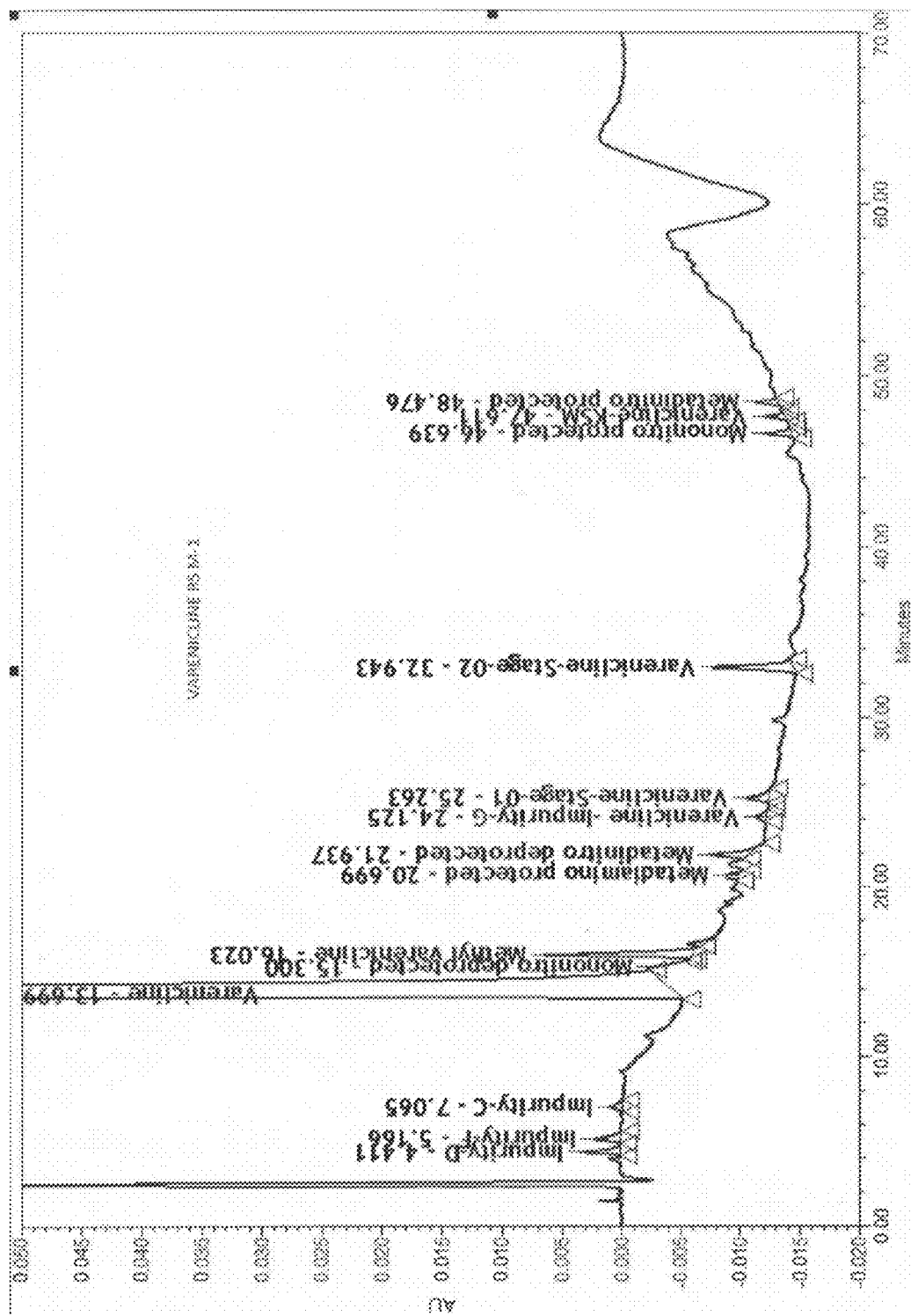
FIG. 8A is a specificity chromatogram of HPLC method: RS METHOD-I.
Figure 8B:
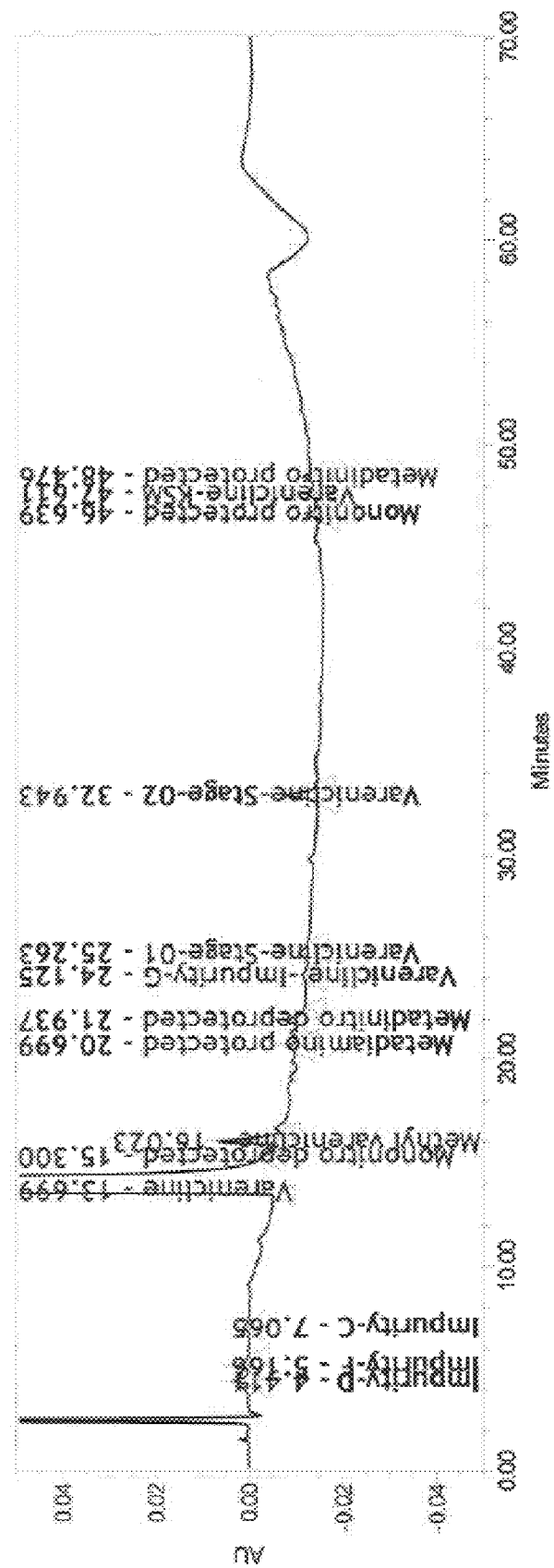
FIGS. 8B-8D are segments of the chromatograph of FIG. 8A. The specificity study chromatogram of the impurities viz. N-methyl Varenicline, Varenicline N-Glucoside in RS METHOD-I are provided in FIG. 8E.
Figure 8C:
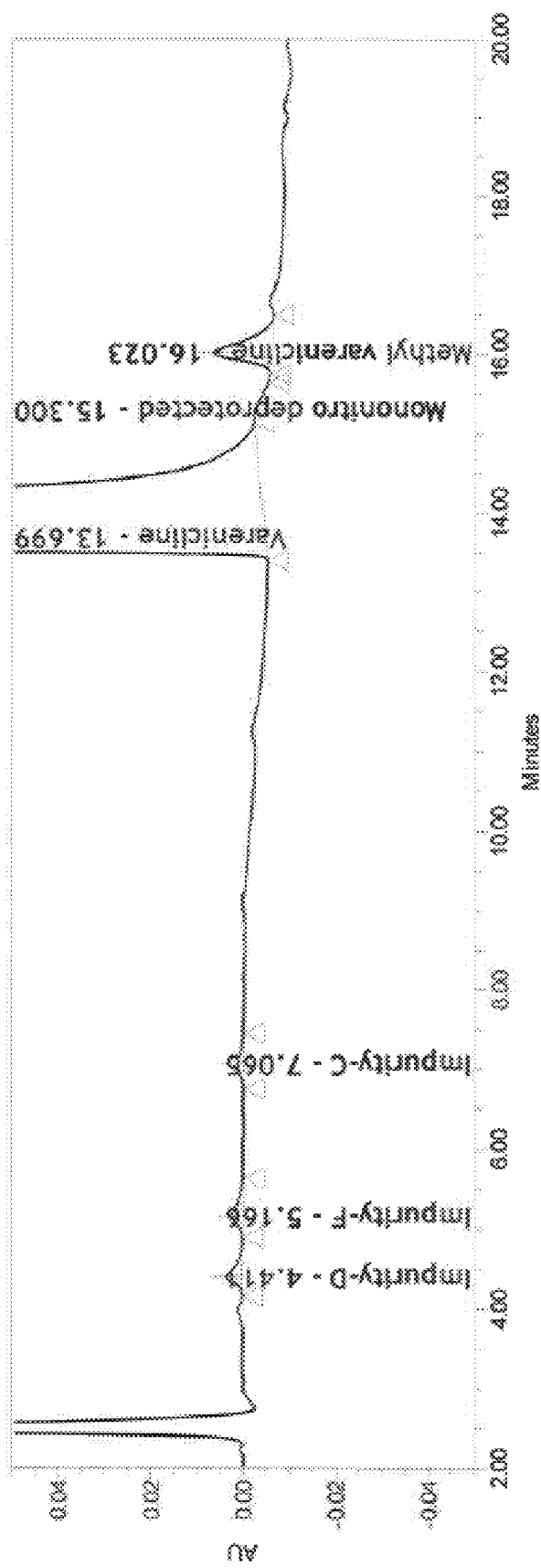
Figure 8D:
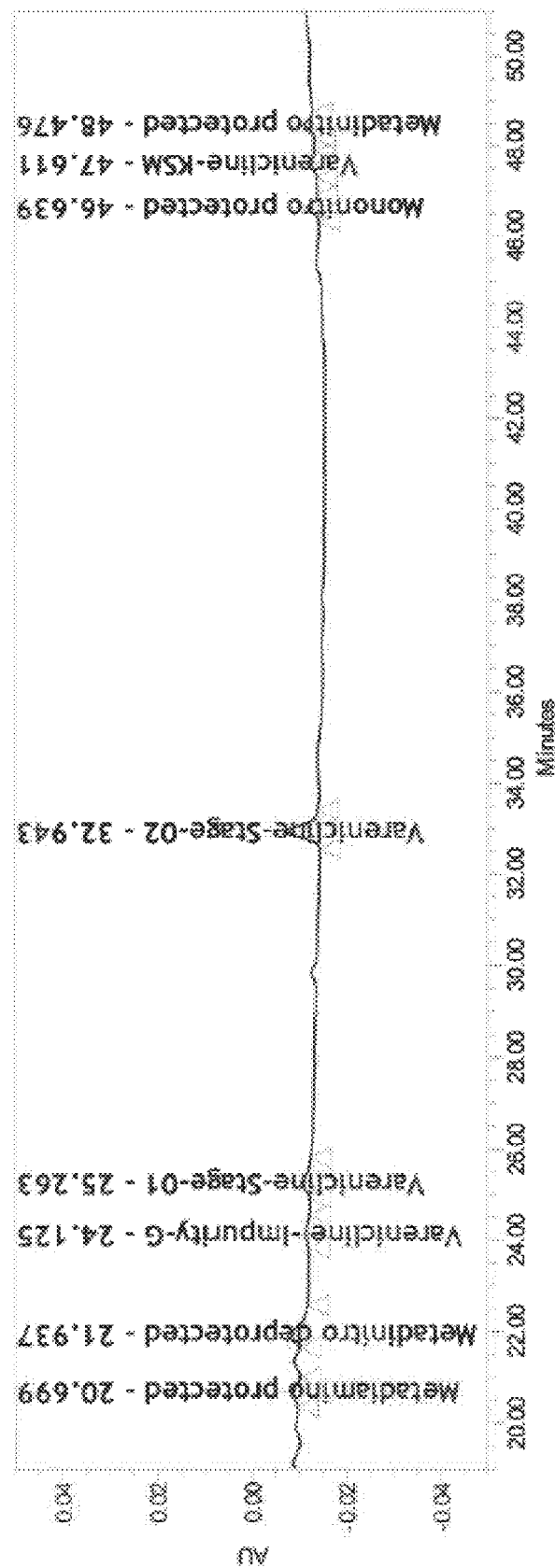
Figure 8E:
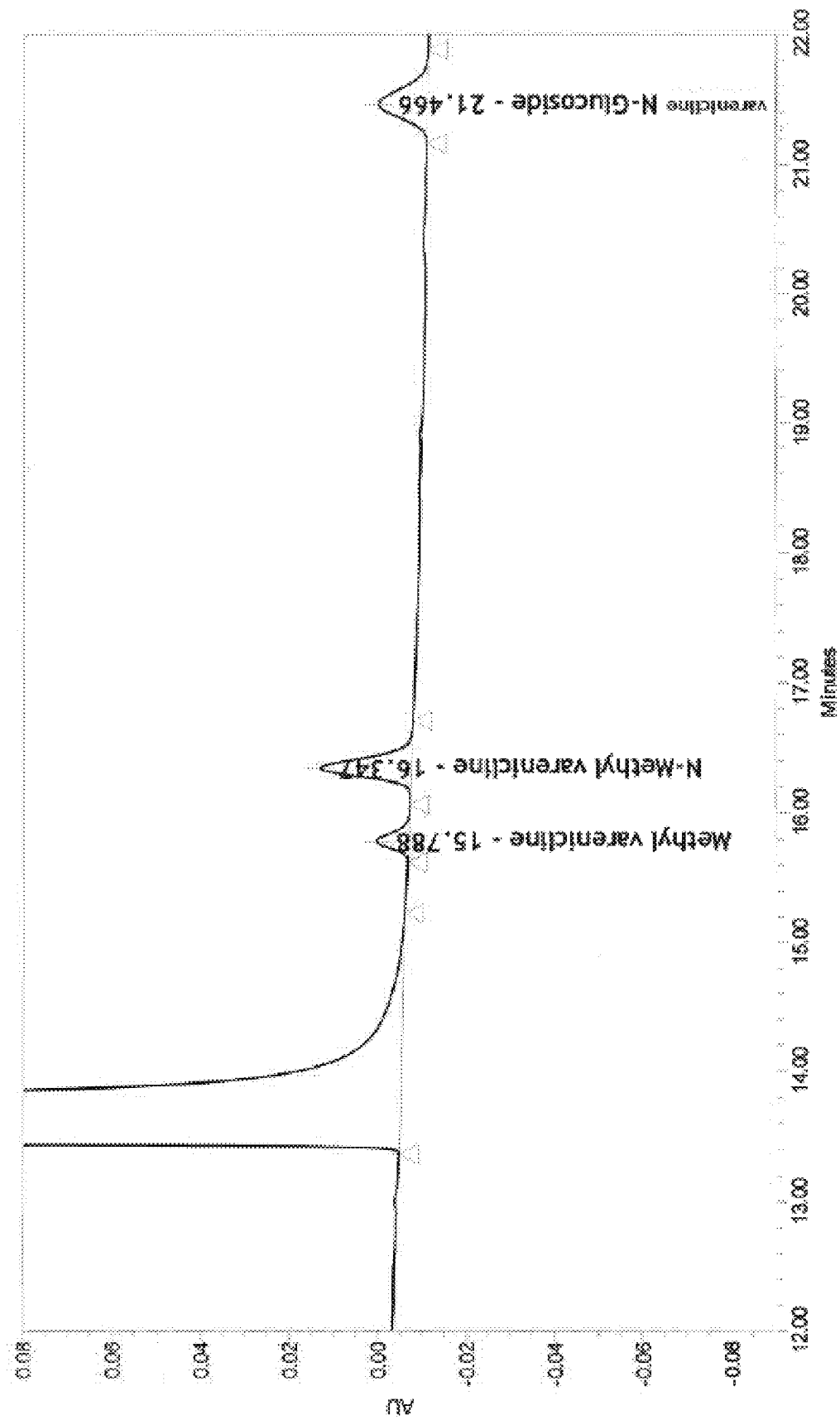
Figure 9A:
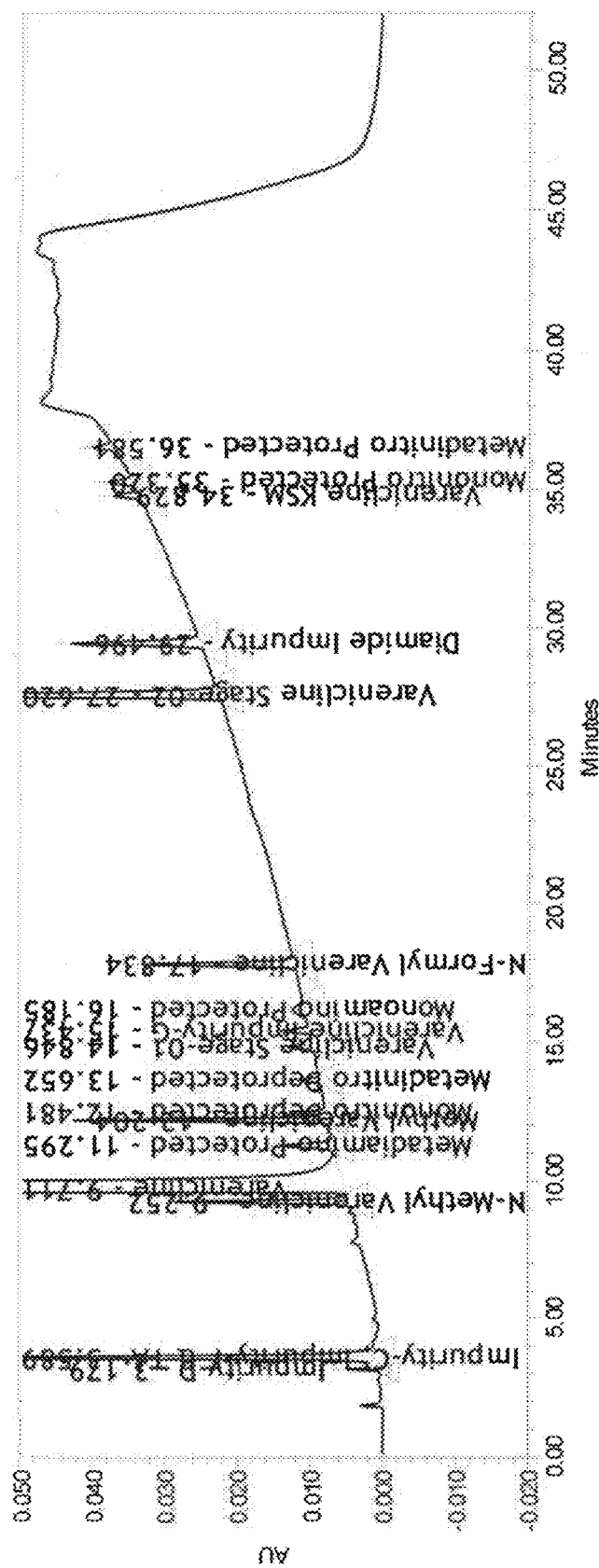
FIG. 9A is a specificity chromatogram of HPLC method: RS METHOD-II.
Figure 9B:
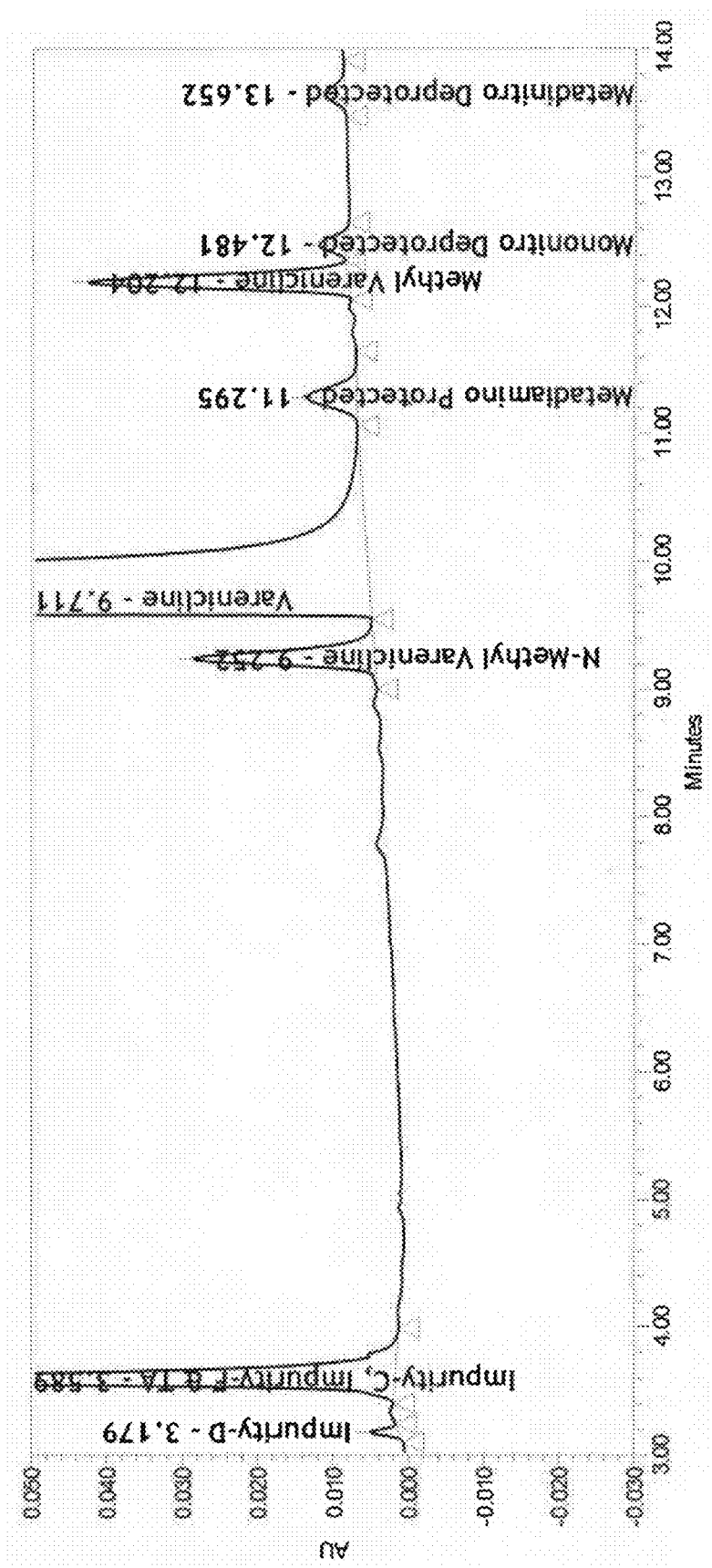
FIG. 9B and FIG. 9C are segments of the chromatograph of FIG. 9A.
Figure 9C:
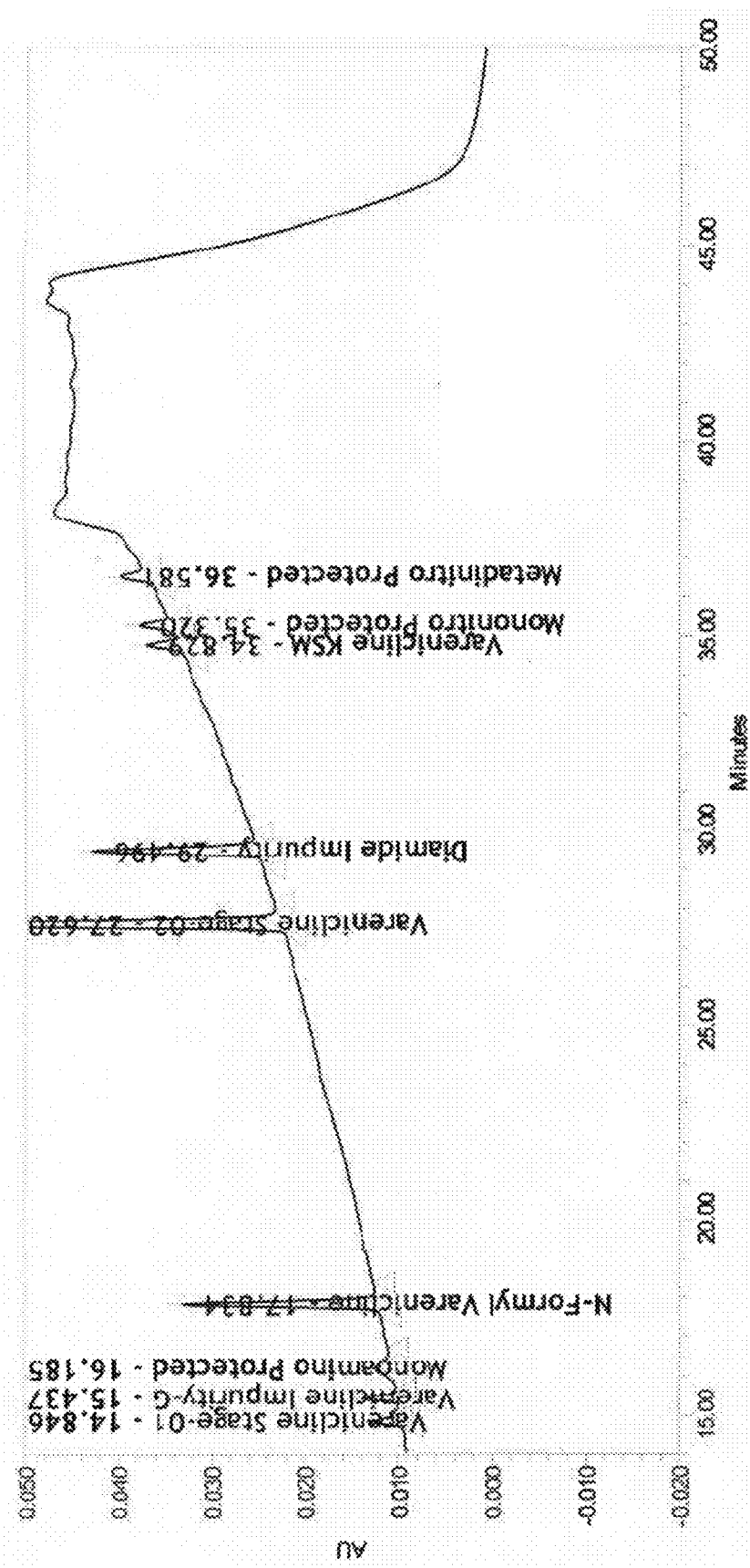
Figure 10A:
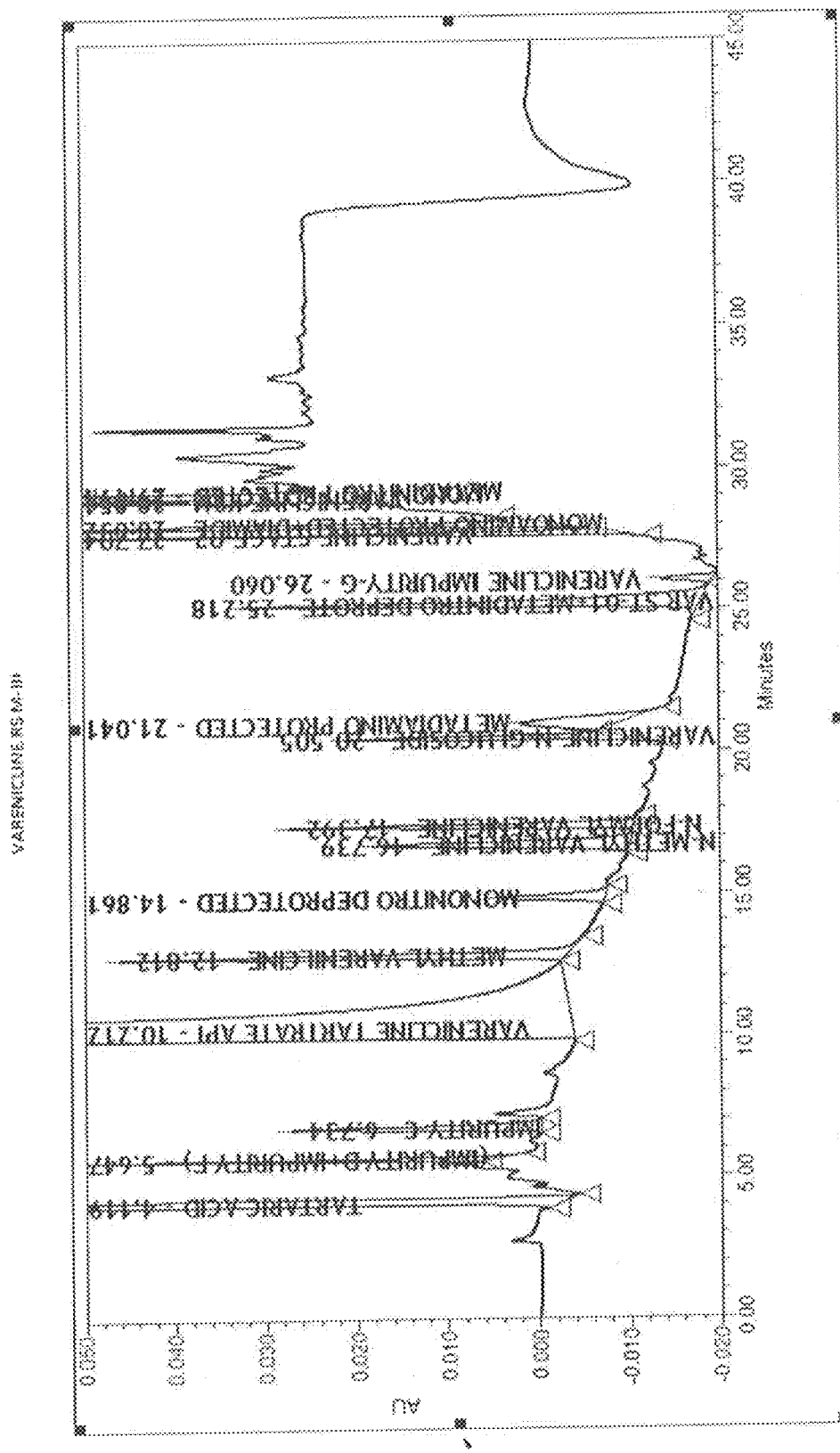
FIG. 10A is a specificity chromatogram of HPLC method: RS METHOD-III.
Figure 10B:
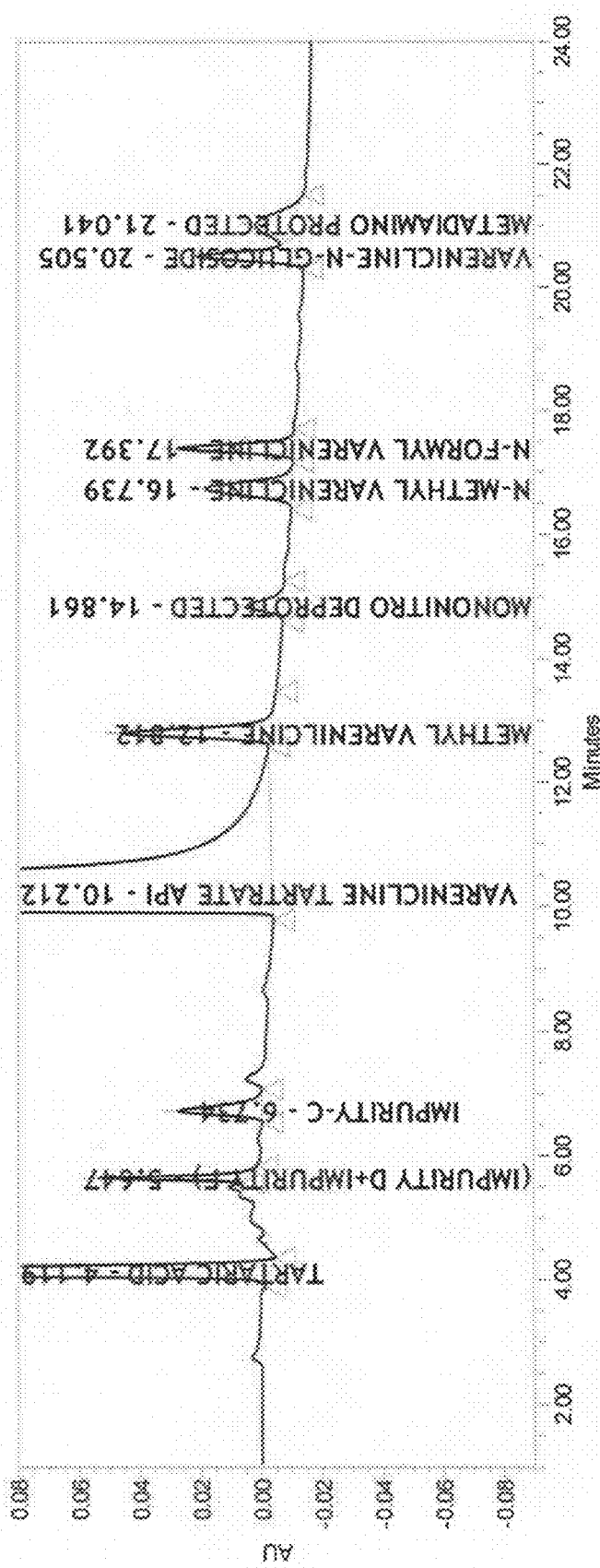
FIG. 10B and FIG. 10C are segments of the chromatograph of FIG. 9A.
Figure 10C:
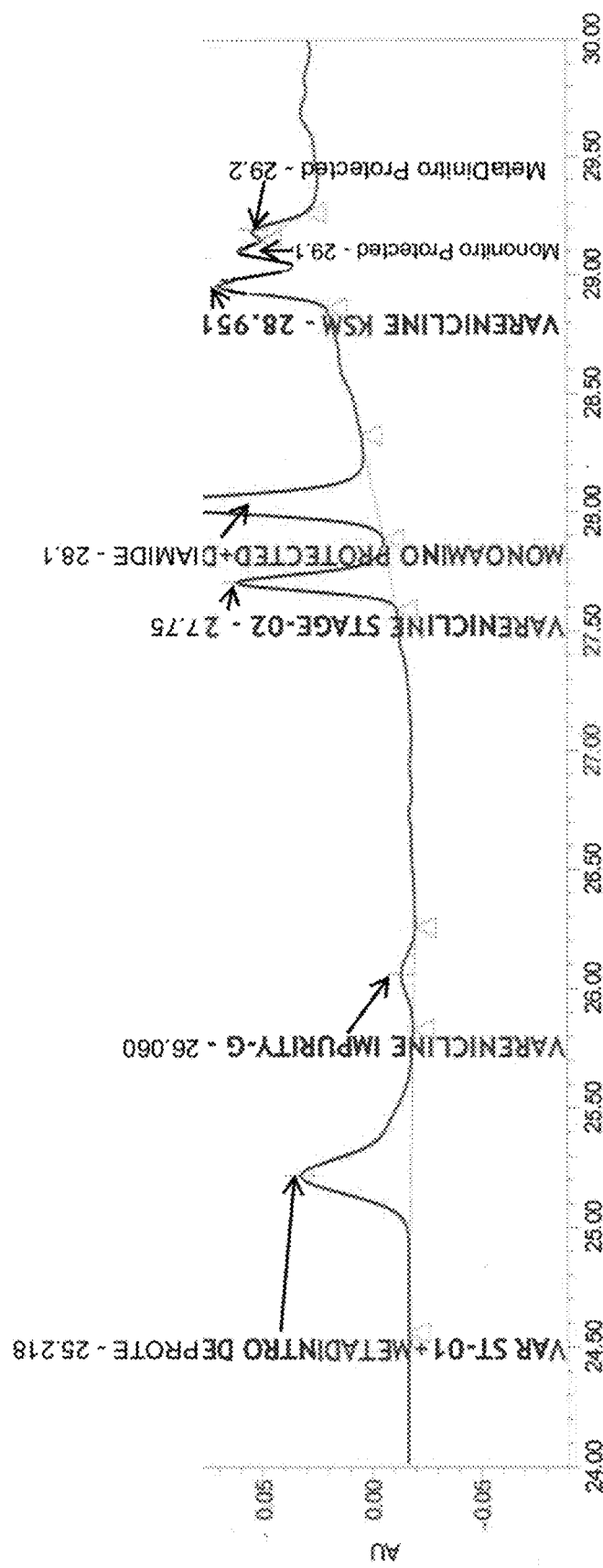

Calculation:
Known Impurity (% w/w): $(A_t/A_s) \times (C_s/C_t) \times 100/9.09 \times 100$ Where, $A_s$=Average Area Response of Standard Solution
$A_t$=Area Response of Sample Solution.
$C_s$=Standard Concentration in μg/ml
$C_t$=Sample Concentration in μg/ml D. RS Method-I, RS Method-II, and RS Method-III for Analyzing the Varenicline Tartrate Maltodextrin Premix API The same three HPLC methods (Related Substances Method-I; Related Substances Method-II; and Related Substances Method-III) were adopted for analyzing the Varenicline Tartrate Maltodextrin Premix API for quantifying the respected impurities. The results are provided in Tables 19-21 and FIGS. 8A-10C. The specificity study chromatogram of the impurities viz. N-methyl Varenicline, Varenicline N-Glucoside in RS method 1 are provided in FIG. 8E.

TABLE 19

RS Method-I (Adopted Method-I of Varenicline Base (Stage-03))

| S. No | Name | About RT (mins) | Approximate RRT | RRF | LOD (% w/w) | LOQ (% w/w) |
|---|---|---|---|---|---|---|
| 1 | Tartaric acid# | 2.4 | 0.18 | | Tartaric acid content method | |
| 2 | Impurity-D | 4.4 | 0.32 | 0.79 | 0.004 | 0.013 |
| 3 | Impurity-F | 5.2 | 0.37 | 1.27 | 0.004 | 0.012 |
| 4 | Impurity-C | 7.1 | 0.51 | 0.68 | 0.004 | 0.013 |
| 5 | Varenicline | 13.7 | 1.00 | — | 0.002 | 0.006 |
| 6 | Mononitro deprotected# | 15.3 | 1.10 | | Method-2 Impurity | |
| 7 | Methyl Varenicline | 16.0 | 1.16 | 2.13 | 0.002 | 0.005 |
| 8 | N-Methyl Varenicline* | 16.3 | 1.19 | | Method-3 Impurity | |
| 9 | N-Formyl Varenicline# | 17.8 | 1.38 | | Method-2 Impurity | |
| 10 | Metadiamino protected# | *ND | ND | | *The above impurities response very low was observed in method-1HPLC condition. | |
| 11 | Metadinitro deprotected# | 21.9 | 1.53 | | | |
| 12 | Varenicline N-Glucoside# | 21.5 | 1.59 | | Method-3 Impurity | |
| 13 | Varenicline impurity-G# | 24.1 | 1.70 | | Method-2 Impurity | |
| 14 | Varenicline Stage-01 | 25.3 | 1.83 | 1.38 | 0.003 | 0.008 |
| 15 | Varenicline Stage-02 | 33.0 | 2.38 | 1.52 | 0.004 | 0.013 |
| 16 | Monoamino protected# | *ND | ND | | Method-2 Impurity | |
| 17 | Diamide impurity# | 29.5 | 2.71 | | | |
| 18 | Mononitro protected# | 46.6 | 3.32 | | | |
| 19 | Varenicline KSM | 47.6 | 3.45 | 0.67 | 0.002 | 0.007 |
| 20 | Metadinitro protected# | 48.5 | 3.47 | | Method-2 Impurity | |

Note:
In sample chromatograms, the impurities of RS Method II and III were disregarded in RS Method I.
*The specificity of the impurities viz. N-methyl Varenicline, Varenicline N-Glucoside in RS Method-I were performed separately. The specificity study chromatograms of the these impurities are provided in FIG. 8E.

TABLE 20

RS Method-II (Adopted Method-II of Varenicline Base (Stage-03)

| S. No | Name | About RT (mins) | Approximate RRT | RRF | LOD (% w/w) | LOQ (% w/w) |
|---|---|---|---|---|---|---|
| 1 | Impurity-D# | 3.2 | 0.31 | | Method-I Impurities | |
| 2 | Impurity-C# | 3.4 | 0.34 | | *Impurity-C, Impurity-F and tartaric acid are merged in spiked sample preparation | |
| 3 | Impurity-F# | 3.7 | 0.37 | | | |
| 4 | Tartaric acid | 3.5 | 0.37* | | Tartaric acid content method | |
| 5 | N-Methyl Varenicline# | 9.3 | 0.94 | | Method-3 Impurities | |
| 6 | Varenicline N-Glucoside# | 20.5 | | | | |
| 7 | Varenicline | 9.7 | 1.00 | 1.00 | 0.002 | 0.005 |
| 8 | Metadiamino protected | 11.3 | 1.17 | 1.56 | 0.003 | 0.009 |
| 9 | Methyl Varenicline# | 12.2 | 1.24 | | Method-I Impurity | |
| 10 | Mononitro deprotected | 12.5 | 1.27 | 0.70 | 0.002 | 0.005 |
| 11 | Metadinitro deprotected | 13.7 | 1.39 | 0.45 | 0.002 | 0.008 |
| 12 | Varenicline Stage-01# | 14.8 | 1.52 | | Method-I Impurity | |
| 13 | Varenicline impurity-G | 15.4 | 1.56 | 0.63 | 0.004 | 0.014 |
| 14 | Monoamino protected | 16.2 | 1.68 | 0.71 | 0.003 | 0.010 |
| 15 | N-Formyl Varenicline | 17.8 | 1.82 | 1.64 | 0.003 | 0.008 |

TABLE 20-continued

RS Method-II (Adopted Method-II of Varenicline Base (Stage-03)

| S. No | Name | About RT (mins) | Approximate RRT | RRF | (% w/w) LOD | LOQ |
|---|---|---|---|---|---|---|
| 16 | Varenicline Stage-02# | 27.6 | 2.78 | | Method-I Impurities | |
| 17 | Diamide impurity | 29.5 | 3.01 | 1.44 | 0.002 | 0.007 |
| 18 | Varenicline KSM# | 34.8 | 3.48 | | Method-I Impurities | |
| 19 | Mononitro protected | 35.3 | 3.53 | 0.70 | 0.002 | 0.007 |
| 20 | Metadinitro protected | 36.6 | 3.65 | 0.66 | 0.003 | 0.009 |

Note:
In sample chromatograms, the impurities of RS Method I and RS Method III were disregarded in RS Method II.

TABLE 21

RS Method-III (Adopted Method-III of Varenicline Base (Stage-03))

| S. No | Name | About RT (mins) | Approximate RRT | (% w/w) LOD | LOQ |
|---|---|---|---|---|---|
| 1 | Tartaric acid# | 4.1 | 0.43 | Tartaric acid content Method | |
| 2 | Impurity-D# | 5.6 | 0.53 | Method-1 Impurities | |
| 3 | Impurity-F# | 5.6 | | | |
| 4 | Impurity-C# | 6.7 | 0.69 | | |
| 5 | Varenicline Tartrate API | 10.2 | 1.00 | — | |
| 6 | Methyl Varenicline # | 12.8 | 1.25 | Method-1 Impurities | |
| 7 | Mononitro deprotected # | 14.9 | 1.46 | Method-2 Impurities | |
| 8 | N-Methyl Varenicline | 16.7 | 1.64 | 0.003 | 0.008 |
| 9 | N-Formyl Varenicline # | 17.4 | 1.70 | Method-2 Impurity | |
| 10 | Varenicline N-Glucoside | 20.5 | 2.02 | 0.003 | 0.008 |
| 11 | Meta diamino protected# | 21.0 | 2.06 | Method-2 Impurity | |
| 12 | Varenicline Stage-01# | 25.2 | 2.47 | Method-1 Impurity | |
| 13 | Meta dinitro deprotected# | 25.2 | | Method-2 Impurities | |
| 14 | Varenicline impurity-G# | 26.1 | 2.55 | | |
| 15 | Varenicline Stage-02# | 27.8 | 2.71 | Method-1 Impurity | |
| 16 | Monoamino protected# | 28.1 | 2.75 | Method-2 Impurities | |
| 17 | Diamide impurity# | 28.1 | | | |
| 18 | Varenicline KSM# | 29.0 | 2.84 | Method-1 Impurity | |
| 19 | Mononitro protected# | 29.1 | 2.85 | Method-2 Impurities | |
| 20 | Meta dinitro protected# | 29.2 | 2.85 | | |

E. Content of Tartaric Acid Monomethyl Ester by LCMS:
Instrumentation: UPLC equipped with MS detector (Waters—Acquity with Mass lynx software and Xevo TQ Mass Detector)
Chromatographic Conditions:

| Column | Acquity UPLC CSH Flouro-phenyl (length: 150 mm, Diameter: 2.1 mm, Particle size: 1.7 µ) |
|---|---|
| Flow rate | 0.3 mL/min |
| Week wash solvent Name(% v/v) | Acetonitrile:water (50:50) |
| Strong wash solvent Name(% v/v) | Acetonitrile:water (90:10) |
| Injection Volume | 5 µl |
| Column oven temperature | 30° C. |
| Sample cooler | 10° C. |
| Elution | Gradient |
| Run time | 17 minutes |

Mass Parameters:

| Start time and end time | 0 to 17 minutes |
|---|---|
| Ionization Mode | ES Negative |
| Data Type | SIR data |
| Function Type | SIR of one channel |
| Scan time (Sec) | 1.00 |
| Data format | Continuum |
| Span (Da) | 0.10 |

SIR

| Channel | Mass (Da) | Dwell(s) | Cone (v) | Compound |
|---|---|---|---|---|
| 1 | 163.03 | 0.025 | 18 | Tartaric acid Monomethyl ester |

Tune Method

| Polarity | ES Negative |
|---|---|
| Capillary voltage | 3 Kilo volt |
| Cone-Voltage | 18 volt |
| Source temperature | 150° C. |
| Desolvation temperature | 400° C. |

| | |
|---|---|
| Desolvation Gas Flow | 800 (L/Hr) |
| Cone Gas Flow | 50 (L/Hr) |

Mass divert Program:

| Event | Retention time (RT) mins | Flow state |
|---|---|---|
| 1 | 0.00 | Waste |
| 2 | $(RT_s - 1)$ | Waste |
| 3 | $(RT_s - 1) + 0.01$ | LC |
| 4 | $(RT_s + 1.5)$ | LC |
| 5 | $(RT_s + 1.51)$ | Waste |

Gradient Program:

| Time (mins) | Mobile Phase-A (%) | Mobile Phase-B (%) |
|---|---|---|
| Initial | 90 | 10 |
| 4.00 | 90 | 10 |
| 8.00 | 20 | 80 |
| 11.00 | 20 | 80 |
| 12.00 | 90 | 10 |
| 17.00 | 90 | 10 |

Mobile Phase A: 0.1% Formic acid in water. (1 ml in 1000 ml water)
Mobile Phase B: Acetonitrile
Diluent: 0.1% Formic acid in water:Acetonitrile (90:10)% v/v
Standard solution: 0.002% concentration in diluent
Sample Preparation: 15 mg/ml in diluent

| | Concentration (% w/w) | |
|---|---|---|
| | LOD | LOQ |
| Tartaric acid Monomethyl ester | 0.005 | 0.015 |

Calculation:
Content of Tartaric acid Monomethyl ester (% w/w)

$$\frac{A_2}{A_1} \times \frac{W_1}{W2} \times \frac{100}{Y} \times 106$$

Where:
$A_2$=Peak area of Tartaric acid Monomethyl ester impurity in sample
$A_1$=Average Peak area Tartaric acid Monomethyl ester impurity in standard
$W_1$=standard concentration
$W_2$=Sample concentration
P=Purity of Tartaric acid Monomethyl ester impurity standard
Y=9.09 (i.e. Theoretical Label claim of Varenicline tartrate in Varenicline Tartrate Maltodextrin Premix (1:10) in %)
F. Content of Tartaric Acid Dimethyl Ester by LCMS:
Instrumentation: UPLC equipped with MS detector (Waters—Acquity with Mass lynx software and Xevo TQ Mass Detector)
Chromatographic Conditions:

| | |
|---|---|
| Column | Acquity UPLC BEH C18 (length: 150 mm, Diameter: 2.1 mm, Particle size: 1.7μ) |
| Flow rate | 0.3 mL/min |
| Week wash solvent Name (% v/v) | Acetonitrile: water (50:50) |
| Strong wash solvent Name (% v/v) | Acetonitrile: water (90:10) |
| Injection Volume | 5 μl |
| Column oven temperature | 40° C. |
| Sample cooler | 10° C. |
| Elution | Gradient |
| Run time | 15 minutes |

Mass Parameters:

| | |
|---|---|
| Start time and end time | 0 to 15 minutes |
| Ionization Mode | API+ |
| Data Type | SIR data |
| Function Type | SIR of one channel |
| Scan time (Sec) | 1.00 |
| Data format | Continuum |
| Span (Da) | 0.20 |

SIR

| Channel | Mass (Da) | Dwell(s) | Cone (v) | Compound |
|---|---|---|---|---|
| 1 | 179.04 | 0.150 | 12 | Tartaric acid Dimethyl ester |

Tune Method

| | |
|---|---|
| Polarity | API Positive |
| Corona(kV) | 3.5 Kilo volt |
| Cone(V) | 12 volt |
| Source temperature (° C.) | 150° C. |
| Probe temperature (° C.) | 550° C. |
| Desolvation Gas Flow | 1000 (L/Hr) |
| Cone Gas Flow | 50 (L/Hr) |

Mass divert Program:

| Event | Retention time (RT) mins | Flow state |
|---|---|---|
| 1 | 0.00 | Waste |
| 2 | $(RT_s - 1)$ | Waste |
| 3 | $(RT_s - 1) + 0.01$ | LC |
| 4 | $(RT_s + 1.5)$ | LC |
| 5 | $(RT_s + 1.51)$ | Waste |

Gradient Program:

| Time (mins) | Mobile Phase-A (%) | Mobile Phase-B (%) |
|---|---|---|
| Initial | 95 | 5 |
| 5.00 | 95 | 5 |
| 6.00 | 5 | 95 |
| 9.00 | 5 | 95 |
| 10.00 | 95 | 5 |
| 15.00 | 95 | 5 |

Mobile Phase A: 0.1% Formic acid in water. (1 ml in 1000 ml water)
Mobile Phase B: Acetonitrile
Diluent: 0.1% Formic acid in water:Acetonitrile (90:10) % v/v
Standard solution: 0.002% concentration in diluent
Sample Preparation: 15 mg/ml in diluent

| | Concentration (% w/w) | |
|---|---|---|
| | LOD | LOQ |
| Tartaric acid Dimethyl ester | 0.0015 | 0.0046 |

Calculation:

$$\frac{A_2}{A_1} \times \frac{W_1}{W_2} \times \frac{100}{Y} \times 10^6$$

Where:
$A_2$=Peak area of Tartaric acid Dimethyl ester impurity in sample
$A_1$=Average Peak area of Tartaric acid Dimethyl ester impurity in standard
$W_1$=standard concentration
$W_2$=sample concentration
$Y$=9.09 (i.e. Theoretical Label claim of Varenicline tartrate in Varenicline Tartrate Maltodextrin Premix (1:10) in %)

G. Nitrosamine Content by LCMS Method-I:
Instrumentation: UPLC equipped with Mass detector(Waters—UPLC equipped with XEVO-TQ MS Detector with Mass lynx software or Equivalent)

Chromatographic Conditions:

| Column | Zorbax Eclipse Plus C18 (length: 50 mm, Diameter 4.6 mm, Particle size: 1.8μ) |
|---|---|
| Flow rate | 1.0 mL/min |
| Week wash solvent Name(% v/v) | Methanol:water (50:50) |
| Strong wash solvent Name(% v/v) | Methanol:water (90:10) |
| Injection Volume | 6 μl |
| Column oven temperature | 30° C. |
| Sample cooler | 10° C. |
| Elution | Gradient |
| Run time | 15 minutes |

Mass Parameters:

| | |
|---|---|
| Start time and end time | 0 to 15 minutes |
| Ionization Mode | ESI+ |
| Data Type | MRM data |
| Function Type | MRM of 7 Daughters |
| Scan time (Sec) | 1.00 |
| Data format | Continuum |
| Span (Da) | 0.20 |

MRM for Parent Mass 240.97

| Channel | Daughter Mass (Da) | Dwell(s) | Collision energy (v) | Cone Volt | Compound |
|---|---|---|---|---|---|
| 1 | 169.01 | 0.025 | 22 | 20 | Nitroso Varenicline impurity |
| 2 | 181.10 | 0.025 | 32 | 20 | Nitroso Varenicline impurity |
| 3 | 194.05 | 0.025 | 20 | 20 | Nitroso Varenicline impurity |

MRM for Parent Mass 278.99

| Channel | Daughter Mass (Da) | Dwell(s) | Collision energy (v) | Cone Volt | Compound |
|---|---|---|---|---|---|
| 1 | 127.16 | 0.025 | 38 | 34 | Dinitro Nitrosamine impurity |
| 2 | 156.05 | 0.025 | 30 | 34 | Dinitro Nitrosamine impurity |
| 3 | 202.11 | 0.025 | 24 | 34 | Dinitro Nitrosamine impurity |
| 4 | 232.03 | 0.025 | 20 | 34 | Dinitro Nitrosamine impurity |

Tune Method

| Polarity | ESI Positive |
|---|---|
| Capillary Volt (KV) | 3.5 |
| Cone (V) | 32 |
| Dissolvation temperature (° C.) | 600° C. |
| Source Temperature (° C.) | 150° C. |
| Dissolvation Gas flow (L/Hr) | 1200 |
| Cone Gas Flow (L/Hr) | 120 |
| Collision Gas flow (L/Hr) | 0.15 |
| Extractor (V) | 3.0 |

Mass divert Program:

| Event | Retention time (RT) mins | Flow state |
|---|---|---|
| 1 | 0.00 | Waste |
| 2 | (RT of Nitroso Varenicline impurity − 0.5) | Waste |
| 3 | (RT of Nitroso Varenicline impurity − 0.5) + 0.01 | LC |
| 4 | (RT of Dinitro Nitrosamine impurity + 0.5) | LC |
| 5 | (RT of Dinitro Nitrosamine impurity + 0.5) + 0.01 | Waste |

Gradient Program:

| Time (mins) | Mobile Phase-A (%) | Mobile Phase-B (%) |
|---|---|---|
| 0.01 | 90 | 10 |
| 0.50 | 90 | 10 |
| 7.00 | 10 | 90 |
| 10.00 | 10 | 90 |
| 11.00 | 90 | 10 |
| 15.00 | 90 | 10 |

Mobile Phase A: 0.2% Formic acid in water. (2 ml in 1000 ml water)
Mobile Phase B: Methanol
Diluent: Methanol
Standard solution: 0.000163% conc in diluent
Sample Preparation: 200 mg/ml in diluent and sonicate for 3 minute and filter
Nitroso Varenicline impurity: Parent mass 240.97 three fragments are 169.01, 181.0 and 194.05.
Dinitro Nitrosamine impurity: Parent mass 278.99 Four Fragments are 127.16, 156.05, 202.11 and 232.03.

| S. No. | Name of impurity | Retention time (mins) | LOQ (ppm) | LOD (ppm) |
|---|---|---|---|---|
| 1 | Nitroso Varenicline impurity | 3.60 | 0.032 | 0.009 |
| 2 | Dinitro Nitrosamine impurity | 4.21 | 0.031 | 0.009 |

Calculation:
i) Nitroso impurity content in ppm (used for both Varenicline Nitrosamine impurity and Dinitro nitrosamine impurity)

$$\frac{A_2}{A_1} \times \frac{W_1}{W_2} \times \frac{100}{Y} \times 10^6$$

Where:
$A_2$=Sum of peak area of Nitroso Varenicline impurity/ Dinitro Nitrosamine impurity in sample
$A_1$=Sum of Average Peak area Nitroso Varenicline impurity/ Dinitro Nitrosamine impurity in standard
$W_1$=standard conc of Nitroso Varenicline impurity/Dinitro Nitrosamine impurity standard
$W_2$=Sample concentration
P=Purity of Nitroso Varenicline impurity/Dinitro Nitrosamine impurity standard
Y=9.09 (i.e. Theoretical Label claim of Varenicline tartrate in Varenicline Tartrate Maltodextrin Premix (1:10) in %)
Nitroso Varenicline impurity: Parent mass 240.97 three fragments are 169.01, 181.0 and 194.05.
Dinitro Nitrosamine impurity: Parent mass 278.99 Four Fragments are 127.16, 156.05, 202.11 and 232.03.

H. Nitrosamine Content by LCMS Method-II
Instrumentation: UPLC equipped with Mass detector (Waters—UPLC equipped with XEVO-TQ MS Detector with Mass lynx software or Equivalent)

Chromatographic Conditions:

| Column | AQUASIL C18 (length: 100 mm, Diameter 4.6 mm, Particle size: 3.0µ) Part No: 77503-104630 |
|---|---|
| Flow rate | 0.8 mL/min |
| Week wash solvent Name (% v/v) | 0.1% Formic acid in Acetonitrile:water (50:50) |
| Strong wash solvent Name (% v/v) | 0.1% Formic acid in Acetonitrile:water (90:10) |
| Injection Volume | 7 µl |
| Column oven temperature | 30° C. |
| Sample cooler | 10° C. |
| Elution | Gradient |
| Run time | 20 minutes |

Gradient Program:

| Time (mins) | Mobile Phase-A (%) | Mobile Phase-B (%) |
|---|---|---|
| 0.01 | 80 | 20 |
| 5.00 | 80 | 20 |
| 7.00 | 5 | 95 |
| 14.00 | 5 | 95 |
| 15.00 | 80 | 20 |
| 20.00 | 80 | 20 |

Mass Parameters:

| | |
|---|---|
| Start time and end time | 0 to 20 minutes |
| Ionization Mode | ESI+ |
| Data Type | MRM data |
| Function Type | MRM of 2 Daughters |
| Scan time (Sec) | 1.00 |
| Data format | Continuum |
| Span (Da) | 0.20 |

MRM for Parent Mass 218.97

| Channel | Daughter mass (Da) | Dwell(s) | Collision energy | Cone volt | Compound |
|---|---|---|---|---|---|
| 1 | 145.86 | 0.025 | 16.00 | 30.00 | Diamino Nitrosamine |
| 2 | 188.98 | 0.025 | 10.00 | 30.00 | Diamino Nitrosamine |

Tune Method

| Polarity | ESI Positive |
|---|---|
| Capillary Volt (KV) | 0.35 |
| Cone (V) | 30 |
| Desolvation temperature (° C.) | 550° C. |
| Source Temperature (° C.) | 150° C. |
| Desolvation Gas flow (L/Hr) | 1200 |
| Cone Gas Flow (L/Hr) | 120 |
| Collision Gas flow (L/Hr) | 0.15 |
| Extractor (V) | 5.0 |

Mass divert Program:

| Event | Retention time (RT) mins | Flow state |
|---|---|---|
| 1 | 0.00 | Waste |
| 2 | (RT of Diamino Nitrosamine impurity − 1.4) | Waste |
| 3 | (RT of Diamino Nitrosamine impurity − 1.4) + 0.01 | LC |
| 4 | (RT of Diamino Nitrosamine impurity + 1.4) | LC |
| 5 | (RT of Diamino Nitrosamine impurity + 1.4) + 0.01 | Waste |

Mobile Phase A: 0.01 M Ammonium formate in water. (0.63 gm in 1000 mL water)

Mobile Phase B: 0.1% Formic acid in methanol (1.0 mL of formic acid in 1000 mL methanol)

Diluent: Acetonitrile 100%
Standard solution: 0.000069% concentration in diluent
Sample Preparation: 150 mg/ml in diluent and sonicate for 3 minute and filter
Diamino Nitrosamine: Parent mass 218.97 two fragments are 145.86 and 188.98.

Injection sequence: (for RT identification)

| S. No. | Name of solution | No. of injections |
|---|---|---|
| 1 | Blank | 1 |
| 2 | Standard Preparation | 1 |

Injection sequence:

| S. No. | Name of solution | No. of injections |
|---|---|---|
| 1 | Blank | 2 |
| 2 | Standard Solution | 6 |
| 3 | Blank | 1 |
| 4 | Sample Preparation | 2 |
| 6 | Blank | 1 |
| 7 | Standard Solution (for bracketing) | 1 |

The retention time of Diamino Nitrosamine impurity is as below.

| Name of Compound | About RT(min) | LOD in ppm | LOQ in ppm |
|---|---|---|---|
| Diamino Nitrosamine impurity | 6.09 | 0.009 | 0.03 |

Calculation: For Diamino Nitrosamine impurity content in ppm $$\frac{A_2}{A_1} \times \frac{W_1}{W_2} \times \frac{100}{Y} \times 10^6$$

Where:
$A_2$ = Peak area of Diamino Nitrosamine impurity in sample
$A_1$ = Average Peak area Diamino Nitrosamine impurity in standard
$W_1$ = standard conc of Nitroso Varenicline impurity/Dinitro Nitrosamine impurity standard
$W_2$ = Sample concentration
P = Purity of Diamino Nitrosamine impurity standard
Y = 9.09 (i.e. Theoretical Label claim of Varenicline tartrate in Varenicline Tartrate Maltodextrin Premix (1:10) in %)

Discussion:

Two Related Substance methods by HPLC were developed for analyzing Varenicline base (Stage 3) for quantifying all impurities of having a similar chromophore of Varenicline. The same two HPLC methods were adopted for analyzing the Varenicline Tartrate Maltodextrin Premix API for quantifying the respected impurities. A third additional RS method by HPLC was developed for analyzing two additional impurities viz. N-methyl Varenicline and Varenicline-N-Gluoside which could form due to reaction of degradation products of Maltodextrin with Varenicline.

Two LCMS methods were developed for analyzing monomethyl and dimethyl esters of tartaric acid as impurities in Varenicline Tartrate Maltodextrin premix API.

Two LCMS methods were developed for quantifying the nitrosamine impurities in Varenicline Tartrate Maltodextrin Premix API.

All the impurities were prepared and qualified by applicant. Also all the above analytical methods were developed and validated by applicant.

Three possible nitrosamine impurities should be controlled in the Varenicline Tartrate Maltodextrin Premix API. However, FDA's published method controls only varenicline nitrosamine impurity.

FDA's method is used for analyzing plain API of Varenicline Tartrate. In contrast, the API analyzed in Example 8 is Varenicline Tartrate Maltodextrin Premix API (1:10). The Premix API contains only about 10% w/w Varenicline Tartrate drug substance. This is a major challenge that was faced for developing method in analyzing nitrosamine impurities in the instant Premix API.

A comparison and advantages of applicant's method (disclosed in Example 8 above) over FDA's method for analyzing nitrosamines is provided in Table 22.

TABLE 22

Comparison and Advantages of in-house versus FDA Method for Nitrosamines

| S.No | Parameter | In-house | FDA Method |
|---|---|---|---|
| 1 | Instrument | LCMS/MS | LC-HRMS |
| 2 | Nitrosamine Method | Two methods were developed for analyzing three nitrosamines viz. dinitro nitrosamine, diamino nitrosamine and Varenicline Nitrosamine. | Method is suitable for only Varenicline Nitrosamine. |
| 3 | Detector Mode ESI | Extracted daughter ions from parent ion Mass 240.97 (MRM mode). Daughter Mass (Da).169.01,181.10,194.05. Multiple reaction monitoring (MRM) offers significant improvements for the screening and confirmation of molecules, especially in more complex matrices. | Extracted parent ion m/z 241.1084 (SIM mode) for Varenicline Nitrosamine. Selected ion monitoring (SIM) is suitable for the screening and confirmation of molecules in relatively simple matrices. |
| 4 | Analytical method Validation | Both methods were validated as per ICH Q2 R1 and demonstrated that it Is suitable for its intended purpose. Linearity range was achieved from LOQ to 7.5 ppm. | Partially validated like LOD & LOQ. Linearity range LOQ of 1.0 to 200 ppm. |
| 5 | LOD/LOQ value | Achieved LOD/LOQ of 0.01 ppm & 0.03 ppm respectively for all nitrosamine. The guideline recommended to achieve LOQ of 0.03 ppm for nitrosamines | reported LOD is 0.2 ppm & LOQ value is 1.0 ppm for Varenicline nitrosamine. |

TABLE 22-continued

Comparison and Advantages of in-house versus FDA Method for Nitrosamines

| S.No | Parameter | In-house | FDA Method |
|---|---|---|---|
| 6 | Spec Limit | Suitable for the limit NMT 5.26 ppm for each nitrosamine and total nitrosamine limit NMT 7.74 ppm. | Limit was not provided. |

Example 9

Preparation of 1-(4,5-Diamino-10-Aza-Tricyclo [6.3.1.0$^{2,7}$]Dodeca-2(7),3,5-Trien-10-YL)-2,2,2-Trifluoro-Ethanone 1-(4,5-Dinitro-10-aza-tricyclo[6.3.1.0$^{2,7}$]dodeca-2(7),3,5-trien-10-yl)-2,2,2-trifluoroethanone (100.0 g, 0.2896 mole) was hydrogenated in methanol (1000 mL) under hydrogen (0.5-1.0 kg/cm$^2$) atmosphere in the presence of 10% Palladium on carbon (10.0 g, 50% wet). After 3 hours, the reaction mass was analyzed by qualitative HPLC to confirm the completion of the reaction. Thereafter, the reaction mass was filtered through celite pad and rinsed with methanol (100 ml). The filtrate was concentrated completely at 30-35° C. under reduced pressure. Hexanes was added to the concentrated mass and distilled completely 30-35° C. under reduced pressure to remove traces of methanol. The mass was stirred with hexanes, the precipitated solid was filtered and washed with hexanes. The wet material was dried at 40-45° C. under reduced pressure for 8 hours. Yield: 82.0 g (100%).

Example 10

Preparation of 1-(5,8,14-Triazatetracyclo[10.3.1.0 2,11.0.4,9]Hexadeca-2(11),3,5,7,9-Pentaene)-2,2,2-Trifluoro-Ethanone The mixture of 1-(4,5-Diamino-10-aza-tricyclo[6.3.1.02,7]dodeca-2(7),3,5-trien-10-yl)-2,2,2-trifluoro-ethanone (73.0 g, 0.256 mole), methanol (146 mL) and water (146 mL) were treated with 40% aqueous glyoxal (40.88 g, 0.2816 mole) and aqueous solution of sodium bisulfate (58.58 g, 0.563 mole in 117.5 mL of water) at 55-60° C. for 3 hours. Thereafter, cooled the mass to 20-30° C., water (730 mL, 10.0 volume) was added and stirred at 20-30° C. for 2 hours. The obtained solid was filtered and slurry washed with water. The semi-dried crude product was crystallized from methanol. Yield: 58.0 g.

Example 11

Preparation of 7,8,9,10-Tetrahydro-6,10-Methano-6H-Pyrazino[2, 3-H][3]Benzazepine: (Varenicline Free Base)

1-(5,8,14-triazatetracyclo[10.3.1.0 2,11.0.4,9] hexadeca-2(11),3,5,7,9-pentaene)-2,2,2-trifluoroethanone is deprotected using sodium carbonate in 50% aqueous methanol to give 7,8,9,10-tetrahydro-6,10-methano-6H-pyrazino[2, 3-h][3] benzazepine (Varenicline free base).

Thus, 1-(5,8,14-triazatetracyclo[10.3.1.0 2,11.0.4,9] hexadeca-2(11),3,5,7,9-pentaene)-2,2,2-trifluoroethanone (48.0 g, 0.1562 mole) in methanol (290 mL) was stirred with aqueous Sodium carbonate solution (33.12 g in 300 mL of water) at 65-70° C. for 3 hours. The reaction mass was filtered and the residue was washed with methanol (48.0 mL).

The combined filtrate was concentrated at 30-35° C. under reduced pressure. The concentrated reaction mass was saturated with sodium chloride and extracted with methylene dichloride. The organic layer was washed with 25% brine solution and treated with activated carbon (5.0 g). The organic layer was concentrated at 30-35° C. to oily mass and co-distilled at 30-35° C. with methyl tert-butyl ether (96 mL) to remove traces of Methylene dichloride. Methyl tert-butyl ether (192 mL) was added to the concentrated mass and stirred at 5-10° C. for 3 hours. The product was isolated by filtration and washed with chilled methyl tert-butyl ether twice. The wet material is dried at 35-40° C. under vacuum. Yield: 27.5 g.

A. General Procedure for the Purification Varenicline Free Base Using Organic or Inorganic Acid:

A solution of Varenicline free base (100.0 g, 0.4733 mol) in methylene dichloride (500 mL, 5.0 vol) was stirred with the aqueous solution of organic or Inorganic acid (1.2 eq, 500 mL of water, 5.0 vol) for 30 min at 25-30° C. The aqueous layer containing corresponding Varenicline salt solution was separated and stirred with methylene dichloride (2×250 mL) to remove nitrosamine impurity by solvent extraction. Thereafter, the aqueous layer was basified (pH 8.5 to 9.5) with aqueous Sodium carbonate solution (2.2 eq in 8.0 volume of water) and extracted the free varenicline base three times with methylene dichloride (3×10.0 volume). The combined organic layer was washed with brine solution and treated with activated carbon (2.0 g). The organic layer was concentrated to oily mass and co-distilled with methyl tert-butyl ether to remove traces of methylene dichloride. methyl tert-butyl ether (80 mL, 4.0 volume) was added to the concentrated mass and stirred at 5-10° C. for 3 hours. The product was isolated by filtration and washed with chilled methyl tert-butyl ether by twice. The wet material was dried at 40° C. under vacuum. Yield: 62.0 g

Example 12

Purification of Varenicline Free Base Using L-(+)-Tartaric Acid

A solution of Varenicline free base (50.0 g) in methylene dichloride (250 mL) was stirred with the aqueous solution of L-(+)-Tartaric acid (1.2 eq, 39.08 g in 250 mL of water). The aqueous layer containing Varenicline tartrate salt was stirred with methylene dichloride (3×150 ml) to remove the nitrosamine impurity by solvent extraction. Thereafter, follow the general procedure for the isolation of Varenicline base from the aqueous layer. Yield: 31.00 g.

Example 13

Purification of Varenicline Free Base Using Fumeric Acid

A solution of Varenicline free base (20.0 g) in methylene dichloride (100 mL) was stirred with the aqueous solution of Fumaric acid (13.18 g, 1.2 eq in 100 mL of water). The aqueous layer containing Varenicline fumarate salt was stirred with methylene dichloride to remove the nitrosamine impurity by solvent extraction. Thereafter, follow the general procedure for the isolation of Varenicline base from the aqueous layer. Yield: 14.0 g Example 14

Purification of Varenicline Free Base Using Lactic Acid

A solution of Varenicline free base (20.0 g) in methylene dichloride (100 mL) was stirred with the aqueous solution of Lactic acid (10.23 g, 1.2 eq in 100 mL of water). The aqueous layer containing Varenicline lactate salt was stirred with methylene dichloride to remove the nitrosamine impurity by solvent extraction. Thereafter, follow the general procedure for the isolation of Varenicline base from the aqueous layer Yield: 12.4 g Example 15

Purification of Varenicline Free Base Using Malic Acid

A solution of Varenicline free base (20.0 g) in methylene dichloride (100 mL) was stirred with the aqueous solution of Malic acid (15.23 g, 1.0 eq in 100 mL of water). The aqueous layer containing Varenicline malate salt was stirred with methylene dichloride to remove the nitrosamine impurity by solvent extraction. Thereafter, follow the general procedure for the isolation of Varenicline base from the aqueous layer. Yield: 13.0 g.

Example 16

Purification of Varenicline Free Base Using Malonic Acid

A solution of Varenicline free base (20.0 g) in methylene dichloride (100 ml) was stirred with the aqueous solution of Malonic acid (11.82 g, 1.2 eq in 100 ml of water). The aqueous layer containing Varenicline malonate was stirred with methylene dichloride to remove the nitrosamine impurity by solvent extraction. Thereafter, follow the general procedure for the isolation of Varenicline base from the aqueous layer. Yield: 13.6 g Example 17

Purification of Varenicline Free Base Using Hydrochloric Acid

A solution of Varenicline free base (10.0 g) in methylene dichloride (50.0 ml) was stirred with the aqueous solution of hydrochloric acid (6.9 g of 30% aqueous HCl, in 50 ml of water). The aqueous layer containing Varenicline hydrochloride was stirred with methylene dichloride to remove the nitrosamine impurity by solvent extraction. Thereafter, follow the general procedure for the isolation of Varenicline base from the aqueous layer. Yield 8.0 g Example 18

Purification of Varenicline Free Base Using Succinic Acid

A solution of Varenicline free base (25.0 g) in methylene dichloride (125 mL) was stirred with the aqueous solution of succinic acid (16.77 g, 1.2 eq in 125 mL of water). The aqueous layer containing Varenicline succinate was stirred with methylene dichloride to remove the nitrosamine impurity by solvent extraction. Thereafter, follow the general procedure for the isolation of Varenicline base from the aqueous layer. Yield 15.6 g Example 19

Purification of Varenicline Free Base Using Oxalic Acid

A solution of Varenicline free base (20.0 g) in methylene dichloride (100 ml) was stirred with the aqueous solution of Oxalic acid (14.35 g, 1.2 eq in 100 ml of water). The aqueous layer containing Varenicline oxalate was stirred with methylene dichloride to remove the nitrosamine impurity by solvent extraction. Thereafter, follow the general procedure for the isolation of Varenicline base from the aqueous layer. Yield: 14.6 g.

Example 20

Purification of Varenicline Free Base Using Citric Acid

A solution of Varenicline free base (25.0 g) in methylene dichloride (125 mL) was stirred with the aqueous solution of citric acid (27.28 g, 1.2 eq in 125 mL of water). The aqueous layer containing Varenicline citrate was stirred with methylene dichloride to remove the nitrosamine impurity by solvent extraction. Thereafter, follow the general procedure for the isolation of Varenicline base from the aqueous layer. Yield 16.2 g.

Example 21

Purification of Varenicline Free Base Using Reduction Process

A solution of Varenicline free base (5.0 g) in methanol (50 mL) was stirred under hydrogen (6.0 kg/cm$^2$) pressure in the presence of 10% Palladium on carbon (0.5 g, 50% wet) at 25-35° C. After 6 hours and the reaction mass was filtered through celite pad and rinsed with methanol (50 ml). The filtrate was distilled completely under reduced pressure and co-distilled with methyl tert-butyl ether to remove traces of methanol & water. methyl tert-butyl ether (50.0 mL, 10.0 volume) was added to the concentrated mass and stirred at 5-10° C. for 3 hours. The product was isolated by filtration and washed with chilled methyl tert-butyl ether by twice. The wet material was dried at 40° C. under vacuum. Yield: 4.2 g Example 22

Varenicline Tartrate Maltodextrin Premix

Varenicline free base (7 g) was dissolved in methanol (140 ml) at 25-30° C. In a separate flask, tartaric acid (4.92 g) was dissolved in 70 ml water at 25-30° C. Varenicline solution was mixed with tartaric acid solution at 25-35° C. The resulting clear solution was stirred for 30 min at 25-35° C. to form the Varenicline tartrate salt solution. Maltodextrin (119.84 g) was dissolved in water (420.53 ml) at 25-35° C. separately and added this Maltodextrin solution into Varenicline tartrate solution prepared earlier. The resulting clear solution was stirred for 30 minutes, filtered through a micron filter and washed with water (2×70 ml). The clear filtrate was subjected to spray drying using a spray dryer to obtain the amorphous Varenicline Tartrate Maltodextrin Premix (1:10) API. Yield: 130.0 g. Purity by HPLC: 99.99%.

Example 23

Nitrosamine Impurities Content in Varenicline Base Before and After Purification Using Organic and Inorganic Acid Preparation of Varenicline Tartrate Maltodextrin Premix (1:10) API From the key starting material, 1-(4,5-Dinitro-10-aza-tricyclo[6.3.1.0$^{2,7}$]dodeca-2(7),3,5-trien-10-yl)-2,2,2-trifluoroethanone and purification of varenicline base to eliminate nitrosamine impurities by using organic acids having the pKa preferably between 2 and 6, or inorganic acid are demonstrated in Examples 9-22.

Figure 11:
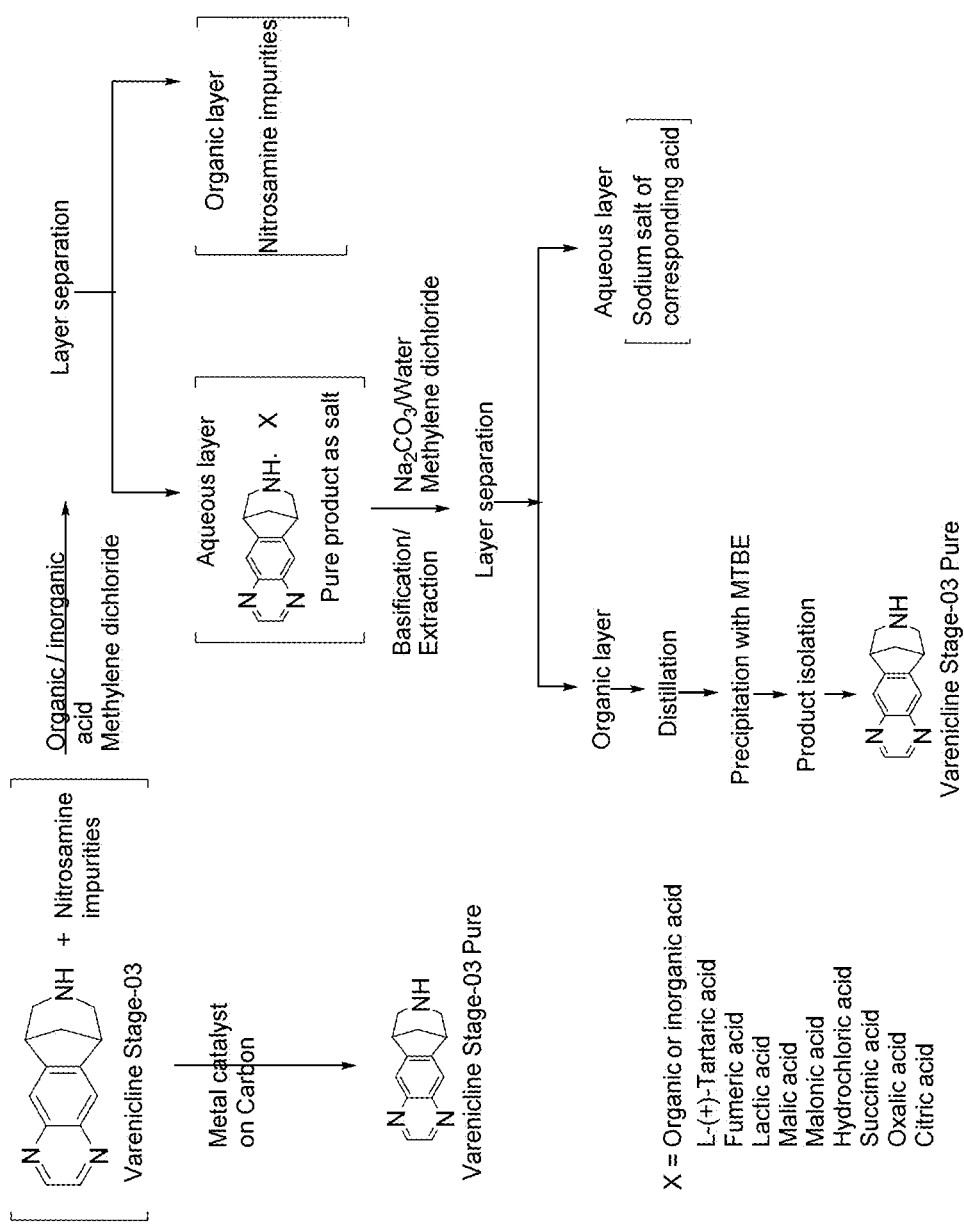
FIG. 11 is a graphical presentation of purification of varenicline free base to eliminate nitrosamine impurities using organic or inorganic acids and also by catalytic hydrogenation in the presence of palladium on charcoal.

The graphical presentation of purification of varenicline free base to eliminate nitrosamine impurities using organic or inorganic acids and also by catalytic hydrogenation in the presence of palladium on charcoal is provided in FIG. 11.

Table 23 provides nitrosamine contents in varenicline base before and after purification using organic or inorganic acids (based on Examples 12-21). Organic acids are selected preferably having the pKa between 2 and 6. Also, it was observed that varenicline base contaminated with varenicline nitrosamine is subjected to reduction under hydrogen pressure in the presence of palladium on carbon eliminates the varenicline nitrosamine impurity (Refer Example—21 and S. No. 10 of Table 23) to the desired limit.

TABLE 23

Nitrosamine Contents in Varenicline Base Before and After Purification Using Organic or Inorganic Acids

| S. No | Inorganic and Organic acid used for purification | Varenicline Nitrosamine impurity in ppm | | Dinitro nitrosamine Impurity in ppm | | Diamino nitrosamine Impurity in ppm | |
|---|---|---|---|---|---|---|---|
| | | Before Purification | After Purification | Before Purif. | After Purifi. | Before Purifi. | After Purifi. |
| 1 | L-(+)-Tartaric acid | 16.57 | 1.76 | ND | ND | ND | ND |
| 2 | Fumeric acid | 16.57 | 2.93 | ND | ND | ND | ND |
| 3 | Lactic acid | 19.22 | 3.08 | ND | ND | ND | ND |
| 4 | Malic acid | 19.22 | 4.48 | ND | ND | ND | ND |
| 5 | MaIonic acid | 19.22 | 3.87 | ND | ND | ND | ND |
| 6 | Hydrochloric acid | 16.57 | 2.26 | ND | ND | ND | ND |
| 7 | Succinic acid | 16.57 | 1.85 | ND | ND | ND | ND |
| 8 | Oxalic acid | 16.57 | 2.77 | ND | ND | ND | ND |
| 9 | Citric acid | 16.57 | 1.42 | ND | ND | ND | ND |
| 10 | Reduction by Pd/C | 19.22 | 0.75 | ND | ND | ND | ND |

ND: Not Detected

Note:
Dinitro nitrosamine Impurity and Diamino nitrosamine Impurity both are controlled in Stage-3 crude itself.

Conclusion: This result demonstrates that nitrosamine can be eliminated from the varenicline free base (crude) by forming salts with various organic or inorganic salts in aqueous solution and unprotanated nitrosamines are removed by solvent extraction. Thereafter, pure free varenicline base can be isolated from the aqueous varenicline salt solution by basification (purification of varenicline by acid-base treatment). Varenicline base was analyzed by LCMS for determining nitrosamine contents before and after purification of varenicline base.

Those of ordinary skill in the art will recognize, or be able to ascertain using no more than routine experimentation, equivalents to the specific embodiments of the invention described herein. Such equivalents are intended to be encompassed by the following claims.

What is claimed is:

1. A pharmaceutical composition in the form of a tablet, comprising varenicline tartrate and means for controlling the level of N-nitroso-varenicline (7,8,9,10-tetrahydro-8-nitroso-6,10-Methano-6H-pyrazino[2,3-h][3] benzazepine) impurity to less than 50 ppm per tablet as measured by LC-ESI-HRMS (U.S. FDA Method), wherein the varenicline tartrate is dispersed in a maltodextrin matrix.

2. A pharmaceutical composition, comprising varenicline tartrate maltodextrin premix having less than 50 ppm N-nitroso-varenicline (7,8,9,10-tetrahydro-8-nitroso-6,10-Methano-6H-pyrazino[2,3-h][3] benzazepine) impurity as measured by LCMS.

3. The pharmaceutical composition of claim 2, comprising generally spherical agglomerations of varenicline tartrate and maltodextrin.

4. The pharmaceutical composition of claim 2, wherein the varenicline tartrate is present in an amount of about 0.85 mg to about 1.7 mg, the maltodextrin is present in an amount of about 5 mg to about 50 mg, and wherein the composition further comprises:
   a. about 5 mg to about 15 mg croscarmellose sodium;
   b. about 100 mg to about 200 mg microcrystalline cellulose; and
   c. about 0.5 mg to about 2 mg stearic acid,
   wherein the composition is formulated into a tablet and comprises less than 15 ppm N-nitroso-varenicline impurity per tablet as measured by LC-ESI-HRMS (U.S. FDA Method).

5. The pharmaceutical composition of claim 2, wherein the composition is in the form of a tablet, comprises about 0.85 mg to about 1.7 mg varenicline tartrate, and comprises less than 25 ppm N-nitroso-varenicline impurity per tablet as measured by LC-ESI-HRMS (U.S. FDA Method).

6. The pharmaceutical composition of claim 2, wherein the varenicline tartrate is approximately uniformly dispersed in the maltodextrin matrix.

7. The pharmaceutical composition of claim 2, wherein the premix is spray-dried.

8. The pharmaceutical composition of claim 2, wherein the composition is formulated into a tablet comprising varenicline tartrate, microcrystalline cellulose and croscarmellose sodium having less than 20 ppm N-nitroso-varenicline impurity as measured by LC-ESI-HRMS (U.S. FDA Method).

9. The pharmaceutical composition of claim 1, wherein the tablet comprises about 1.7 mg of the varenicline tartrate, or about 0.85 mg of the varenicline tartrate, and has less than 25 ppm of the N-nitroso-varenicline impurity per tablet.

10. The pharmaceutical composition of claim 1, wherein the tablet comprises about 1.7 mg of the varenicline tartrate, or about 0.85 mg of the varenicline tartrate, and has less than 19 ppm of the N-nitroso-varenicline impurity per tablet.

11. The pharmaceutical composition of claim 1, wherein the tablet comprises about 1.7 mg of the varenicline tartrate, or about 0.85 mg of the varenicline tartrate, and has less than 5 ppm of the N-nitroso-varenicline impurity per tablet.

* * * * *